United States Patent
Brown et al.

(10) Patent No.: US 8,075,919 B2
(45) Date of Patent: *Dec. 13, 2011

(54) METHODS FOR FABRICATION, USES AND COMPOSITIONS OF SMALL SPHERICAL PARTICLES PREPARED BY CONTROLLED PHASE SEPARATION

(75) Inventors: Larry Brown, Newton, MA (US); John K. McGeehan, Woodbury, NJ (US); Julia Rashba-Step, Newton, MA (US); Terrence L. Scott, Winchester, MA (US)

(73) Assignees: Baxter International Inc., Deerfield, IL (US); Baxter Healthcare S.A., Wallisellen (CH)

( * ) Notice: Subject to any disclaimer, the term of this patent is extended or adjusted under 35 U.S.C. 154(b) by 827 days.

This patent is subject to a terminal disclaimer.

(21) Appl. No.: 10/894,430

(22) Filed: Jul. 19, 2004

(65) Prior Publication Data

US 2005/0142206 A1    Jun. 30, 2005

Related U.S. Application Data

(60) Provisional application No. 60/488,712, filed on Jul. 18, 2003.

(51) Int. Cl.
*A61K 9/16* (2006.01)
(52) U.S. Cl. .................. 424/489; 424/490
(58) Field of Classification Search .............. None
See application file for complete search history.

(56) References Cited

U.S. PATENT DOCUMENTS

| | | |
|---|---|---|
| 3,102,077 A | 8/1963 | Christensen |
| 3,737,337 A | 6/1973 | Schnoring et al. |
| 3,891,570 A | 6/1975 | Fukushima et al. |
| 4,389,330 A | 6/1983 | Tice et al. |
| 4,530,840 A | 7/1985 | Tice et al. |
| 4,652,441 A | 3/1987 | Okada et al. |
| 4,728,721 A | 3/1988 | Yamamoto et al. |
| 4,818,542 A | 4/1989 | DeLuca et al. |
| 4,849,228 A | 7/1989 | Yamamoto et al. |
| 4,853,462 A * | 8/1989 | Hostetler et al. ............. 528/494 |
| 4,861,627 A | 8/1989 | Mathiowitz et al. |
| 4,897,268 A | 1/1990 | Tice et al. |
| 4,904,479 A | 2/1990 | Illum |
| 4,917,893 A | 4/1990 | Okada et al. |
| 5,066,436 A | 11/1991 | Komen et al. |
| 5,075,109 A | 12/1991 | Tice et al. |
| 5,102,872 A | 4/1992 | Singh et al. |
| 5,149,543 A | 9/1992 | Cohen et al. |
| 5,213,812 A | 5/1993 | Ruiz |
| 5,300,464 A | 4/1994 | Rittler |
| 5,330,767 A | 7/1994 | Yamamoto et al. |
| 5,330,768 A | 7/1994 | Park et al. |
| 5,360,610 A | 11/1994 | Tice et al. |
| 5,384,133 A | 1/1995 | Boyes et al. |
| 5,407,609 A | 4/1995 | Tice et al. |
| 5,417,986 A | 5/1995 | Reid et al. |
| 5,422,120 A | 6/1995 | Kim |
| 5,476,663 A | 12/1995 | Okada et al. |
| 5,480,656 A | 1/1996 | Okada et al. |
| 5,482,927 A | 1/1996 | Maniar et al. |
| 5,543,158 A | 8/1996 | Gref et al. |
| 5,556,642 A | 9/1996 | Kobayashi et al. |
| 5,575,987 A | 11/1996 | Kamei et al. |
| 5,578,709 A | 11/1996 | Woiszwillo |
| 5,599,719 A | 2/1997 | Woiszwillo |
| 5,603,961 A | 2/1997 | Suzuki et al. |
| 5,631,020 A | 5/1997 | Okada et al. |
| 5,631,021 A | 5/1997 | Okada et al. |
| 5,643,607 A | 7/1997 | Okada et al. |
| 5,650,173 A | 7/1997 | Ramstack et al. |
| 5,654,008 A | 8/1997 | Herbert et al. |
| 5,654,010 A | 8/1997 | Johnson et al. |
| 5,665,428 A | 9/1997 | Cha et al. |
| 5,667,808 A | 9/1997 | Johnson et al. |
| 5,716,640 A | 2/1998 | Kamei et al. |
| 5,851,451 A | 12/1998 | Takechi et al. |
| 5,891,478 A | 4/1999 | Johnson et al. |
| 5,932,248 A | 8/1999 | Chen et al. |

(Continued)

FOREIGN PATENT DOCUMENTS

CA    2157793 C    9/1994

(Continued)

OTHER PUBLICATIONS

"Yang, et al., Crystalline monoclonal antibodies for subcutaneous delivery, Proc. Natl. Acad. Sci (USA), Jun. 10, 2003, vol. 100, No. 12, pp. 6934-6939."
Supplementary European Search Report for European patent application 04809503. dated Aug. 22, 2007.
Van Der Lubben et al., "Chitosan microparticles for mucosal vaccination against diphtheria: oral and nasal efficacy studies in mice," *Vaccine*, 21:1400-1408 (2003).
Brazeau et al., "In vitro myotoxicity of selected cationic macromolecules used in non-viral gene delivery", 1998, Pharmaceutical Research, vol. 15(5), pp. 680-684.
Brown et al., "Pulmonary Delivery of Novel Insulin Microspheres", 2002, Proceed, Respiratory Drug Delivery VIII, DHI Publishing, Raleigh, N. C., 431-434.
Brown et al., "PROMAXX Microsphere Characterization", 2004, Proceed. Of Resp. Drug. Del. IX, pp. 477-479.
Bustami et al., "Generation of Micro-Particles of Proteins for Aerosol Delivery Using High Pressure Modified Carbon Dioxide", 2000, Pharmaceutical Research, vol. 17, pp. 1360-1366.
Chu et al., "Efficiency of cytoplasmic delivery by pH-sensitive liposomes to cells in culture", 1990, Pharmaceutical Research, vol. 7, pp. 824-834.

(Continued)

*Primary Examiner* — S. Tran
(74) *Attorney, Agent, or Firm* — Marshall, Gerstein & Borun LLP

(57) ABSTRACT

The present invention is related to a method for preparing small spherical particles of an active agent by providing a solution in a single liquid phase. The single liquid phase comprises an active agent, a phase separation enhancing agent, and a first solvent. A phase change is induced at a controlled rate in the solution to cause a liquid-solid phase separation of the active agent and to form a solid phase and a liquid phase. The solid phase comprises solid small spherical particles of the active agent. The liquid phase comprises the phase separation enhancing agent and the solvent. The small spherical particles are substantially spherical and having a size from about 0.01 μm to about 200 μm.

70 Claims, 36 Drawing Sheets

U.S. PATENT DOCUMENTS

| | | | |
|---|---|---|---|
| 5,945,126 | A | 8/1999 | Thanoo et al. |
| 5,981,719 | A | 11/1999 | Woiszwillo et al. |
| 5,989,463 | A | 11/1999 | Tracy et al. |
| 6,036,976 | A | 3/2000 | Takechi et al. |
| 6,042,792 | A * | 3/2000 | Shefer et al. ............... 422/259 |
| 6,051,259 | A | 4/2000 | Johnson et al. |
| 6,063,910 | A | 5/2000 | Debenedetti et al. |
| 6,090,925 | A | 7/2000 | Woiszwillo et al. |
| 6,120,787 | A | 9/2000 | Gustafsson et al. |
| 6,153,211 | A | 11/2000 | Hubbell et al. |
| 6,268,053 | B1 | 7/2001 | Woiszwillo et al. |
| 6,270,795 | B1 | 8/2001 | Jones et al. |
| 6,270,802 | B1 | 8/2001 | Thanoo et al. |
| 6,361,798 | B1 | 3/2002 | Thanoo et al. |
| 6,395,253 | B2 | 5/2002 | Levy et al. |
| 6,395,302 | B1 | 5/2002 | Hennink et al. |
| 6,455,074 | B1 | 9/2002 | Tracy et al. |
| RE37,872 | E | 10/2002 | Franks et al. |
| 6,458,387 | B1 | 10/2002 | Scott et al. |
| 6,500,448 | B1 | 12/2002 | Johnson et al. |
| 6,506,410 | B1 | 1/2003 | Park et al. |
| 6,596,316 | B2 | 7/2003 | Lyons et al. |
| 6,616,949 | B2 | 9/2003 | Jonsson et al. |
| RE38,385 | E | 1/2004 | Hatley et al. |
| 6,749,866 | B2 | 6/2004 | Bernstein et al. |
| 6,830,737 | B2 | 12/2004 | Ramstack |
| 6,861,064 | B1 | 3/2005 | Laakso et al. |
| 2001/0002261 | A1 | 5/2001 | Morrison et al. |
| 2003/0007990 | A1 | 1/2003 | Blankenship et al. |
| 2003/0059474 | A1 | 3/2003 | Scott et al. |
| 2003/0064033 | A1 | 4/2003 | Brown et al. |
| 2003/0211153 | A1 | 11/2003 | Johnson et al. |
| 2004/0039171 | A1 | 2/2004 | Matsumoto et al. |
| 2004/0043076 | A1 | 3/2004 | Dulieu et al. |
| 2005/0142201 | A1 | 6/2005 | Rashba-Step et al. |
| 2005/0142205 | A1 | 6/2005 | Rashba-Step et al. |
| 2005/0147687 | A1 | 7/2005 | Rashba-Step et al. |
| 2005/0170005 | A1 | 8/2005 | Rashba-Step et al. |
| 2005/0233945 | A1 | 10/2005 | Brown et al. |
| 2006/0024379 | A1 | 2/2006 | Brown et al. |
| 2007/0092452 | A1 | 4/2007 | Rashba-Step et al. |
| 2008/0026068 | A1 * | 1/2008 | Brown et al. ............... 424/489 |

FOREIGN PATENT DOCUMENTS

| | | | |
|---|---|---|---|
| EP | 248531 | A2 | 1/1986 |
| EP | 0377477 | | 7/1990 |
| EP | 809110 | A1 | 11/1997 |
| EP | 1060741 | A1 * | 12/2000 |
| JP | 11-302156 | A | 11/1999 |
| RU | 2147226 | | 4/2000 |
| WO | WO-93/14110 | | 7/1993 |
| WO | WO 94/20856 | | 9/1994 |
| WO | WO 9420856 | A1 * | 9/1994 |
| WO | WO9500128 | A1 | 1/1995 |
| WO | WO-96/09814 | | 4/1996 |
| WO | WO-96/38153 | A1 | 12/1996 |
| WO | WO-99/55310 | A1 | 11/1999 |
| WO | WO-00/00176 | | 1/2000 |
| WO | WO-02/39985 | A1 | 5/2002 |
| WO | WO-02/43580 | | 6/2002 |
| WO | WO-02/055059 | A2 | 7/2002 |
| WO | WO 03/000014 | A2 | 1/2003 |
| WO | WO-03/015750 | | 2/2003 |
| WO | WO 03015750 | A1 * | 2/2003 |

OTHER PUBLICATIONS

Moghimi, "Chemical camouflage of nanospheres with a poorly reactive surface: towards development of stealth and target-specific nanocarriers", 2002, Biochimica et Biophysica Acta, vol. 1590, pp. 131-139.

Morita et al., "Formation and Isolation of Spherical Fine Protein Microparticles Through Lyophilization of Protein-Poly (ethylene Glycol) Aqueous Mixture", 2000, Pharmaceutical Research, vol. 17(11), pp. 1367-1373.

Rashba-Step et al., "Albumin Microspheres as Drug Delivery Vehicle for Multiple Routes of Administration", 2001, Proceed. Int'l. Symp. Control. Rel. Bioact. Material, vol. 28, pp. 1001-1002.

Sah et al., "Biodegradable microcapsules prepared by a w/o/w technique: effects of shear force to make a primary w/o emulsion on their morphology and protein release", Journal of Microencapsulation, 1995, vol. 12(1), pp. 59-69.

Sinha et al., "Biodegradable microspheres for protein delivery", 2003, Journal of Controlled Release, vol. 90, pp. 261-280.

Vanderkerken et al., Synthesis and evaluation of poly(ethylene glycol)-polylysine block copolymers as carriers for gene delivery, 2000, Journal of Bioactive and Compatible Polymers, vol. 15(2), pp. 115-138.

Report of the International Searching Authority, Sep. 9, 2005, PCT/US05/016651 pp. 1-6.

Opinion of the International Searching Authority, Sep. 9, 2005, PCT/US05/016651 pp. 1-6.

Report of the International Searching Authority, Nov. 3, 2005, PCT/US04/023182 pp. 1-3.

Opinion of the International Searching Authority, Nov. 3, 2005, PCT/USO4/023182 pp. 1-3.

Nonfinal office action from corresponding U.S. Appl. No. 10/894,408, dated Nov. 2. 2007.

Final office action from corresponding U.S. Appl. No. 10/894,408, dated Aug. 1, 2008.

Final office action from corresponding U.S. Appl. No. 10/894,408, dated May 4, 2009.

Nonfinal office action from corresponding U.S. Appl. No. 10/894,408, dated Aug. 16, 2010.

Nonfinal office action from corresponding U.S. Appl. No. 10/894,432, dated May 22, 2008.

Nonfinal office action from corresponding U.S. Appl. No. 10/894,429, dated Apr. 10 2007.

Final office action from corresponding U.S. Appl. No. 10/894,429, dated Jan. 22, 2008.

Nonfinal office action from corresponding U.S. Appl. No. 10/894,429, dated Oct. 29, 2008.

Final office action from corresponding U.S. Appl. No. 10/894,429, dated Aug. 6, 2009.

Final office action from corresponding U.S. Appl. No. 10/894,432, dated Mar. 5, 2009.

Nonfinal office action from corresponding U.S. Appl. No. 10/894,432, dated May 11, 2010.

Nonfinal office action from corresponding U.S. Appl. No. 10/894,410, dated Sep. 10, 2008.

Final office action from corresponding U.S. Appl. No. 10/894,410, dated Jun. 3, 2009.

Nonfinal office action from corresponding U.S. Appl. No. 11/033,780, dated Apr. 16, 2008.

Final office action from corresponding U.S. Appl. No. 11/033,780, dated Jun. 5, 2009.

Nonfinal office action fro corresponding U.S. Appl. No. 11/127,704 dated Dec. 12, 2007.

Nonfinal office action from corresponding U.S. Appl. No. 11/127,704 dated Jul. 17, 2006.

Final office action from corresponding U.S. Appl. No. 11/127,704 dated Mar. 22, 2007.

Final office action from corresponding U.S. Appl. No. 11/127,704 dated Sep. 18, 2008.

Nonfinal office action from corresponding U.S. Appl. No. 11/127,704 dated Jun. 2, 2009.

Final office action from corresponding U.S. Appl. No. 11/127,704 dated Mar. 19, 2010.

Itaka et al., Molecular weight and mixing property of a solute in a frozen solution, Abstract from 123rd Annual Meeting of the Pharmaceutical Society of Japan, p. 97 (Mar. 2003).

Annunziata et al., Effect of polyethylene glycol on the liquid-liquid phase transition in aqueous protein solutions, *Proceedings of the National Academy of Sciences*, 99:14165-70 (2002).

Ataka, The initial process of protein crystal growth, *Japanese Assoc. for Crystal Growth*, 30:13-20 (2003).

Office Action from corresponding Japanese Application No. 2006-520406, dated Oct. 12, 2010.

US 5,849,884, 12/1998, Woiszwillo et al. (withdrawn)

* cited by examiner

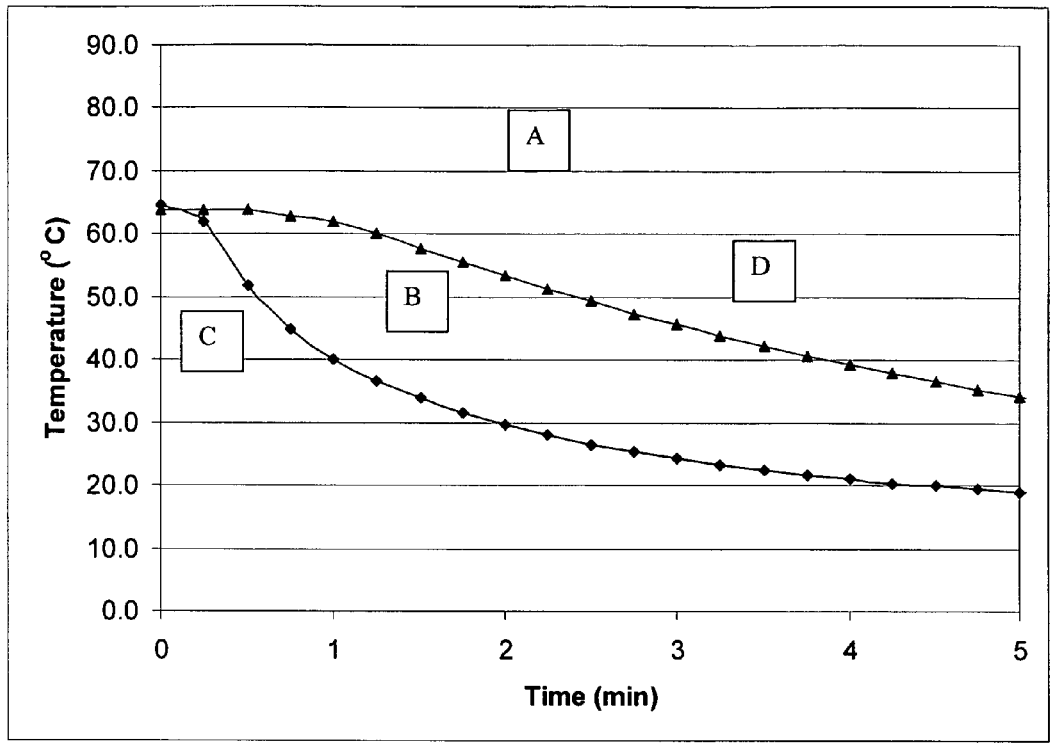

FIG. 2. *Influence of solution temperature and rate of cooling on the phase change of insulin in a buffered polymer solution. At temperatures above 60°C, insulin remains in solution (region A). Region B represents the area of optimal small spherical particles formation bounded by the highest (♦) and lowest (▲) temperature change rates observed in the heat exchanger. Faster cooling rates (region C) result in the formation of very fine non-spherical particles, whereas slower cooling rates (region D) results in a mixture of various sized small spherical particles along with irregularly shaped particles and a flocculent precipitate.*

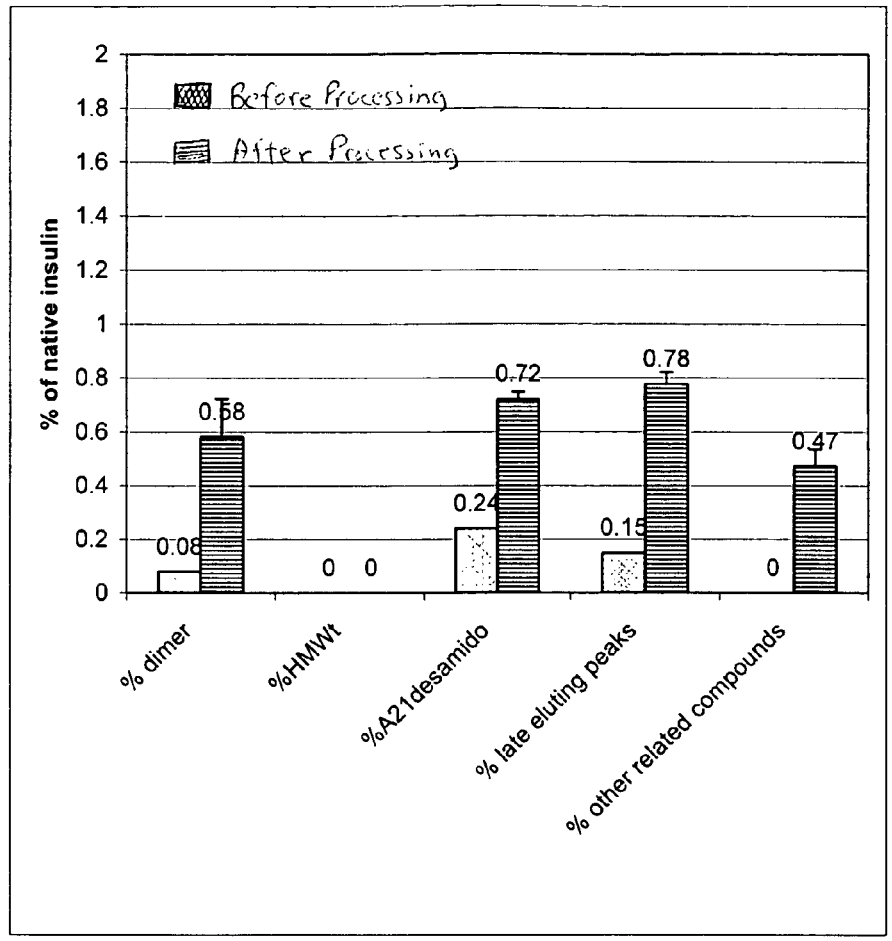
FIG. 4. Chemical stability during insulin microsphere fabrication process. HPLC analysis indicated no increase in high molecular weight compounds associated with the process, and increases (over the starting insulin raw material) in % dimer, % A21 desamido insulin, % late eluting peaks, and % other compounds were within USP limits.

FIG. 5. *Insulin small spherical particle size distribution (Aerosizer time-of-flight data). For all six batches produced, greater than 96% of the particle sizes fell between 0.86 and 2.9 microns, with over 60% falling between 1.6 and 2.5 microns. Less than 1.1% of the small spherical particles fell outside of the size range covered by the graph.*

FIG. 6. *Insulin small spherical particle size distribution by Anderson Cascade Impactor. Data is an average (mean +/- SD) of results from six batches of insulin small spherical particles delivered from a Cyclohaler device at 60 LPM. The ECD for stages 1, 2, 3, and 4 were 4.4, 3.3, 2.0, and 1.1 µm respectively.*

FIG. 7: Schematic Diagram of the Continuous Flow-Through Process for making Insulin small spherical particles FIG. 8: A Scanning Electron Micrograph (at 10 Kv and 6260X magnification) of the Insulin small spherical particles produced by the Continuous Flow-Through Process

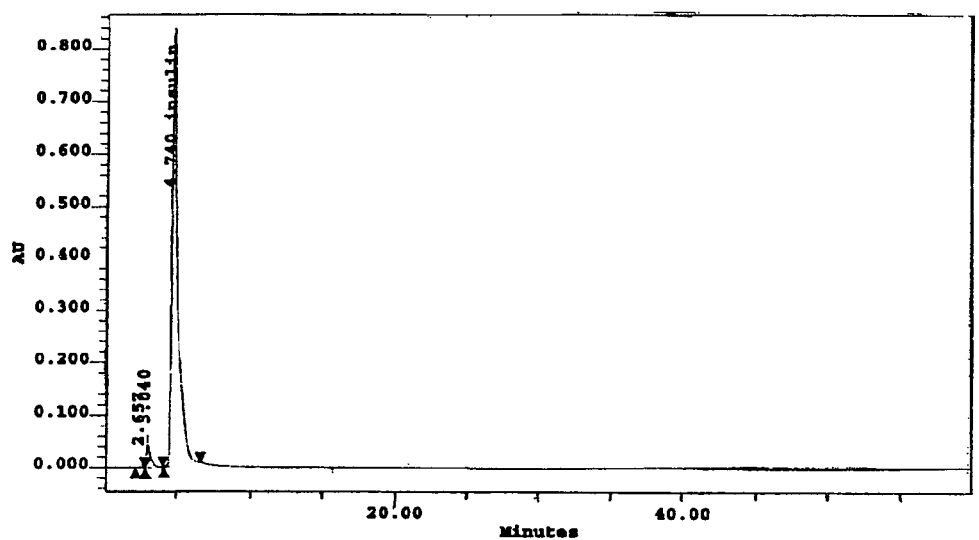
FIG. 9: HLPC Chromatrograph of Dissolved Insulin small spherical particles prepared by the Continuous Flow-Through Process

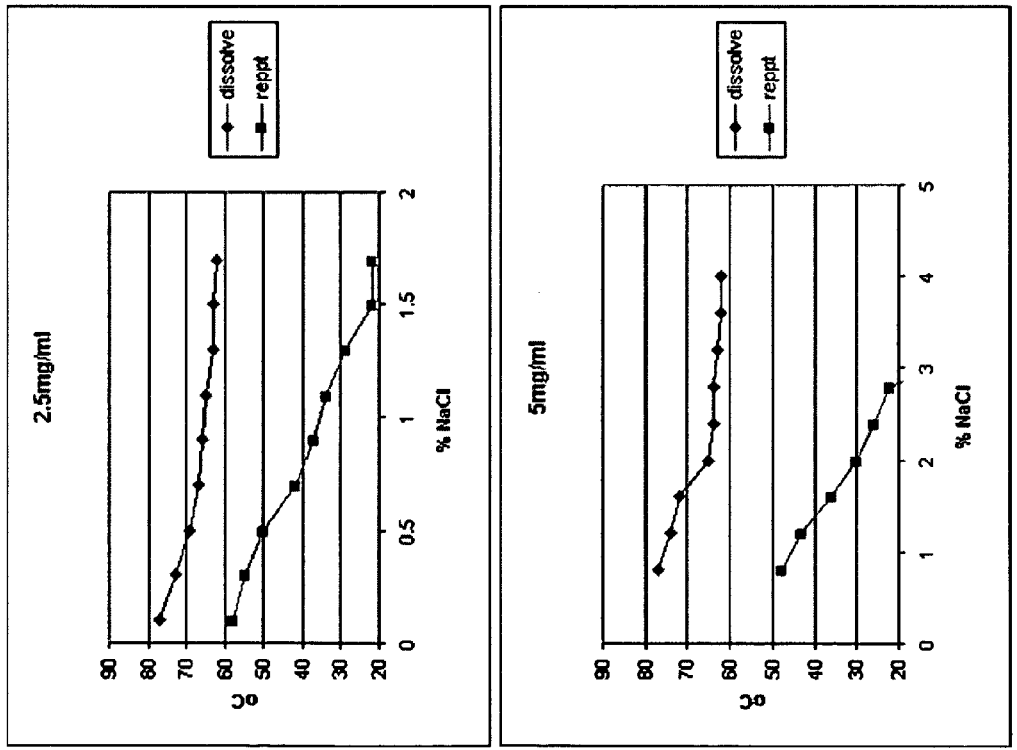
FIGS. 10a-d: Insulin- Test Tube scale NaCl vs temp

10mg/ml

| % NaCl | 1.0 | 2.0 | 3.0 | 4.0 | 5.0 | | | | | | ramp up from 40C |
|---|---|---|---|---|---|---|---|---|---|---|---|
| dissolve oC | 85 | | 83 | | 74 | | 70 | | | 68 | |
| reppt oC | 67 | 46 | 33 | 23 | 20 | | | | | | |

| % NaCl | 2.2 | 2.4 | 2.6 | 2.8 | 3.0 | 3.2 | 3.4 | 3.6 | 3.8 | 4.0 | ramp up from 68C |
|---|---|---|---|---|---|---|---|---|---|---|---|
| dissolve oC | 74 | 74 | 74 | 73 | 71 | 70 | 70 | 70 | 70 | 69 | |
| reppt oC | 39 | 37 | 37 | 35 | 31 | 30 | 27 | 26 | 24 | 22 | |

20mg/ml

| % NaCl | 1.0 | 2.0 | 3.0 | 4.0 | 5.0 | | | ramp up from 40C |
|---|---|---|---|---|---|---|---|---|
| dissolve oC | 88 | | 83 | | 80 | | 77 | 74 |
| reppt oC | 67 | 60 | 49 | 40 | 27 | | | |

FIG. 10h
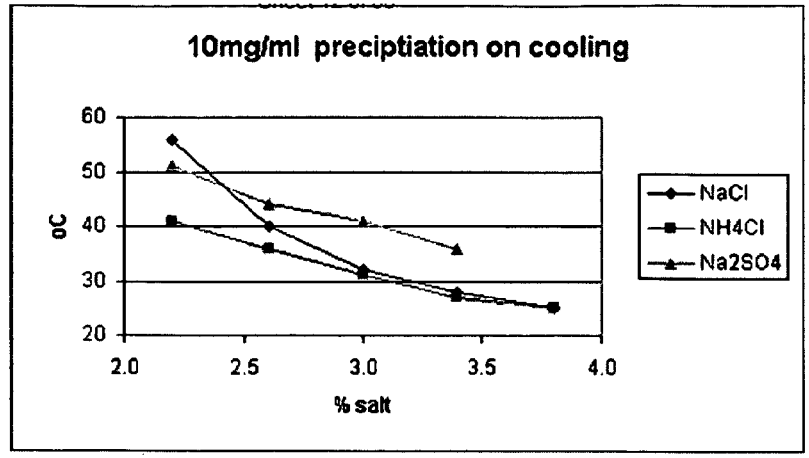
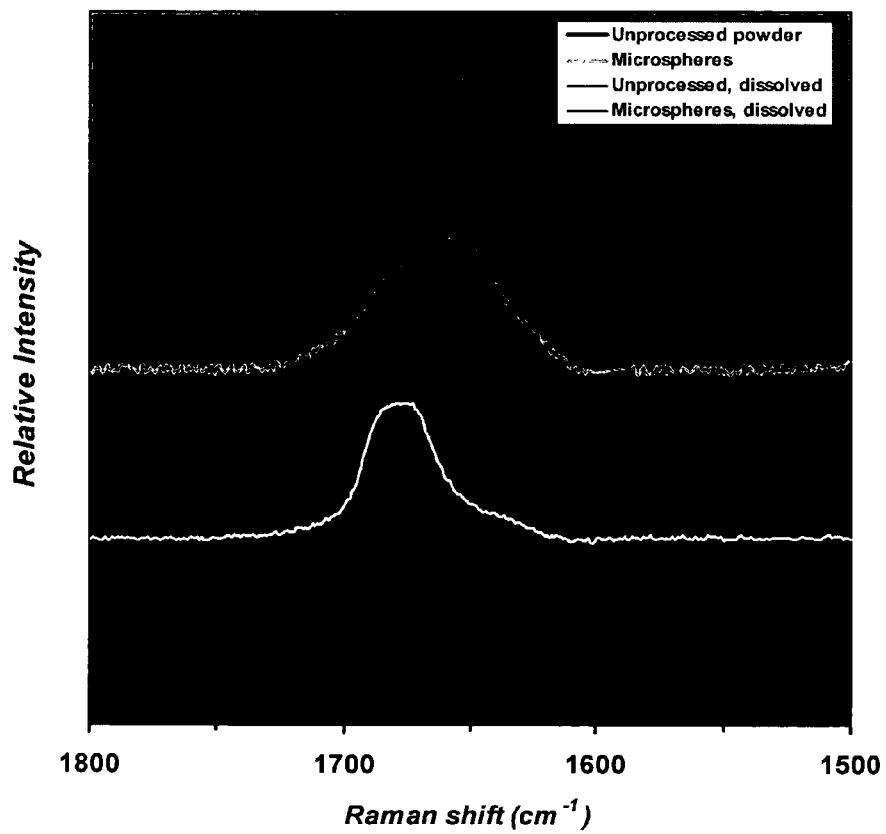
FIG. 10i. Raman spectra in the amide I band region taken with unprocessed insulin powder and small spherical particle powder, as well as with their respective solutions. The spectra were corrected for the aromatic and fluorescence background and solvent, if any.

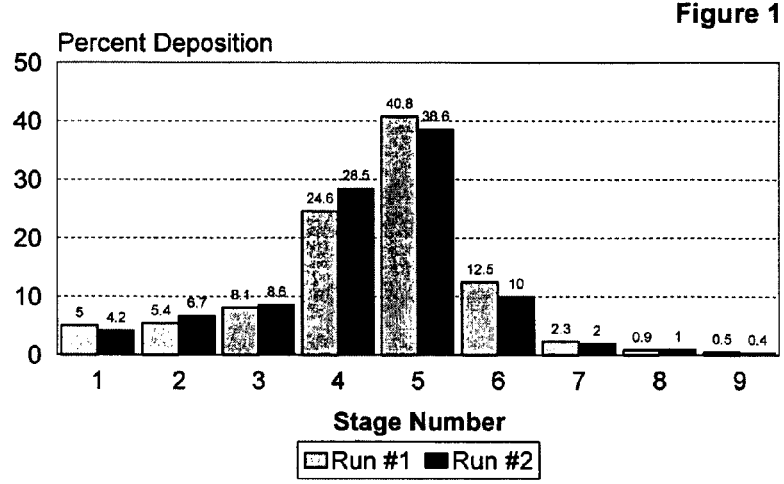
FIG. 11. Andersen Cascade Impactor results for the $^{99m}$Tc radiolabeled insulin powder indicate stable association of the $^{99m}$Tc with the insulin before the first dog was administered the dose and after the final animal was delivered the dose.

| FIG. 12 shows a mean P/I ratio of 0.93 for the five dogs tested. | 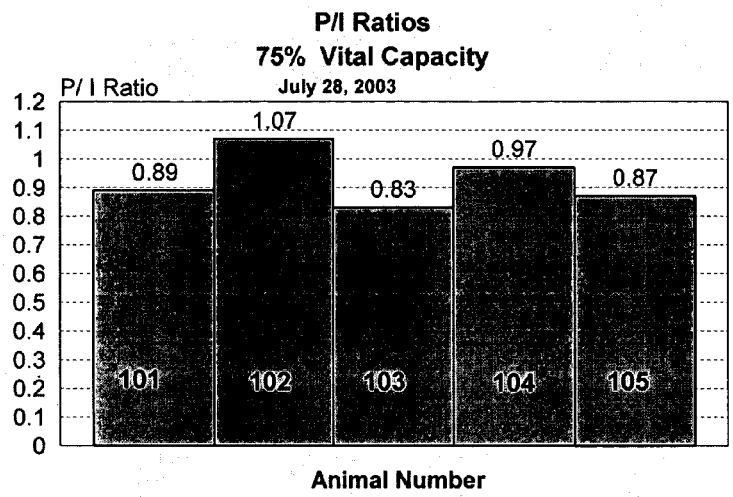 |
| FIG. 13 $^{99m}$Tc radiolabeled insulin was homogeneously distributed throughout the peripheral lung. There is no visual evidence of central lung deposition. This supports the uni-modal particle size distribution of insulin small spherical particles after administration to the dogs. | 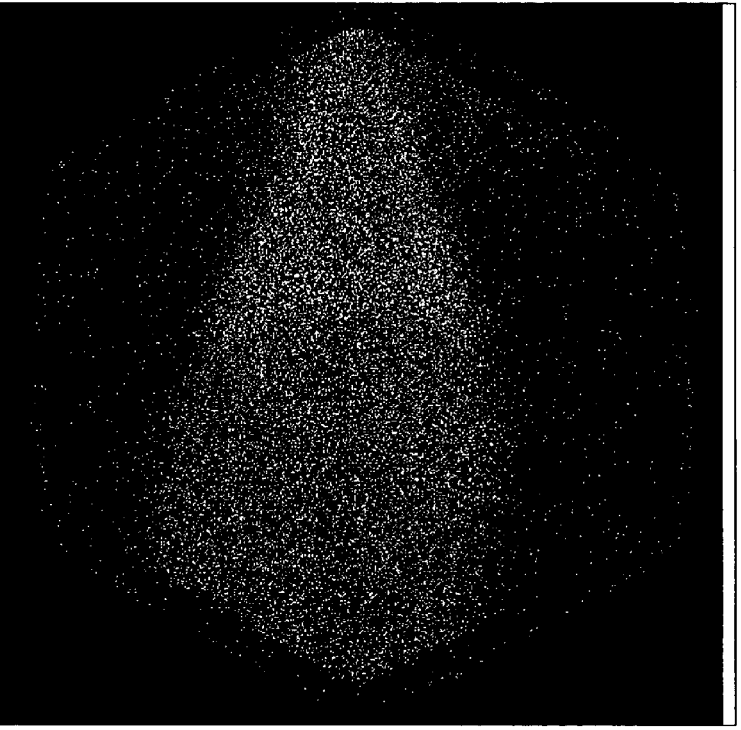 |

FIG. 14a
Circular Dichroism
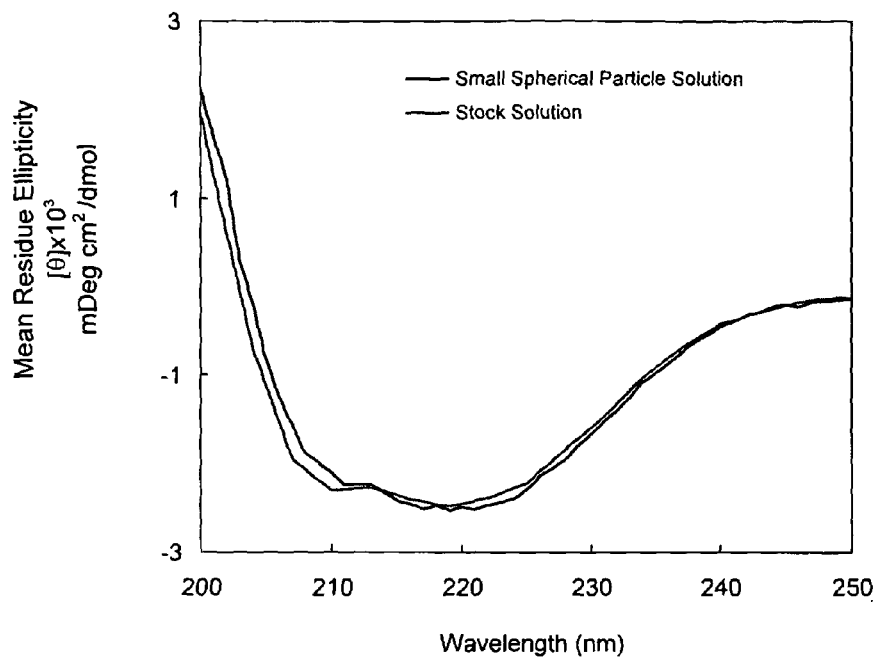
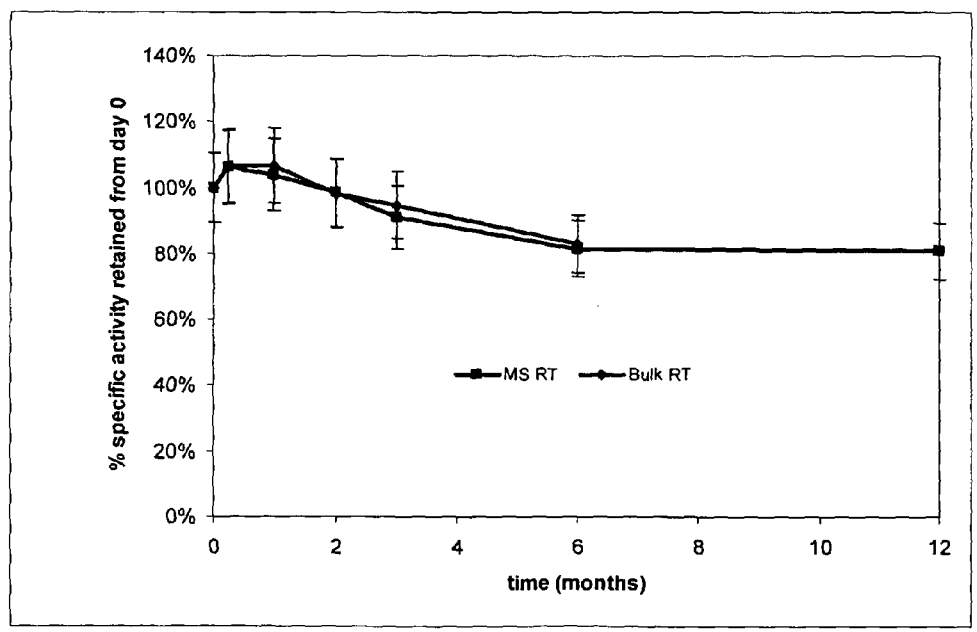

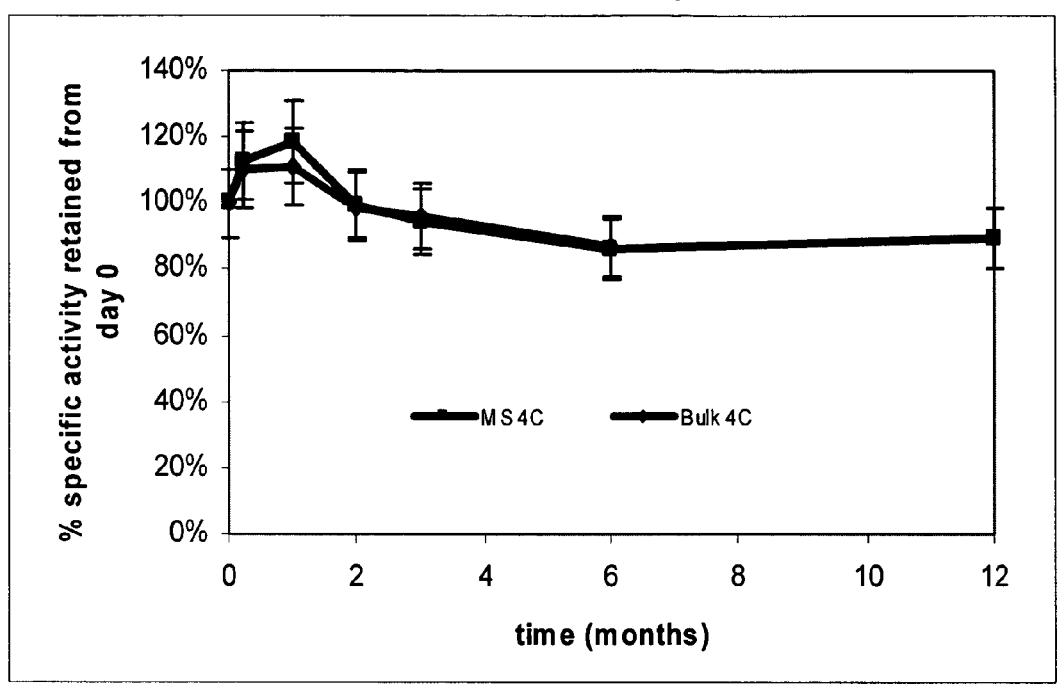
FIG. 14c shelf stability

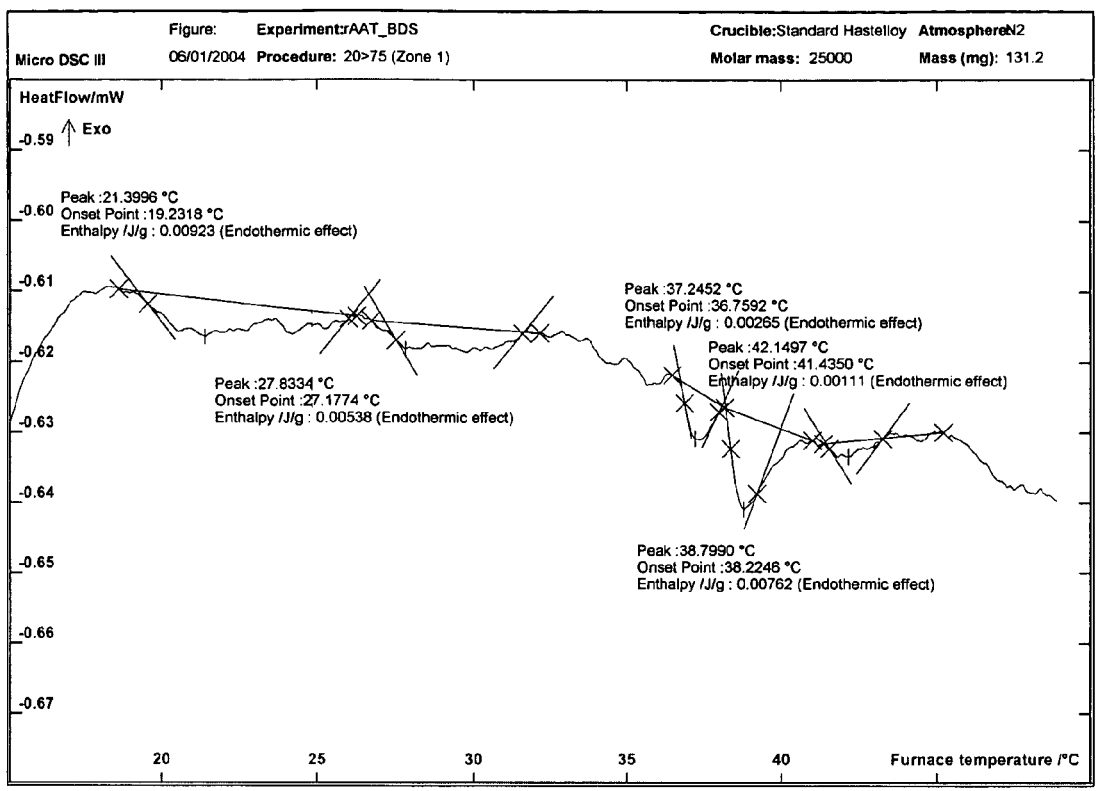
FIG. 15. A first heating thermogram of a 50 mg/mL rAAT sample in BDS solution vs BDS as a reference.
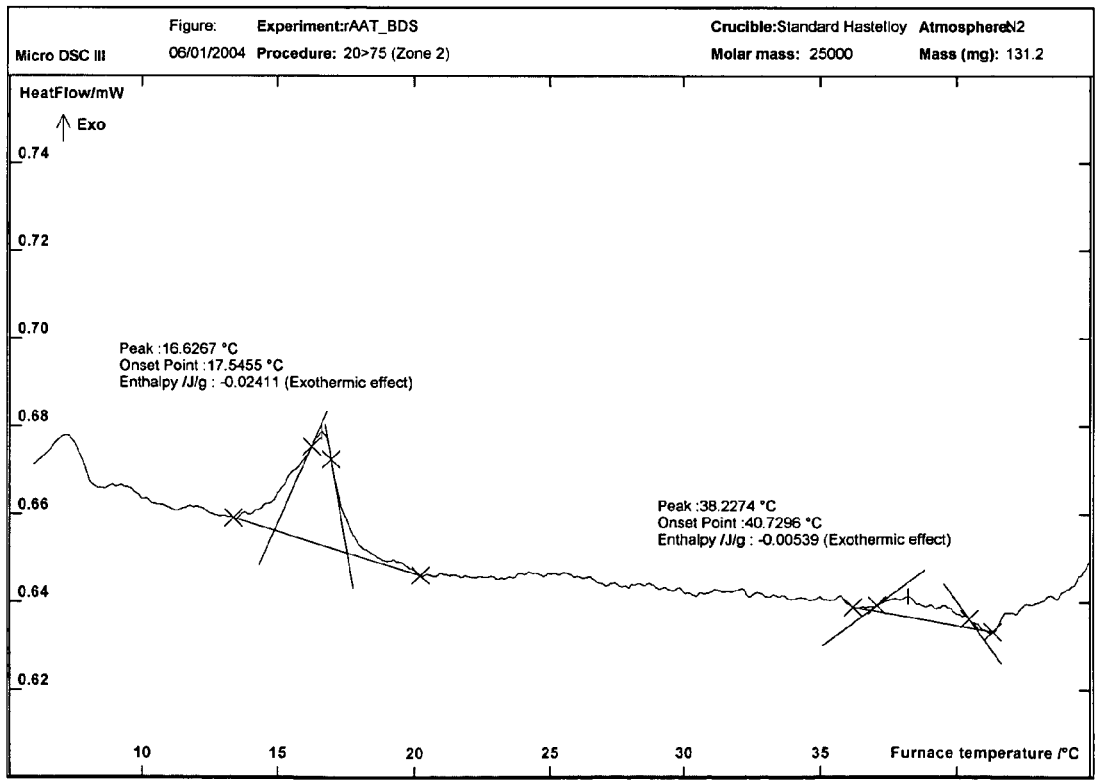
FIG. 16. A first cooling thermogram of a 50 mg/mL rAAT sample in BDS solution vs BDS as a reference.

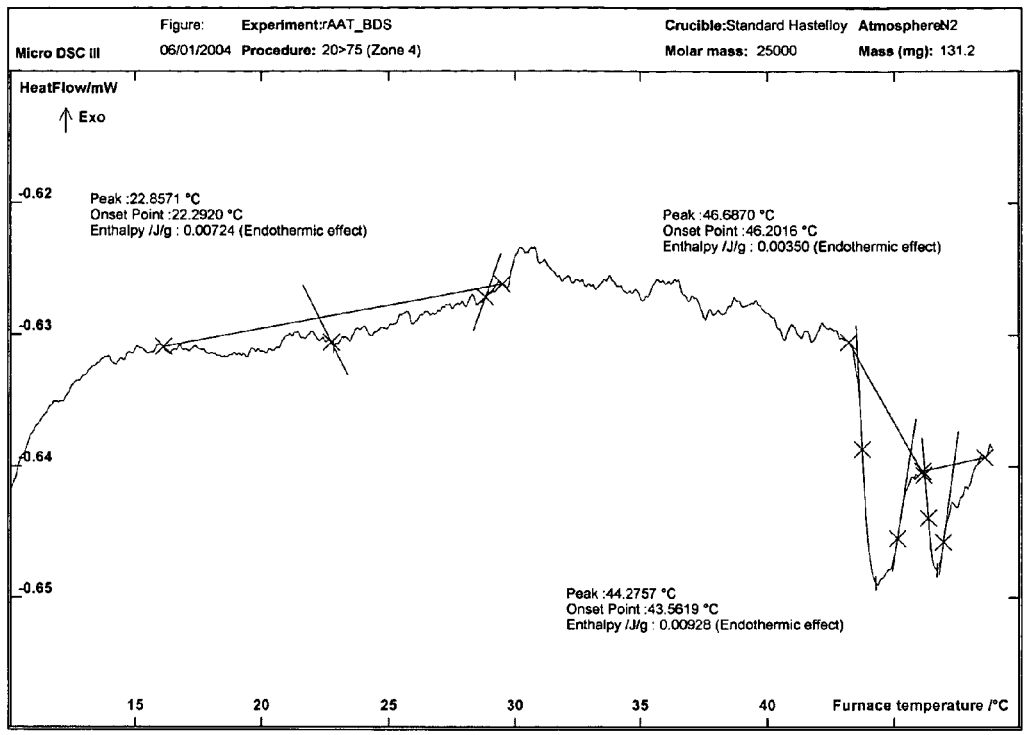
FIG. 17. A second heating thermogram of a 50 mg/mL rAAT sample in BDS solution vs BDS as a reference.
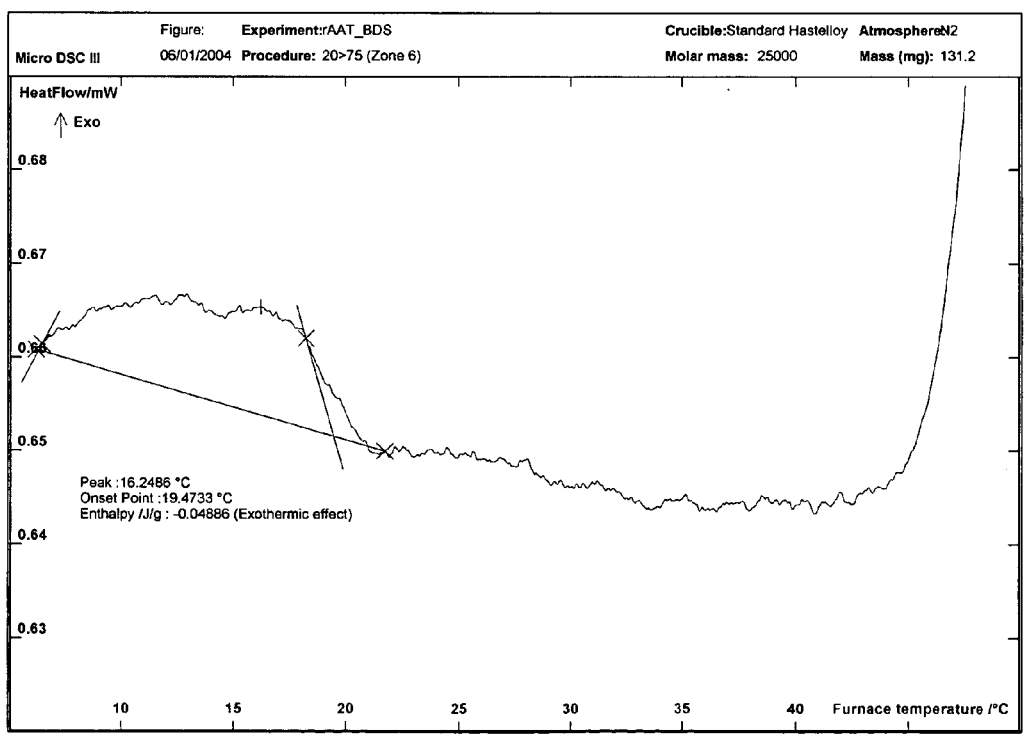
FIG. 18. A second cooling thermogram of a 50 mg/mL rAAT sample in BDS solution vs BDS as a reference.

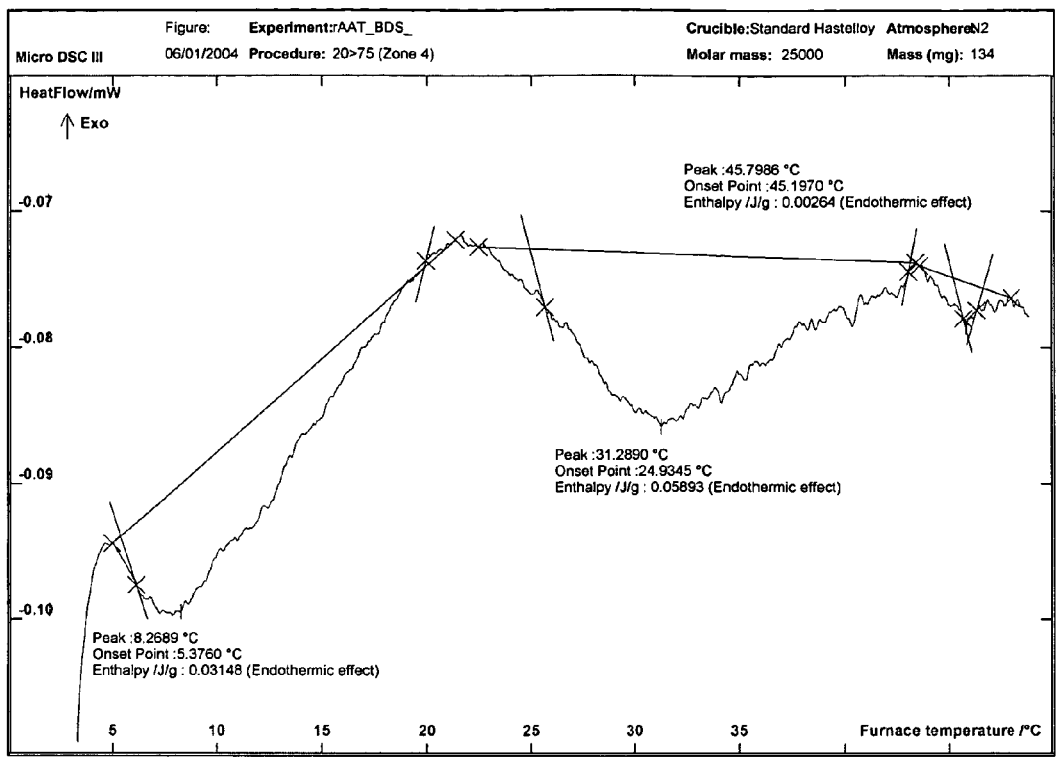
FIG. 19. A second heating thermogram of a 45 mg/mL rAAT sample in acetate solution vs acetate buffer as a reference.
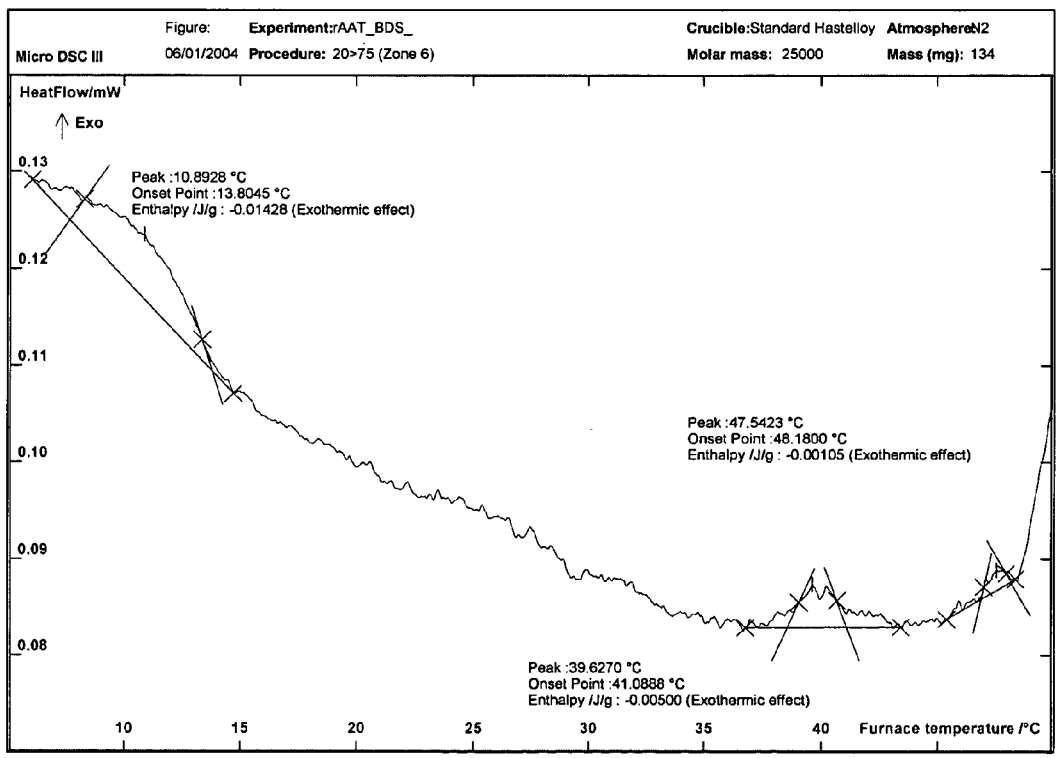
FIG. 20. A second cooling thermogram of a 45 mg/mL rAAT sample in acetate solution vs acetate buffer as a reference.

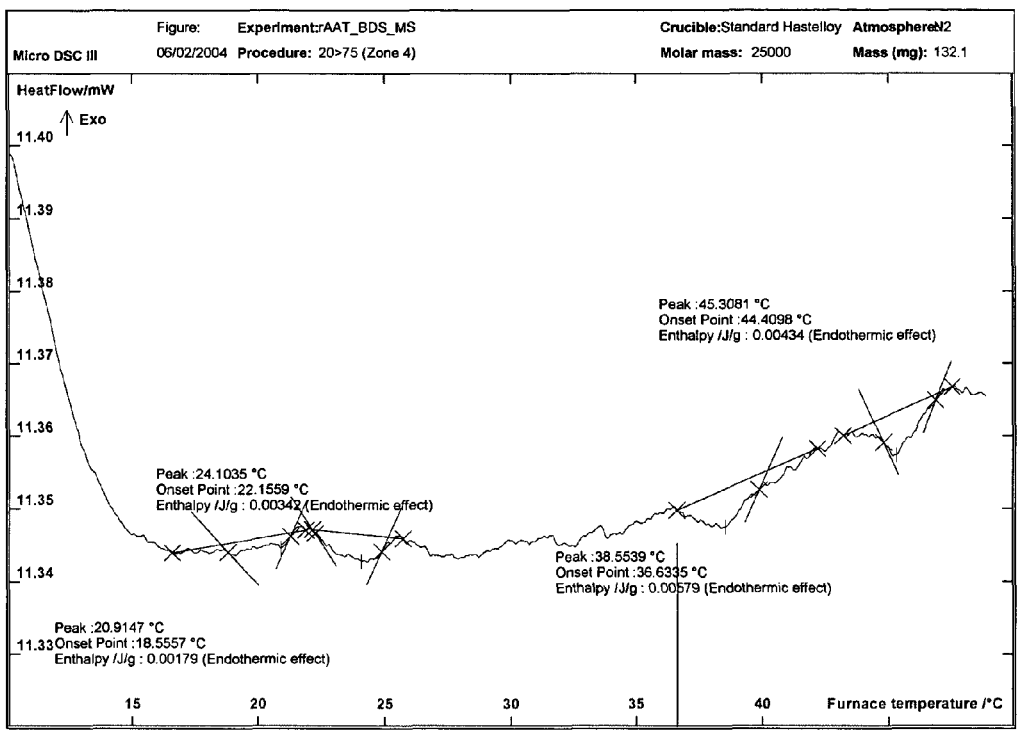
FIG. 21. A second heating thermogram of a 1 mg/mL rAAT sample in BDS solution vs BDS buffer as a reference. The rAAT sample resulted from dissolving rAAT 3 small spherical particles in BDS.

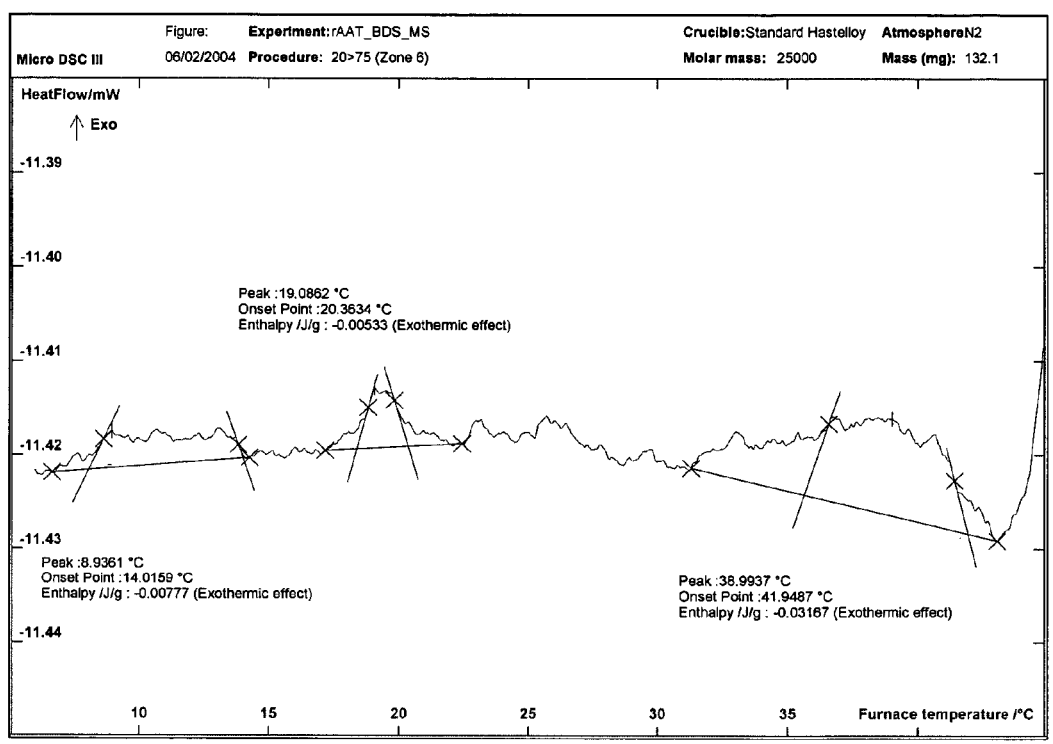
FIG. 22. A second cooling thermogram of a 1 mg/mL rAAT sample in BDS solution vs BDS buffer as a reference. The rAAT sample resulted from dissolving rAAT 3 small spherical particles in BDS.

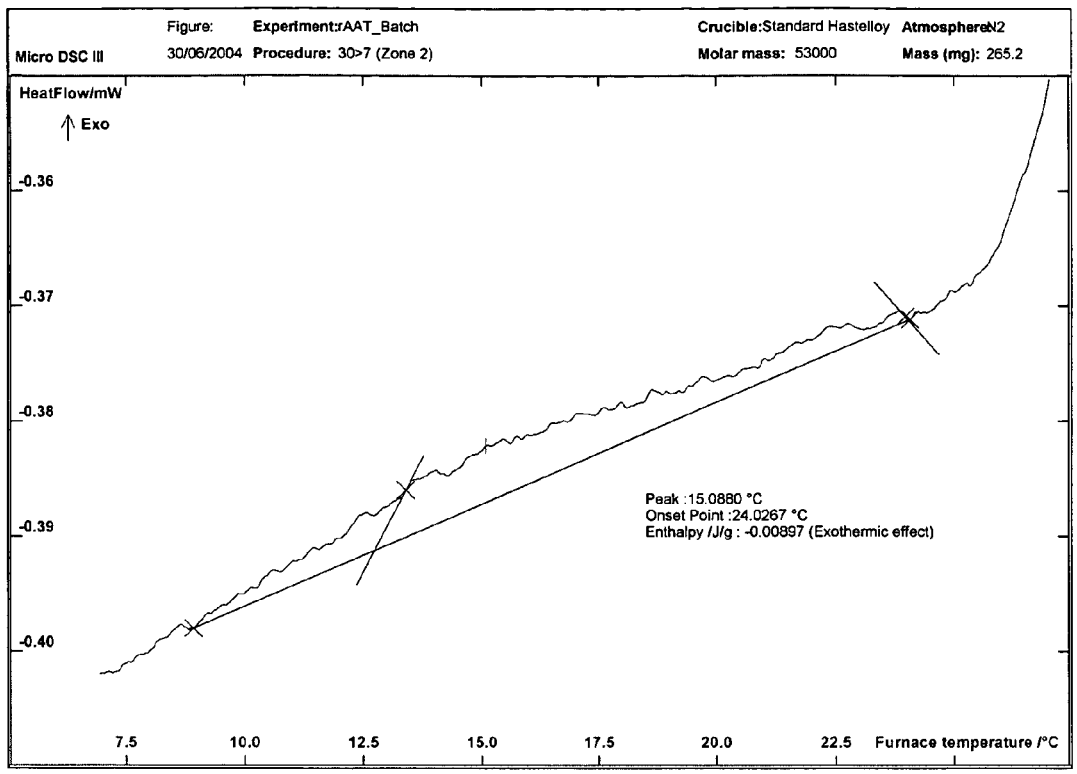
FIG. 23. First cooling thermogram of the small spherical particle fabrication batch.
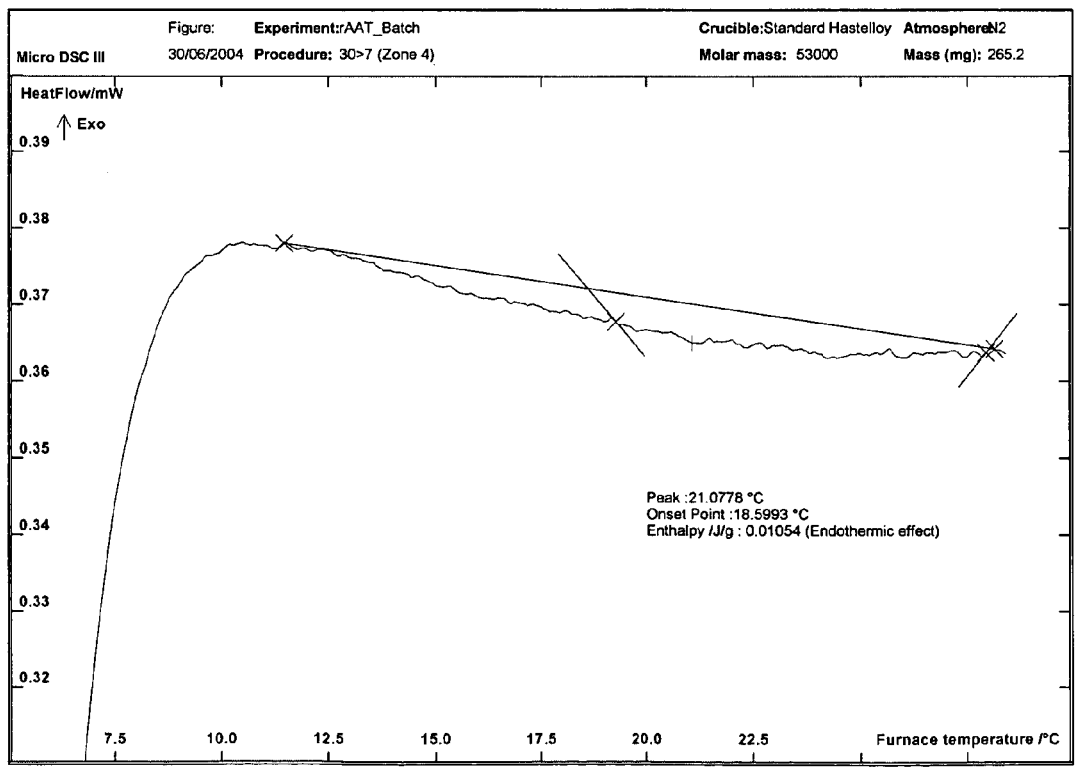
FIG. 24. First heating thermogram of the small spherical particle fabrication batch.

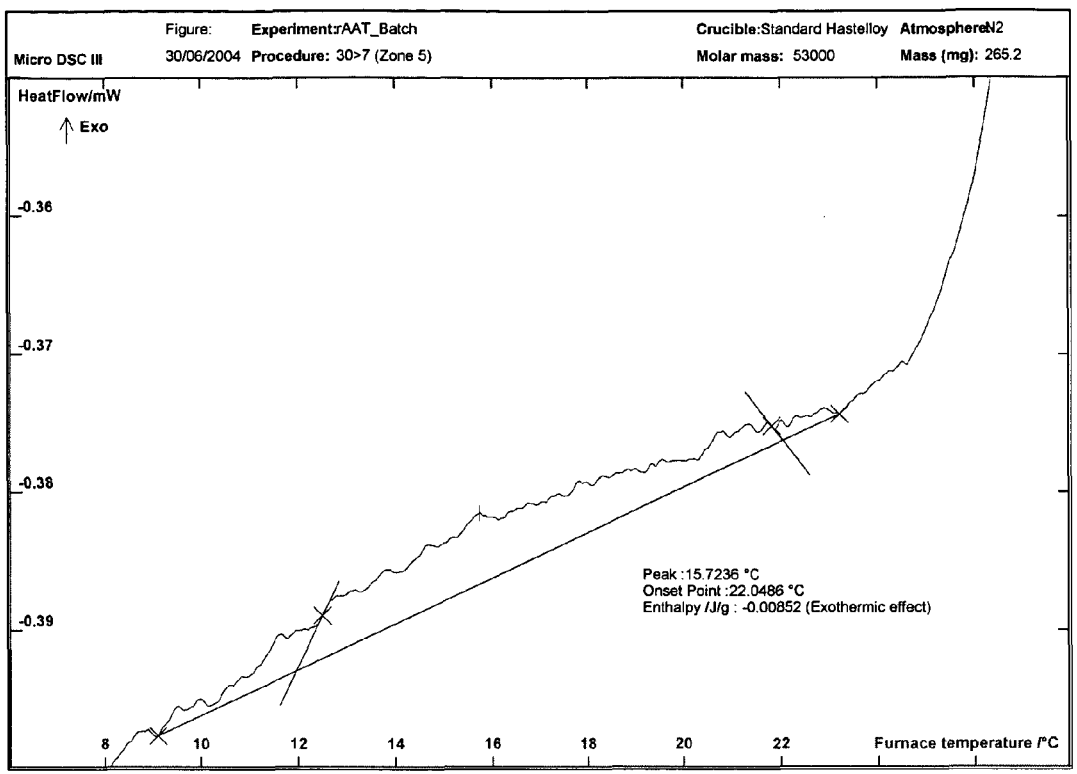
FIG. 25a. Second cooling thermogram of the small spherical particle fabrication batch.
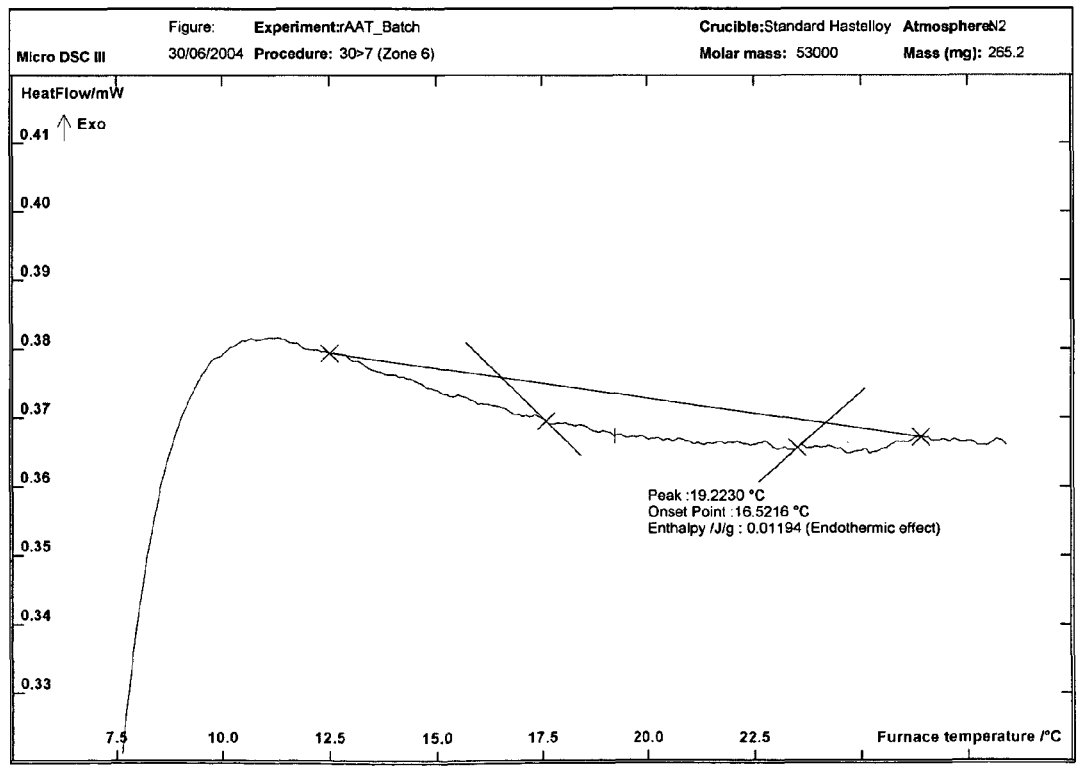
FIG. 25b. Second heating thermogram of the small spherical particle fabrication batch.

Scanning electron micrograph of hGH small spherical particles

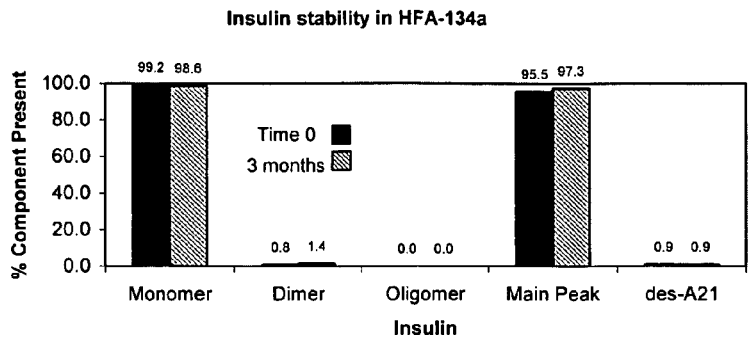

FIG. 28. Insulin in microsphere form maintains stability after storage in HFA 134a propellant.

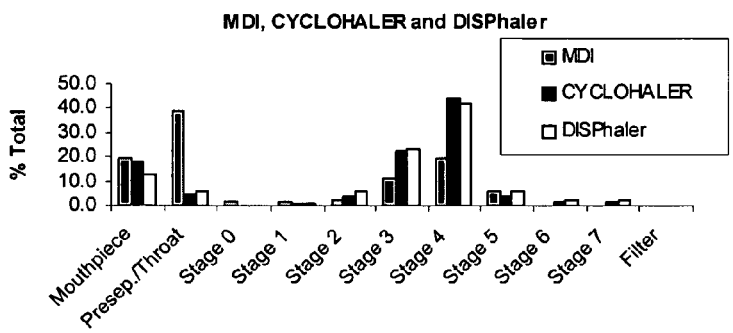

FIG. 29. The aerodynamic performance of insulin small spherical particles is compared using three different inhalation devices, a MDI, a Cyclohaler DPI, and a Disphaler DPI.

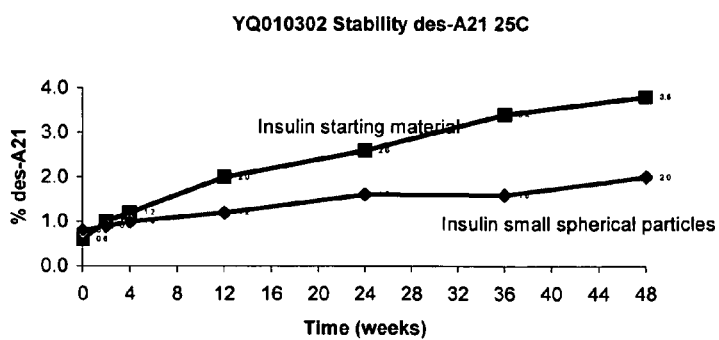

FIG. 30. At a storage temperature of 25°C, the percent A21-desamido insulin formation of the starting material is significantly greater compared to the insulin small spherical particles. This result indicates that the insulin small spherical particles are significantly more stable to chemical degradation than the starting material without the addition of stabilizing excipients.

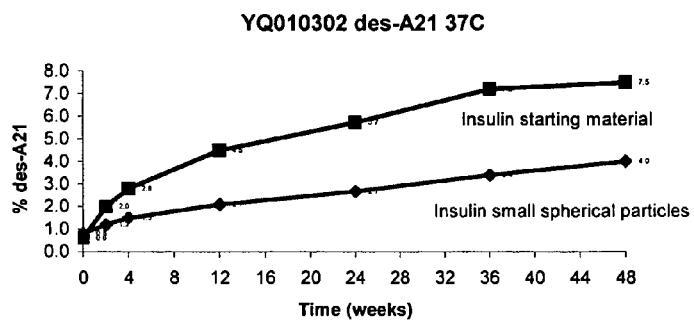

FIG. 31. At a storage temperature of 37°C, the percent A21-desamido insulin formation of the starting material is significantly greater compared to the insulin small spherical particles. This result indicates that the insulin small spherical particles are significantly more stable to chemical degradation than the starting material without the addition of stabilizing excipients.

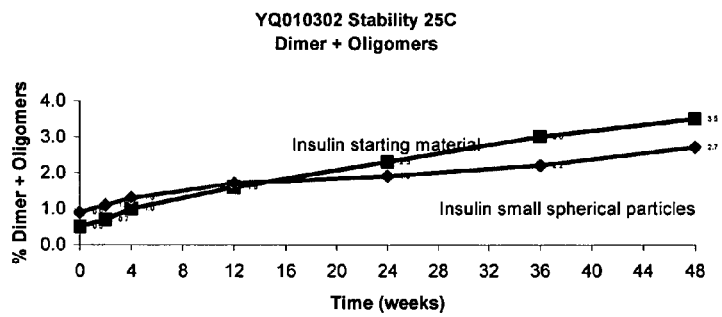

FIG. 32. At a storage temperature of 25°C, the percent insulin dimer and oligomer formation of the starting material is significantly greater compared to the insulin small spherical particles. This result indicates that the insulin small spherical particles are significantly more stable to chemical degradation than the starting material without the addition of stabilizing excipients.

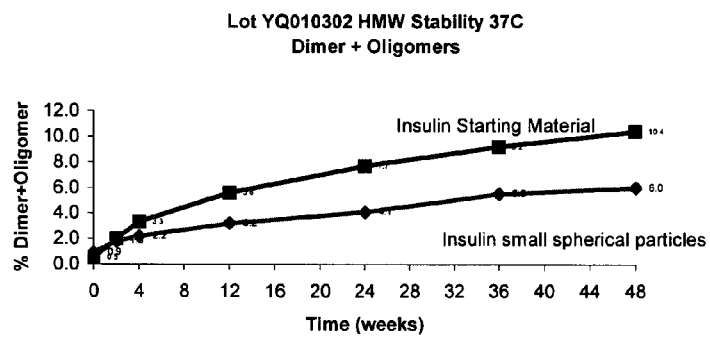

FIG. 33. At a storage temperature of 37°C, the percent insulin dimer and oligomer formation of the starting material is significantly greater compared to the insulin small spherical particles. This result indicates that the insulin small spherical particles are significantly more stable to chemical degradation than the starting material without the addition of stabilizing excipients.

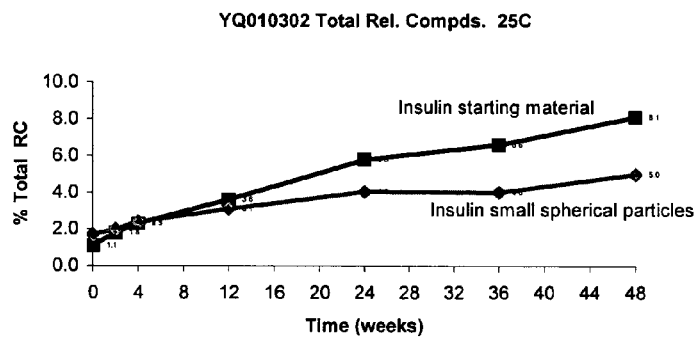

FIG. 34. At a storage temperature of 25°C, the percent insulin total related compound formation of the starting material is significantly greater compared to the insulin small spherical particles. This result indicates that the insulin small spherical particles are significantly more stable to chemical degradation than the starting material without the addition of stabilizing excipients.

FIG. 35. At a storage temperature of 37°C, the percent insulin total related compound formation of the starting material is significantly greater compared to the insulin small spherical particles. This result indicates that the insulin small spherical particles are significantly more stable to chemical degradation than the starting material without the addition of stabilizing excipients.

FIG. 36. Aerodynamic stability of insulin small spherical particles tested using a Cyclohaler DPI in the Andersen Cascade Impactor Device.

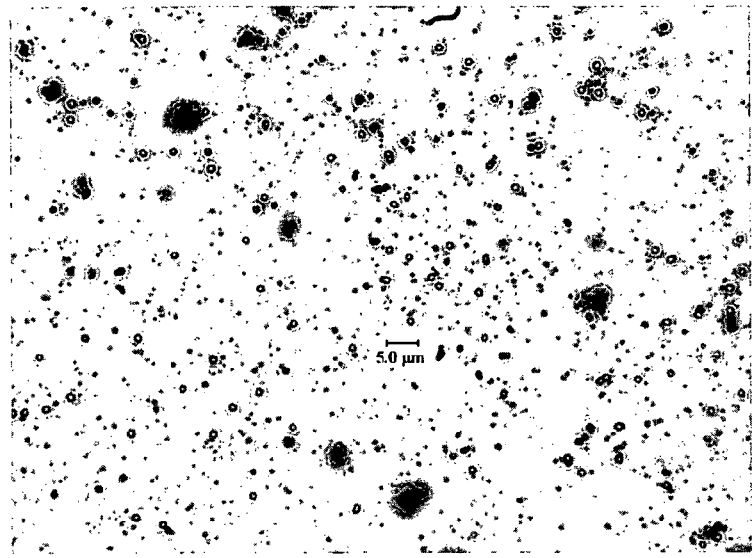
FIG. 37. Nikon light microscope, 100x oil immersion lense
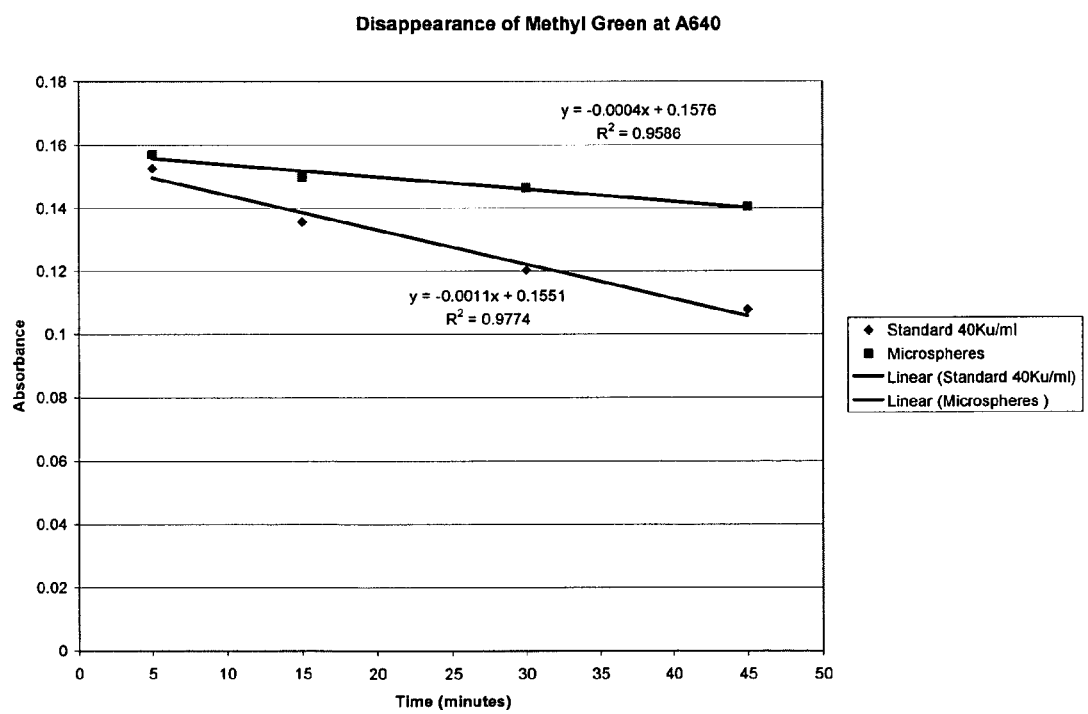
FIG. 38

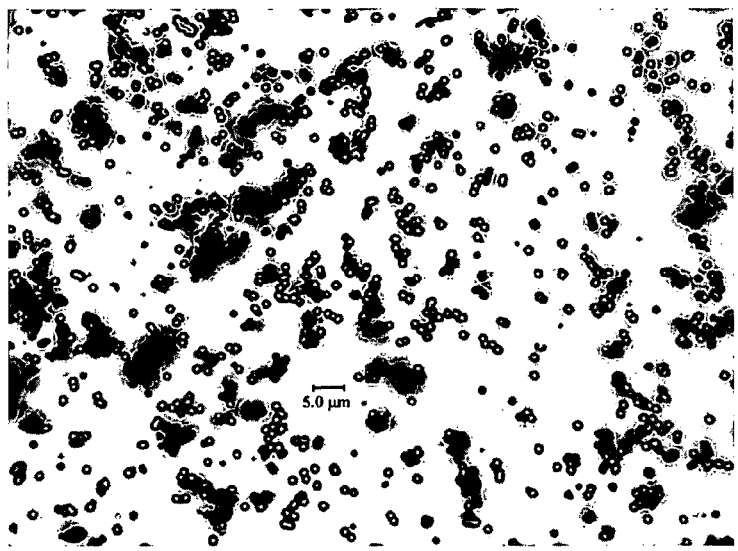
FIG. 39. Nikon light microscope, 100x oil immersion lense, dry powder sample
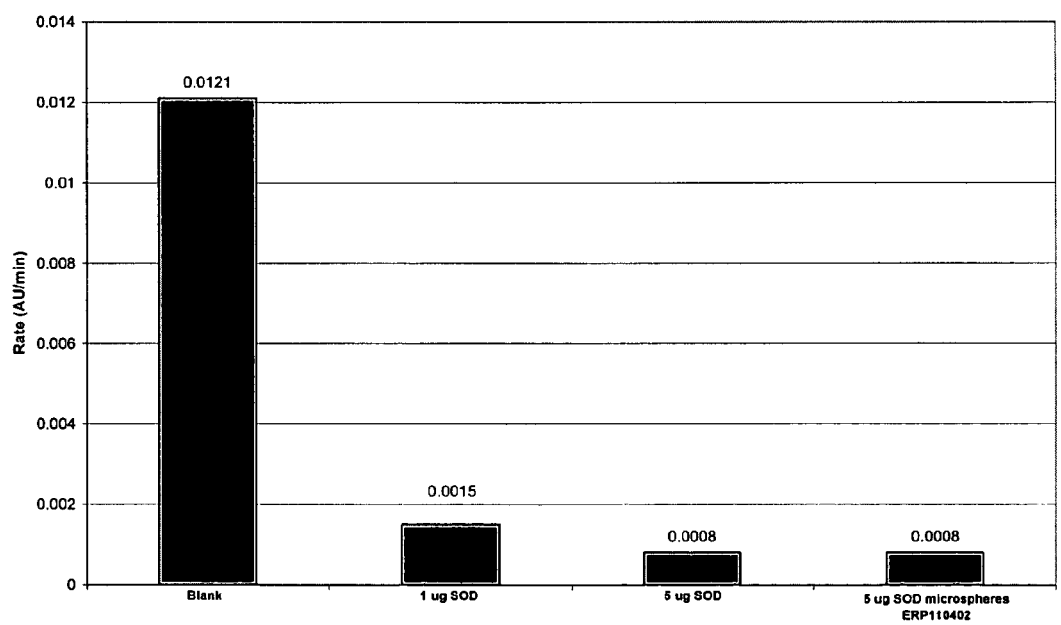
FIG. 40. Activity assay described in Worthington Biochemical Catalogue

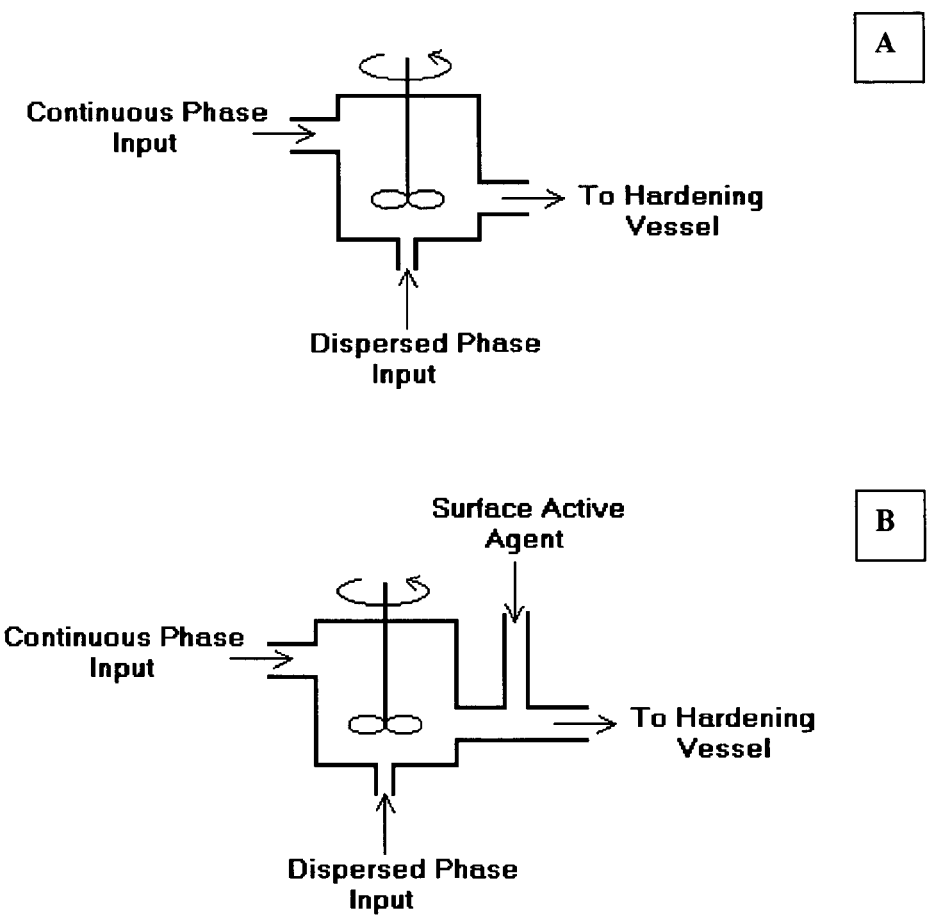
FIG. 41. Schematic illustration of the continuous emulsification reactor:
A) Surface active compound is added to the continuous phase or the dispersed phase before emulsification.
B) Surface active compound is added after emulsification

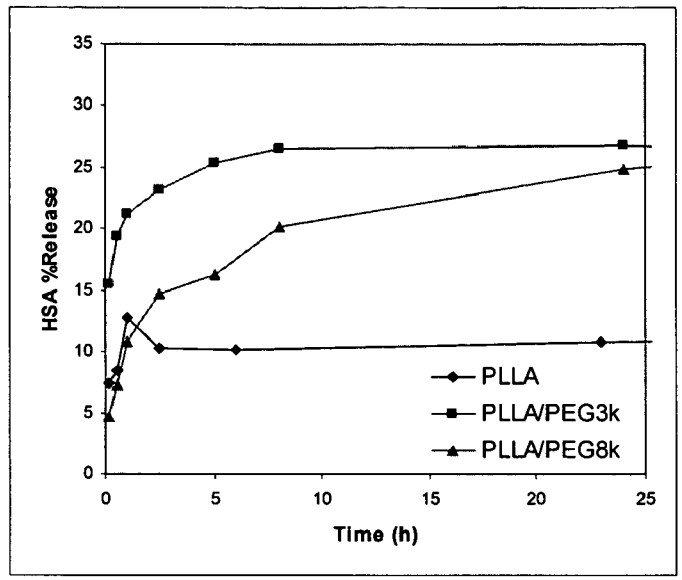
FIG. 42. Effect of PEG on the IVR profile of PLLA-encapsulated HSA particles (Example 32)
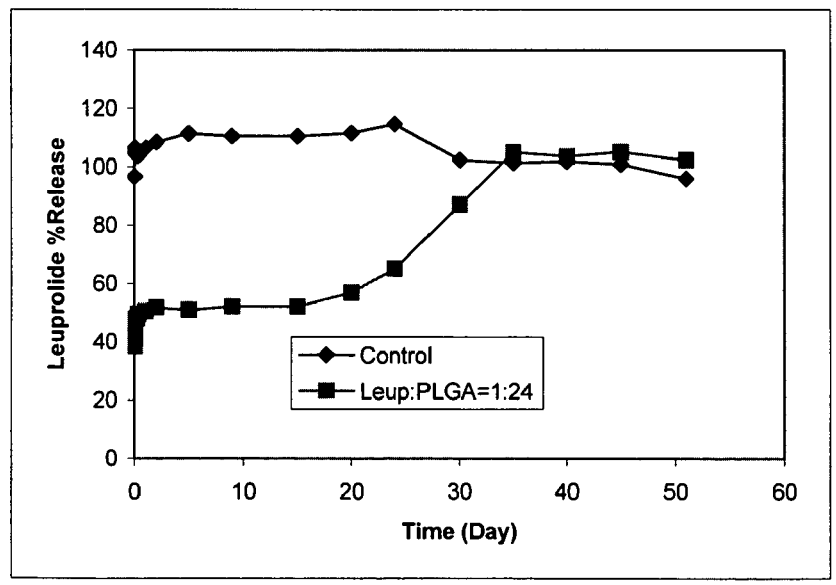
FIG. 43. IVR profile of PLGA encapsulated LDS small spherical particles (Example 33)

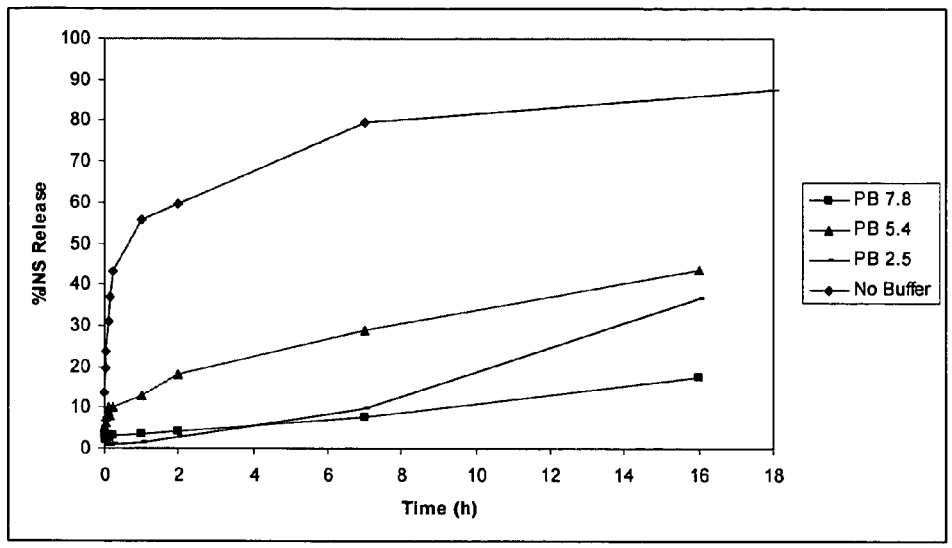
FIG. 44. Effect of pH of continuous phase on IVR profile of PLGA encapsulated insulin small spherical particles (Example 31)
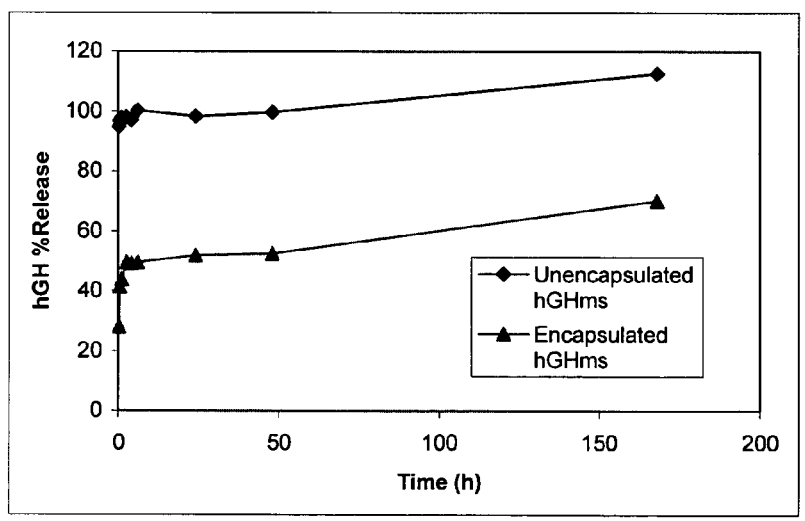
FIG. 45. IVR profile of PLGA encapsulated hGH small spherical particles (Example 34)

FIG. 46. Effect of the microencapsulation variables (pH of continuous phase and matrix material) on formation of INS dimers in encapsulated INSms (Example 35)

FIG. 47. Effect of the microencapsulation variables (pH of continuous phase and matrix material) on formation of HMW species in encapsulated INSms (Example 35)

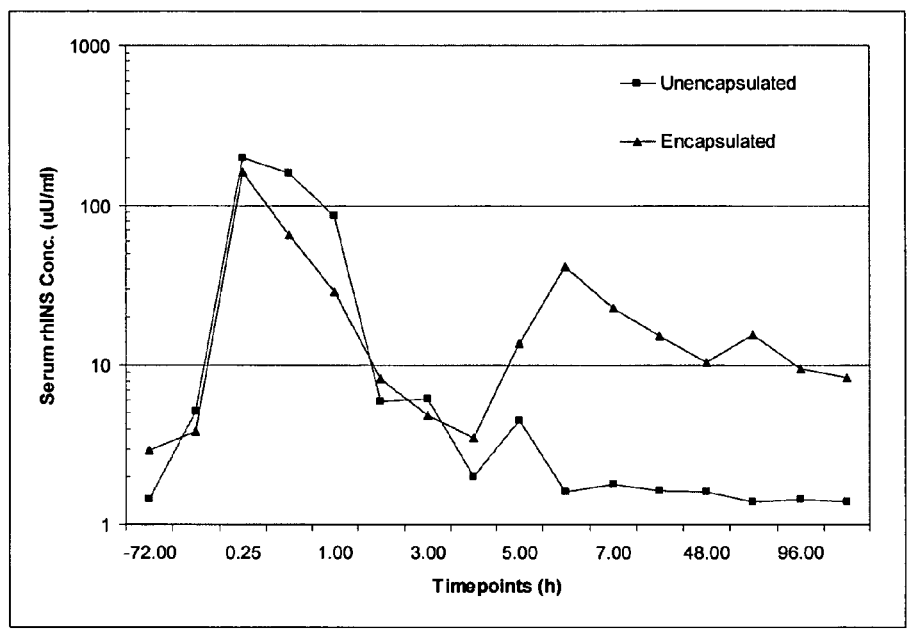
FIG. 48. In vivo release of recombinant human insulin from unencapsulated and encapsulated pre-fabricated insulin small spherical particles in rats (Example 36).

METHODS FOR FABRICATION, USES AND COMPOSITIONS OF SMALL SPHERICAL PARTICLES PREPARED BY CONTROLLED PHASE SEPARATION

CROSS-REFERENCE TO RELATED APPLICATION

This application claims priority to U.S. Provisional Application Ser. No. 60/488,712 filed Jul. 18, 2003, which is incorporated herein in its entirety by reference and made a part hereof.

FEDERALLY SPONSORED RESEARCH OR DEVELOPMENT

Not Applicable.

BACKGROUND OF THE INVENTION

1. Technical Field

The present invention relates to methods of production, methods of use, and compositions of small spherical particles of an active agent. In accordance with the method of production, the active agent is dissolved in an aqueous or aqueous-miscible solvent containing a dissolved phase-separation enhancing agent (PSEA) to form a solution in a single liquid phase. The solution is then subjected to a liquid-solid phase separation having the active agent comprising the solid phase and the PSEA and solvent comprising the liquid phase. The liquid-solid phase separation can be induced in numerous ways, such as changing the temperature of the solution to below the phase transition temperature of the system. The method is most suitable for forming small spherical particles of therapeutic agents which can be delivered to a subject in need of the therapeutic agent. The method is also most suitable for forming solid, small spherical particles of macromolecules, particularly macromolecules which are heat labile, such as proteins.

2. Background Art

Several techniques have been used in the past for the manufacture of biopolymer nano- and microparticles. Conventional techniques include spray drying and milling for particle formation and can be used to produce particles of 5 μm or less in size.

U.S. Pat. No. 5,654,010 and U.S. Pat. No. 5,667,808 describe the production of a solid form of recombinant human growth hormone, hGH, through complexation with zinc in order to create an amorphous complex, which is then micronized through an ultrasound nozzle and sprayed down in liquid nitrogen in order to freeze the droplets. The liquid nitrogen is then allowed to evaporate at a temperature of −80° C. and the resultant material is freeze-dried.

Microparticles, microspheres, and microcapsules are solid or semi-solid particles having a diameter of less than one millimeter, more preferably less than 100 microns and most preferably less than 10 microns, which can be formed of a variety of materials, including proteins, synthetic polymers, polysaccharides and combinations thereof. Microspheres have been used in many different applications, primarily separations, diagnostics, and drug delivery.

The most well known examples of microspheres used in separations techniques are those which are formed of polymers of either synthetic or natural origin, such as polyacrylamide, hydroxyapatite or agarose. In the controlled drug delivery area, molecules are often incorporated into or encapsulated within small spherical particles or incorporated into a monolithic matrix for subsequent release. A number of different techniques are routinely used to make these microspheres from synthetic polymers, natural polymers, proteins and polysaccharides, including phase separation, solvent evaporation, coascervation, emulsification, and spray drying. Generally the polymers form the supporting structure of these microspheres, and the drug of interest is incorporated into the polymer structure.

Particles prepared using lipids to encapsulate target drugs are currently available. Liposomes are spherical particles composed of a single or multiple phospholipid and/or cholesterol bilayers. Liposomes are 100 nanometer or greater in size and may carry a variety of water-soluble or lipid-soluble drugs. For example, lipids arranged in bilayer membranes surrounding multiple aqueous compartments to form particles may be used to encapsulate water soluble drugs for subsequent delivery as described in U.S. Pat. No. 5,422,120 to Sinil Kim.

Spherical beads have been commercially available as a tool for biochemists for many years. For example, antibodies conjugated to beads create relatively large particles that have binding specificity for particular ligands. Antibodies are routinely used to bind to receptors on the surface of a cell for cellular activation, are bound to a solid phase to form antibody-coated particles for immunoaffinity purification, and may be used to deliver a therapeutic agent that is slowly released over time, using tissue or tumor-specific antibodies conjugated to the particles to target the agent to the desired site.

There is an on-going need for development of new methods for making particles, particularly those that can be adapted for use in the drug delivery, separations and diagnostic areas. The most desirable particles from a utility standpoint would be small spherical particles that have the following characteristics: narrow size distribution, substantially spherical, substantially consisting of only the active agent, retention of the biochemical integrity and of the biological activity of the active agent. The particles should provide a suitable solid that would allow additional stabilization of the particles by coating or by microencapsulation. Further, the method of fabrication of the small spherical particles would have the following desirable characteristics: simple fabrication, an essentially aqueous process, high yield, and requiring no subsequent sieving.

SUMMARY OF THE INVENTION

The present invention relates to methods of production and methods of use of small spherical particles of an active agent. In accordance with the method, the active agent is dissolved in a solvent containing a dissolved phase-separation enhancing agent to form a solution that is a single liquid phase. The solvent is preferably an aqueous or aqueous miscible solvent. The solution is then subjected to a liquid-solid phase separation having the active agent comprising the solid phase and the PSEA and solvent comprising the liquid phase. The liquid-solid phase separation can be induced in numerous ways, such as changing the temperature of the solution to below the phase transition temperature of the solution.

In a preferred embodiment of the present invention, the method of subjecting the solution to a liquid-solid phase separation is by cooling the solution to below the phase transition temperature of the active agent in the solution. That temperature may be above or below the freezing point of the solution. For solutions in which the freezing point is above the phase transition temperature, the solution can include a freezing point depressing agent, such as polyethylene glycol or propylene glycol, to lower the freezing point of the solution to allow the phase separation in the solution to occur without freezing the solution.

The phase-separation enhancing agent of the present invention enhances or induces the liquid-solid phase separation of the active agent in the solution when the solution is subjected to the step of phase change in which the active agent solidifies to form a suspension of small spherical particles as a discontinuous phase while the phase-separation enhancing agent remains dissolved in the continuous phase. That is, the phase separating enhancing agent does not go through a change of phase, but the active agent does go through a phase change.

The method of producing the particles in the present invention may also include an additional step of controlling the liquid-solid phase separation of the particles to control the size and shape of the particles formed. Methods of controlling the phase-separation include control of the ionic strength, the pH, the concentration of the phase-separation enhancing agent, the concentration of the active agent in the solution, or controlling the rate of change in temperature of the solution, the control of these being either before the phase-separation or a change of any or several of these in order to induce the phase-separation.

In a preferred embodiment of the present invention, the small spherical particles are separated from the PSEA in the continuous phase after particle formation. In yet another preferred embodiment, the method of separation is by washing the solution containing the particles with a liquid medium in which the active agent is not soluble in the liquid medium while the phase-separation enhancing agent is soluble in the liquid medium. The liquid washing medium may contain an agent which reduces the solubility of the active agent in the liquid medium. The liquid washing medium may also contain one or more excipients. The excipient may act as a stabilizer for the small spherical particles or for the active agent or the carrier agent. The excipient may also imbue the active agent or the particle with additional characteristics such as controlled release of the active agent from the particles or modified permeation of the active agent through biological tissues.

In another preferred embodiment, while the small particles do not include the PSEA, they may be harvested in the presence of the PSEA phase for subsequent processing steps prior to separation from the PSEA phase.

In another preferred embodiment, the solution is an aqueous solution comprising an aqueous or aqueous-miscible solvent.

The active agent of the present invention is preferably a pharmaceutically active agent, which can be a therapeutic agent, a diagnostic agent, a cosmetic, a nutritional supplement, or a pesticide. In a preferred embodiment of the present invention, the active agent is a macromolecule, such as a protein, a polypeptide, a carbohydrate, a polynucleotide, or a nucleic acid. In yet another preferred embodiment, the particles containing the active agent are suitable for in vivo delivery to a subject in need of the agent by a suitable route, such as parenteral injection, topical, oral, rectal, nasal, pulmonary, vaginal, buccal, sublingual, transdermal, transmucosal, ocular, intraocular or otic.

BRIEF DESCRIPTION OF THE DRAWINGS

FIG. 2 is a cooling temperature profile.
FIG. 4 is an HPLC analysis showing overall maintenance of chemical stability of insulin when prepared into small spherical particles.
FIGS. 5a and 5b are schematics demonstrating batch-to-batch reproducibility.
FIG. 6 is a schematic demonstrating batch-to-batch reproducibility.
FIG. 7 is a schematic diagram of the continuous flow through process for making insulin small spherical particles in Example 3.
FIG. 8 is a scanning electron micrograph (at 10 Kv and 6260× magnification) of the insulin small spherical particles produced by the continuous flow through process in Example 3.
FIG. 9 is an HPLC chromatograph of dissolved insulin small spherical particles prepared by the continuous flow through process in Example 3.
FIGS. 10a-10d demonstrate the effect of sodium chloride on insulin solubility.
FIGS. 10e-10h demonstrate the effect of different salts on insulin solubility.
FIG. 10i is a Raman spectra of raw material insulin, insulin released from small spherical particles and insulin in small spherical particles.
FIG. 11 is an Andersen Cascade Impactor results for radio-labeled insulin of Example 10.
FIG. 12 is a bar graph of P/I ratios for Example 8.
FIG. 13 is a scintigraphic image of a lung from Example 8.
FIG. 14a is a circular dichroism (CD) plot for alpha-1-antitrypsin (AAT).
FIG. 14b is a plot of activity against storage time at room temperature in Example 17.
FIG. 14c is a plot of activity against storage time at 4° C. in Example 17.
FIGS. 15-25b are DSC plots.
FIG. 26 is a plot of TSI Corporation Aerosizer particle size data.
FIG. 27 is a SEM of human growth hormone (hGH) small spherical particles.
FIG. 28 is a chart showing insulin stability data in HFA-134a.
FIG. 29 is a chart comparing aerodynamic performance of Insulin using three inhalation devices.
FIG. 30 is a chart of stability data of Insulin small spherical particles compared to Insulin starting material stored at 25° C.
FIG. 31 is a chart of stability data of Insulin small spherical particles compared to Insulin starting material stored at 37° C.
FIG. 32 is a chart of stability data of Insulin small spherical particles compared to Insulin starting material stored at 25° C.
FIG. 33 is a chart of stability data of Insulin small spherical particles compared to Insulin starting material stored at 37° C.
FIG. 34 is a chart of stability data of Insulin small spherical particles compared to Insulin starting material stored at 25° C.
FIG. 35 is a chart of stability data of Insulin small spherical particles compared to Insulin starting material stored at 37° C.
FIG. 36 is a bar graph of insulin aerodynamic stability using a Cyclohaler DPI.
FIG. 37 is a light micrograph of DNase small spherical particles.
FIG. 38 is a chart of enzymatic activity of DNase.
FIG. 39 is a light micrograph of SOD small spherical particles.
FIG. 40 is a chart of enzymatic data for SOD small spherical particles.

FIGS. 41A-B are schematic illustrations of the continuous emulsification reactor, where FIG. 41A is a schematic illustration of the continuous emulsification reactor when surface active compound added to the continuous phase or the dispersed phase before emulsification, and FIG. 41B is a schematic illustration of the continuous emulsification reactor when the surface active compound is added after emulsification.

FIG. 42 illustrates the effect of PEG on the IVR profile of PLLA-encapsulated HSA particles (Example 32).

FIG. 43 illustrates the IVR profile of PLGA encapsulated LDS small spherical particles (Example 33).

FIG. 44 illustrates the effect of pH of continuous phase on IVR profile of PLGA encapsulated insulin small spherical particles (Example 31).

FIG. 45 illustrates the IVR profile of PLGA encapsulated hGH small spherical particles (Example 34).

FIG. 46 illustrates the effect of the microencapsulation variables (pH of continuous phase and matrix material) on formation of INS dimers in encapsulated INSms (Example 35).

FIG. 47 illustrates the effect of the microencapsulation variables (pH of continuous phase and matrix material) on formation of HMW species in encapsulated INSms (Example 35).

FIG. 48 illustrates in-vivo release of recombinant human insulin from unencapsulated and encapsulated pre-fabricated insulin small spherical particles in rats (Example 36).

DETAILED DESCRIPTION OF THE INVENTION

Figure 1:
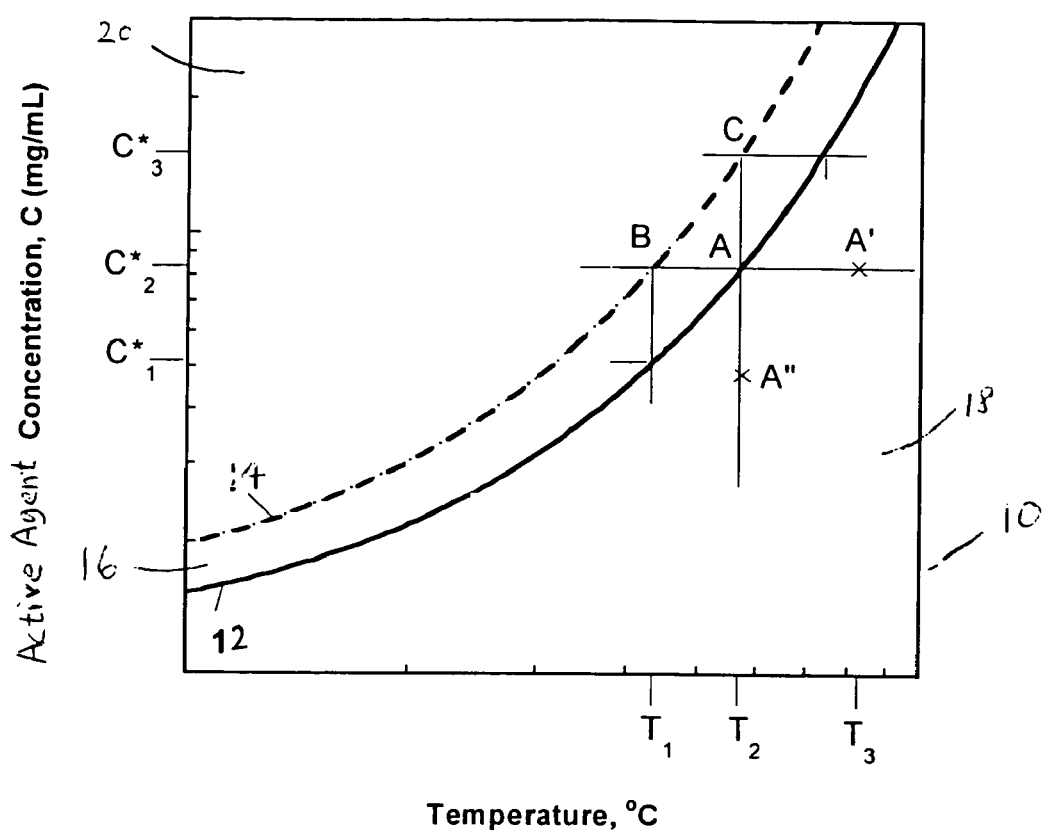
FIG. 1 is a two-dimensional phase diagram plotting active agent concentration against temperature.

The present invention is susceptible to embodiments in many different forms. Preferred embodiments of the invention are disclosed with the understanding that the present disclosure is to be considered as exemplifications of the principles of the invention and are not intended to limit the broad aspects of the invention to the embodiments illustrated.

The present invention is related to methods of production and methods of use and composition of small spherical particles of an active agent. In accordance with the method of production, the active agent is dissolved in a solvent containing a dissolved phase-separation enhancing agent to form a solution that is a single liquid continuous phase. The solvent is preferably an aqueous or aqueous-miscible solvent. The solution is then subjected to a phase change, for example, by lowering the temperature of the solution to below the phase transition temperature of the active agent, whereby the active agent goes through a liquid-solid phase separation to form a suspension of small spherical particles constituting a discontinuous phase while the phase-separation enhancing agent remains in the continuous phase.

Phases:

The Continuous Phase

The method of the present invention of preparing small spherical particles of an active agent begins with providing a solution having the active agent and a phase-separation enhancing agent dissolved in a first solvent in a single liquid phase. The solution can be an organic system comprising an organic solvent or a mixture of miscible organic solvents. The solution can also be an aqueous-based solution comprising an aqueous medium or an aqueous-miscible organic solvent or a mixture of aqueous-miscible organic solvents or combinations thereof. The aqueous medium can be water, normal saline, buffered solutions, buffered saline, and the like. Suitable aqueous-miscible organic solvents include, but are not limited to, N-methyl-2-pyrrolidinone (N-methyl-2-pyrrolidone), 2-pyrrolidinone (2-pyrrolidone), 1,3-dimethyl-2-imidazolidinone (DMI), dimethylsulfoxide, dimethylacetamide, acetic acid, lactic acid, acetone, methyl ethyl ketone, acetonitrile, methanol, ethanol, isopropanol, 3-pentanol, n-propanol, benzyl alcohol, glycerol, tetrahydrofuran (THF), polyethylene glycol (PEG), PEG-4, PEG-8, PEG-9, PEG-12, PEG-14, PEG-16, PEG-120, PEG-75, PEG-150, polyethylene glycol esters, PEG-4 dilaurate, PEG-20 dilaurate, PEG-6 isostearate, PEG-8 palmitostearate, PEG-150 palmitostearate, polyethylene glycol sorbitans, PEG-20 sorbitan isostearate, polyethylene glycol monoalkyl ethers, PEG-3 dimethyl ether, PEG-4 dimethyl ether, polypropylene glycol (PPG), polypropylene alginate, PPG-10 butanediol, PPG-10 methyl glucose ether, PPG-20 methyl glucose ether, PPG-15 stearyl ether, propylene glycol dicaprylate/dicaprate, propylene glycol laurate, and glycofurol (tetrahydrofurfuryl alcohol polyethylene glycol ether), alkanes including propane, butane, pentane, hexane, heptane, octane, nonane, decane, or a combination thereof.

The single continuous phase can be prepared by first providing a solution of the phase-separation enhancing agent, which is either soluble in or miscible with the first solvent. This is followed by adding the active agent to the solution. The active agent may be added directly to the solution, or the active agent may first be dissolved in a second solvent and then together added to the solution. The second solvent can be the same solvent as the first solvent, or it can be another solvent selected from the list above and which is miscible with the solution. It is preferred that the agent is added to the solution at an ambient temperature or lower, which is important particularly for heat labile molecules, such as certain proteins. What is meant by "ambient temperature" is a temperature of around room temperature of about 20° C. to about 40° C. However, the system can also be heated to increase the solubility of the active agent in the system as long as heating does not cause significant reduction in the activity of the agent.

The Phase-Separation Enhancing Agent

The phase-separation enhancing agent (PSEA) of the present invention enhances or induces the liquid-solid phase separation of the active agent from the solution when the solution is subjected to the step of phase separation in which the active agent becomes solid or semi-solid to form a suspension of small spherical particles as a discontinuous phase while the phase-separation enhancing agent remains dissolved in the continuous phase. The phase-separation enhancing agent reduces the solubility of the active agent when the solution is brought to the phase separation conditions. Suitable phase-separation enhancing agents include, but are not limited to, polymers or mixtures of polymers that are soluble or miscible with the solution. Examples of suitable polymers include linear or branched polymers. These polymers can be water soluble, semi-water soluble, water-miscible, or insoluble.

In a preferred form of the invention, the phase-separation enhancing agent is water soluble or water miscible. Types of polymers that may be used include carbohydrate-based polymers, polyaliphatic alcohols, poly(vinyl) polymers, polyacrylic acids, polyorganic acids, polyamino acids, co-polymers and block co-polymers (e.g., poloxamers such as Pluronics F127 or F68), tert-polymers, polyethers, naturally occurring polymers, polyimides, surfactants, polyesters, branched and cyclo-polymers, and polyaldehydes.

Preferred polymers are ones that are acceptable as pharmaceutical additives for the intended route of administration of the active agent particles. Preferred polymers are pharmaceutically acceptable additives such as polyethylene glycol (PEG) of various molecular weights, such as PEG 200, PEG 300, PEG 3350, PEG 8000, PEG 10000, PEG 20000, etc. and poloxamers such as Pluronics F127 or Pluronics F68. Yet another preferred polymer is polyvinylpyrrolidone (PVP). Yet another preferred polymer is hydroxyethylstarch. Other amphiphilic polymers can also be used alone or in combinations. The phase-separation enhancing agent can also be a non-polymer such as a mixture of propylene glycol and ethanol.

Liquid-Solid Phase Separation

A liquid-solid phase separation of the active agent in the solution can be induced by any method known in the art, such as change in temperature, change in pressure, change in pH, change in ionic strength of the solution, change in the concentration of the active agent, change in the concentration of the phase-separation enhancing agent, change in osmolality of the solution, combinations of these, and the like.

In a preferred embodiment of the present invention, the phase change is a temperature-induced phase change by lowering the temperature below the phase transition temperature of the active agent in the solution.

FIG. 1 is a two-dimensional phase diagram 10 for the solution containing solvent, a PSEA and an active agent. The diagram plots the active agent concentration against the temperature of the solution. The concentration of the PSEA is held constant.

The diagram has a saturation curve 12; a supersaturation curve 14; a metastable area 16 therebetween; a first area 18 below the saturation curve where the system is in a homogenous, single liquid phase where all components are in the liquid phase; and a second area 20 above the supersaturation curve where the system is a two-phase system having a solid phase of the active agent and a liquid phase of the PSEA and solvent. The phase diagram is helpful in determining the temperature of the system and the relative concentration of components in the pure liquid phase, the liquid-solid phase and the conditions surrounding the transition between these two phases.

As disclosed herein, preparation of small spherical particles of the active agent principally involves cooling from an undersaturated solution (point A') reaching saturation in point A where the solution is in equilibrium with any solid phase that may be present. On further cooling, a state is reached where the solution contains more active agent than that corresponding to the equilibrium solubility at the given temperature; the solution thus becomes supersaturated. Spontaneous formation of the solid phase does not occur until point B is reached. The point B is a point on the boundary of the metastable zone. The metastable zone width can be expressed either by the maximum attainable undercooling $\Delta T_{max} = T_2 - T_1$ or by the supersaturation $\Delta C_{max} = C^*_2 - C^*_1$. These two expressions are thermodynamically equivalent:

$$\Delta C_{max} = C^*_2 - C^*_1 = \int_{T_1}^{T_2} \left(\frac{\partial C^*}{\partial T}\right) dT \cong \Delta T_{max} \left(\frac{dC^*}{dT}\right)$$

The path A'-A-B represents a polythermal method of preparing a metastable solution. In an isothermal process the starting point would be A''. By increasing the concentration at constant temperature, saturation will again be achieved at point A. An isothermal increase in concentration (by solvent evaporation or by seeding/addition of the active agent, for instance) to point C will cause the solution to move into the metastable region until the metastability limit is again reached. When the metastable limit is exceeded the solution becomes unstable and a spontaneous formation of the solid phase immediately occurs.

The value $(\Delta C_{max})_T = C^*_3 - C^*_2$ obtained isothermally can be different from the corresponding value of $\Delta T_{max} = T_3 - T_2$ obtained polythermally. As the boundary of the metastable zone is approached, the time necessary for the solid particle formation decreases until the metastable limit is reached.

In the polythermal process, the rate of cooling is done at a controlled rate to control the size and shape of the particles. What is meant by a controlled rate is about 0.2° C./minute to about 50° C./minute, and more preferably from 0.2° C./minute to 30° C./minute. The rate of change can be at a constant or linear rate, a non-linear rate, intermittent, or a programmed rate (having multiple phase cycles).

The particles can be separated from the PSEA in the solution and purified by washing as will be discussed below.

The present invention contemplates adjusting the concentration of the active agent, the concentration of the PSEA, the temperature or any combination of these to cause a phase change where the active agent goes from a liquid state to a solid state while the PSEA and solvent do not go through a phase change and remain as liquids. It is also contemplated changing the pH, the ionic strength, the osmolality and the like to enhance, promote, control or suppress the phase change. For solutions in which the freezing point is relatively high, or the freezing point is above the phase transition temperature, the solutions can include a freezing point depressing agent, such as propylene glycol, sucrose, ethylene glycol, alcohols (e.g., ethanol, methanol) or aqueous mixtures of freezing-point depression agents to lower the freezing point of the system to allow the phase change in the system without freezing the system. The process can also be carried out such that the temperature is reduced below the freezing point of the system. The process described herein is particularly suitable for molecules that are heat labile (e.g., proteins).

Optional Excipients

The particles of the present invention may include one or more excipients. The excipient may imbue the active agent or the particles with additional characteristics such as increased stability of the particles or of the active agents or of the carrier agents, controlled release of the active agent from the particles, or modified permeation of the active agent through biological tissues. Suitable excipients include, but are not limited to, carbohydrates (e.g., trehalose, sucrose, mannitol), cations (e.g., $Zn^{2+}$, $Mg^{2+}$, $Ca^{2+}$), anions (e.g. $SO_4^{2-}$), amino acids (e.g., glycine), lipids, phospholipids, fatty acids, surfactants, triglycerides, bile acids or their salts (e.g., cholate or its salts, such as sodium cholate; deoxycholic acid or its salts), fatty acid esters, and polymers present at levels below their functioning as PSEA's. When an excipient is used, the excipient does not significantly affect the phase diagram of the solution.

Separating and Washing the Particles

In a preferred embodiment of the present invention, the small spherical particles are harvested by separating them from the phase-separation enhancing agent in the solution. In yet another preferred embodiment, the method of separation is by washing the solution containing the small spherical particles with a liquid medium in which the active agent is not soluble in the liquid medium while the phase-separation enhancing agent is soluble in the liquid medium. Some methods of washing may be by diafiltration or by centrifugation. The liquid medium can be an aqueous medium or an organic solvent. For active agents with low aqueous solubility, the liquid medium can be an aqueous medium or an aqueous medium containing agents that reduce the aqueous solubility of the active agent, such as divalent cations. For active agents with high aqueous solubility, such as many proteins, an organic solvent or an aqueous solvent containing a protein-precipitating agent such as ammonium sulfate may be used.

Examples of suitable organic solvents for use as the liquid medium include those organic solvents specified above as suitable for the continuous phase, and more preferably methylene chloride, chloroform, acetonitrile, ethylacetate, methanol, ethanol, pentane, and the like.

It is also contemplated to use mixtures of any of these solvents. One preferred blend is methylene chloride or a 1:1 mixture of methylene chloride and acetone. It is preferred that the liquid medium has a low boiling point for easy removal by, for example, lyophilization, evaporation, or drying.

The liquid medium can also be a supercritical fluid, such as liquid carbon dioxide or a fluid near its supercritical point. Supercritical fluids can be suitable solvents for the phase-separation enhancing agents, particularly some polymers, but are nonsolvents for protein particles. Supercritical fluids can be used by themselves or with a cosolvent. The following supercritical fluids can be used: liquid $CO_2$, ethane, or xenon. Potential cosolvents can be acetontitrile, dichloromethane, ethanol, methanol, water, or 2-propanol.

The liquid medium used to separate the small spherical particles from the PSEA described herein, may contain an agent which reduces the solubility of the active agent in the liquid medium. It is most desirable that the particles exhibit minimal solubility in the liquid medium to maximize the yield of the particles. For some proteins, such as insulin and human growth hormone, the decrease in solubility can be achieved by the adding of divalent cations, such as $Zn^{2+}$ to the protein. Other ions that can be used to form complexes include, but are not limited to, $Ca^{2+}$, $Cu^{2+}$, $Fe^{2+}$, $Fe^{3+}$, and the like.

The solubility of the insulin-Zn or growth hormone-Zn complexes are sufficiently low to allow diafiltration of the complex in an aqueous solution.

The liquid medium may also contain one or more excipients which may imbue the active agent or the particles with additional characteristics such as increased stability of the particles and/or of the active or carrier agents, controlled release of the active agent from the particles, or modified permeation of the active agent through biological tissues as discussed previously.

In another form of the invention, the small spherical particles are not separated from the PSEA containing solution.

Aqueous-Based Process

In another preferred embodiment, the fabrication process of the present system is of an aqueous system including an aqueous or an aqueous-miscible solvent. Examples of suitable aqueous-miscible solvents include, but are not limited to, those identified above for the continuous phase. One advantage of using an aqueous-based process is that the solution can be buffered and can contain excipients that provide biochemical stabilization to protect the active agents, such as proteins.

The Active Agent

The active agent of the present invention is preferably a pharmaceutically active agent, which can be a therapeutic agent, a diagnostic agent, a cosmetic, a nutritional supplement, or a pesticide.

The therapeutic agent can be a biologic, which includes but is not limited to proteins, polypeptides, carbohydrates, polynucleotides, and nucleic acids. The protein can be an antibody, which can be polyclonal or monoclonal. The therapeutic can be a low molecular weight molecule. In addition, the therapeutic agents can be selected from a variety of known pharmaceuticals such as, but are not limited to: analgesics, anesthetics, analeptics, adrenergic agents, adrenergic blocking agents, adrenolytics, adrenocorticoids, adrenomimetics, anticholinergic agents, anticholinesterases, anticonvulsants, alkylating agents, alkaloids, allosteric inhibitors, anabolic steroids, anorexiants, antacids, antidiarrheals, antidotes, antifolics, antipyretics, antirheumatic agents, psychotherapeutic agents, neural blocking agents, anti-inflammatory agents, antihelmintics, anti-arrhythmic agents, antibiotics, anticoagulants, antidepressants, antidiabetic agents, antiepileptics, antifungals, antihistamines, antihypertensive agents, antimuscarinic agents, antimycobacterial agents, antimalarials, antiseptics, antineoplastic agents, antiprotozoal agents, immunosuppressants, immunostimulants, antithyroid agents, antiviral agents, anxiolytic sedatives, astringents, beta-adrenoceptor blocking agents, contrast media, corticosteroids, cough suppressants, diagnostic agents, diagnostic imaging agents, diuretics, dopaminergics, hemostatics, hematological agents, hemoglobin modifiers, hormones, hypnotics, immunological agents, antihyperlipidemic and other lipid regulating agents, muscarinics, muscle relaxants, parasympathomimetics, parathyroid hormone, calcitonin, prostaglandins, radio-pharmaceuticals, sedatives, sex hormones, anti-allergic agents, stimulants, sympathomimetics, thyroid agents, vasodilators, vaccines, vitamins, and xanthines. Antineoplastic, or anticancer agents, include but are not limited to paclitaxel and derivative compounds, and other antineoplastics selected from the group consisting of alkaloids, antimetabolites, enzyme inhibitors, alkylating agents and antibiotics.

A cosmetic agent is any active ingredient capable of having a cosmetic activity. Examples of these active ingredients can be, inter alia, emollients, humectants, free radical-inhibiting agents, anti-inflammatories, vitamins, depigmenting agents, anti-acne agents, antiseborrhoeics, keratolytics, slimming agents, skin coloring agents and sunscreen agents, and in particular linoleic acid, retinol, retinoic acid, ascorbic acid alkyl esters, polyunsaturated fatty acids, nicotinic esters, tocopherol nicotinate, unsaponifiables of rice, soybean or shea, ceramides, hydroxy acids such as glycolic acid, selenium derivatives, antioxidants, beta-carotene, gamma-orizanol and stearyl glycerate. The cosmetics are commercially available and/or can be prepared by techniques known in the art.

Examples of nutritional supplements contemplated for use in the practice of the present invention include, but are not limited to, proteins, carbohydrates, water-soluble vitamins (e.g., vitamin C, B-complex vitamins, and the like), fat-soluble vitamins (e.g., vitamins A, D, E, K, and the like), and herbal extracts. The nutritional supplements are commercially available and/or can be prepared by techniques known in the art.

The term pesticide is understood to encompass herbicides, insecticides, acaricides, nematicides, ectoparasiticides and fungicides. Examples of compound classes to which the pesticide in the present invention may belong include ureas, triazines, triazoles, carbamates, phosphoric acid esters, dinitroanilines, morpholines, acylalanines, pyrethroids, benzilic acid esters, diphenylethers and polycyclic halogenated hydrocarbons. Specific examples of pesticides in each of these classes are listed in Pesticide Manual, 9th Edition, British Crop Protection Council. The pesticides are commercially available and/or can be prepared by techniques known in the art.

In a preferred embodiment of the present invention, the active agent is a macromolecule, such as a protein, a polypeptide, a carbohydrate, a polynucleotide, a virus, or a nucleic acid. Nucleic acids include DNA, oligonucleotides, antisense oligonucleotides, aptimers, RNA, and SiRNA. The macromolecule can be natural or synthetic. The protein can be an antibody, which can be monoclonal or polyclonal. The protein can also be any known therapeutic proteins isolated from natural sources or produced by synthetic or recombinant methods. Examples of therapeutic proteins include, but are not limited to, proteins of the blood clotting cascade (e.g., Factor VII, Factor VIII, Factor IX, et al.), subtilisin, ovalbumin, alpha-1-antitrypsin (AAT), DNase, superoxide dismutase (SOD), lysozyme, ribonuclease, hyaluronidase, collagenase, growth hormone, erythropoetin, insulin-like growth factors or their analogs, interferons, glatiramer, granulocyte-macrophage colony-stimulating factor, granulocyte colony-stimulating factor, antibodies, PEGylated proteins, glycosylated or hyperglycosylated proteins, desmopressin, LHRH agonists such as: leuprolide, goserelin, nafarelin, buserelin; LHRH antagonists, vasopressin, cyclosporine, calcitonin, parathyroid hormone, parathyroid hormone peptides and insulin. Preferred therapeutic proteins are insulin, alpha-1 antitrypsin, LHRH agonists and growth hormone.

Examples of low molecular weight therapeutic molecules include, but are not limited to, steroids, beta-agonists, anti-microbials, antifungals, taxanes (antimitotic and antimicrotubule agents), amino acids, aliphatic compounds, aromatic compounds, and urea compounds.

In a preferred embodiment, the active agent is a therapeutic agent for treatment of pulmonary disorders. Examples of such agents include, but are not limited to, steroids, beta-agonists, anti-fungals, anti-microbial compounds, bronchial dialators, anti-asthmatic agents, non-steroidal anti-inflammatory agents (NSAIDS), alpha-1-antitrypsin, and agents to treat cystic fibrosis. Examples of steroids include but are not limited to beclomethasone (including beclomethasone dipropionate), fluticasone (including fluticasone propionate), budesonide, estradiol, fludrocortisone, flucinonide, triamcinolone (including triamcinolone acetonide), and flunisolide. Examples of beta-agonists include but are not limited to salmeterol xinafoate, formoterol fumarate, levo-albuterol, bambuterol, and tulobuterol.

Examples of anti-fungal agents include but are not limited to itraconazole, fluconazole, and amphotericin B.

Diagnostic agents include the x-ray imaging agent and contrast media. Examples of x-ray imaging agents include WIN-8883 (ethyl 3,5-diacetamido-2,4,6-triiodobenzoate) also known as the ethyl ester of diatrazoic acid (EEDA), WIN 67722, i.e., (6-ethoxy-6-oxohexyl-3,5-bis(acetamido)-2,4,6-triiodobenzoate; ethyl-2-(3,5-bis(acetamido)-2,4,6-triiodobenzoyloxy)butyrate (WIN 16318); ethyl diatrizoxyacetate (WIN 12901); ethyl 2-(3,5-bis(acetamido)-2,4,6-triiodobenzoyloxy)propionate (WIN 16923); N-ethyl 2-(3,5-bis(acetamido)-2,4,6-triiodobenzoyloxy acetamide (WIN 65312); isopropyl 2-(3,5-bis(acetamido)-2,4,6-triiodobenzoyloxy) acetamide (WIN 12855); diethyl 2-(3,5-bis(acetamido)-2,4, 6-triiodobenzoyloxy malonate (WIN 67721); ethyl 2-(3,5-bis (acetamido)-2,4,6-triiodobenzoyloxy)phenylacetate (WIN 67585); propanedioic acid, [[3,5-bis(acetylamino)-2,4,5-triodobenzoyl]oxy]bis(1-methyl)ester (WIN 68165); and benzoic acid, 3,5-bis(acetylamino)-2,4,6-triodo-4-(ethyl-3-ethoxy-2-butenoate)ester (WIN 68209). Preferred contrast agents include those which are expected to disintegrate relatively rapidly under physiological conditions, thus minimizing any particle associated inflammatory response. Disintegration may result from enzymatic hydrolysis, solubilization of carboxylic acids at physiological pH, or other mechanisms. Thus, poorly soluble iodinated carboxylic acids such as iodipamide, diatrizoic acid, and metrizoic acid, along with hydrolytically labile iodinated species such as WIN 67721, WIN 12901, WIN 68165, and WIN 68209 or others may be preferred.

Numerous combinations of active agents may be desired including, for example, a combination of a steroid and a beta-agonist, e.g., fluticasone propionate and salmeterol, budesonide and formeterol, etc.

Examples of carbohydrates are dextrans, hetastarch, cyclodextrins, alginates, chitosans, chondroitins, heparins and the like.

The Small Spherical Particles

The particles and the small spherical particles of the present invention preferably have an average geometric particle size of from about 0.01 µm to about 200 µm, more preferably from 0.1 µm to 10 µm, even more preferably from about 0.5 µm to about 5 µm, and most preferably from about 0.5 µm to about 3 µm, as measured by dynamic light scattering methods (e.g., photocorrelation spectroscopy, laser diffraction, low-angle laser light scattering (LALLS), medium-angle laser light scattering (MALLS)), by light obscuration methods (Coulter analysis method, for example) or by other methods, such as rheology or microscopy (light or electron). Particles for pulmonary delivery will have an aerodynamic particle size determined by time of flight measurements (e.g., Aerosolizer) or Andersen Cascade Impactor measurements.

The small spherical particles are substantially spherical. What is meant by "substantially spherical" is that the ratio of the lengths of the longest to the shortest perpendicular axes of the particle cross section is less than or equal to about 1.5. Substantially spherical does not require a line of symmetry. Further, the particles may have surface texturing, such as lines or indentations or protuberances that are small in scale when compared to the overall size of the particle and still be substantially spherical. More preferably, the ratio of lengths between the longest and shortest axes of the particle is less than or equal to about 1.33. Most preferably, the ratio of lengths between the longest and shortest axes of the particle is less than or equal to about 1.25. Surface contact is minimized in microspheres that are substantially spherical, which minimizes the undesirable agglomeration of the particles upon storage. Many crystals or flakes have flat surfaces that can allow large surface contact areas where agglomeration can occur by ionic or non-ionic interactions. A sphere permits contact over a much smaller area.

The particles also preferably have substantially the same particle size. Particles having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. This invention creates spherical particles with a narrow size distribution, thereby minimizing opportunities for contact agglomeration. What is meant by a "narrow size distribution" is a preferred particle size distribution would have a ratio of the volume diameter of the $90^{th}$ percentile of the small spherical particles to the volume diameter of the $10^{th}$ percentile less than or equal to 5. More preferably, the particle size distribution would have ratio of the volume diameter of the $90^{th}$ percentile of the small spherical particles to the volume diameter of the $10^{th}$ percentile less than or equal to 3. Most preferably, the particle size distribution would have ratio of the volume diameter of the $90^{th}$ percentile of the small spherical particles to the volume diameter of the $10^{th}$ percentile less than or equal to 2.

Geometric Standard Deviation (GSD) can also be used to indicate the narrow size distribution. GSD calculations involved determining the effective cutoff diameter (ECD) at the cumulative less than percentages of 15.9% and 84.1%. GSD is equal to the square root of the ratio of the ECD less than 84.17% to ECD less then 15.9%. The GSD has a narrow size distribution when GSD<2.5, more preferably less than 1.8.

In a preferred form of the invention, the active agent in the small spherical particles is semi-crystalline or non-crystalline.

Typically, small spherical particles made by the process in this invention are substantially non-porous and have a density greater than 0.5 $g/cm^3$, more preferably greater than 0.75 $g/cm^3$ and most preferably greater than about 0.85 $g/cm^3$. A preferred range for the density is from about 0.5 to about 2 $g/cm^3$ and more preferably from about 0.75 to about 1.75 $g/cm^3$ and even more preferably from about 0.85 $g/cm^3$ to about 1.5 $g/cm^3$.

The particles of the present invention can exhibit high content of the active agent. There is no requirement for a significant quantity of bulking agents or similar excipients that are required by many other methods of preparing particles. For example, insulin small spherical particles consist of equal to or greater than 95% by weight of the particles. However, bulking agents or excipients may be included in the particles. Preferably, the active agent is present from about 0.1% to greater than 95% by weight of the particle, more preferably from about 30% to about 100% by weight, even more preferably from about 50% to about 100% by weight, yet more preferably from about 75% to about 100% by weight, and most preferably greater than 90% by weight. When stating ranges herein, it is meant to include any range or combination of ranges therein.

A further aspect of the present invention is that the small spherical particles retain the biochemical integrity and the biological activity of the active agent with or without the inclusion of excipients.

In Vivo Delivery of the Particles

The particles containing the active agent in the present invention are suitable for in vivo delivery to a subject in need of the agent by a suitable route, such as injectable, topical, oral, rectal, nasal, pulmonary, vaginal, buccal, sublingual, transdermal, transmucosal, otic, intraocular or ocular. The particles can be delivered as a stable liquid suspension or formulated as a solid dosage form such as tablets, caplets, capsules, etc. A preferred delivery route is injectable, which includes intravenous, intramuscular, subcutaneous, intraperitoneal, intrathecal, epidural, intra-arterial, intra-articular and the like. Another preferred route of delivery is pulmonary inhalation. In this route of delivery, the particles may be deposited to the deep lung, in the upper respiratory tract, or anywhere in the respiratory tract. The particles may be delivered as a dry powder by a dry powder inhaler, or they may be delivered by a metered dose inhaler or a nebulizer.

Drugs intended to function systemically, such as insulin, are desirably deposited in the alveoli, where there is a very large surface area available for absorption into the bloodstream. When targeting the drug deposition to certain regions within the lung, the aerodynamic diameter of the particle can be adjusted to an optimal range by manipulating fundamental physical characteristics of the particles such as shape, density, and particle size.

Acceptable respirable fractions of inhaled drug particles are often achieved by adding excipients to the formulation, either incorporated into the particle composition or as a mixture with the drug particles. For example, improved dispersion of micronized drug particles (about 5 µm) is effected by blending with larger (30-90 µm) particles of inert carrier particles such as trehalose, lactose or maltodextrin. The larger excipient particles improve the powder flow properties, which correlates with an improved pharmacodynamic effect. In a further refinement, the excipients are incorporated directly into the small spherical particles to effect aerosol performance as well as potentially enhancing the stability of protein drugs. Generally, excipients are chosen that have been previously FDA approved for inhalation, such as lactose, or organic molecules endogenous to the lungs, such as albumin and DL-α-phosphatidylcholine dipalmitoyl (DPPC). Other excipients, such as poly(lactic acid-co-glycolic acid) (PLGA) have been used to engineer particles with desirable physical and chemical characteristics. However, much of the inhalation experience with FDA approved excipients has been with asthma drugs having large aerodynamic particle sizes that desirably deposit in the tracheobronchial region, and which do not appreciably penetrate to the deep lung. For inhaled protein or peptide therapeutics delivered to the deep lung, there is concern that undesirable long-term side effects, such as inflammation and irritation can occur which may be due to an immunological response or caused by excipients when they are delivered to the alveolar region.

In order to minimize potential deleterious side effects of deep lung inhaled therapeutics, it may be advantageous to fabricate particles for inhalation that are substantially constituted by the drug to be delivered. This strategy would minimize alveolar exposure to excipients and reduce the overall mass dose of particles deposited on alveolar surfaces with each dose, possibly minimizing irritation during chronic use of the inhaled therapeutic. Small spherical particles with aerodynamic properties suitable for deep lung deposition that are essentially composed entirely of a therapeutic protein or peptide may be particularly useful for isolated studies on the effects of chronic therapeutic dosing on the alveolar membrane of the lung. The effects of systemic delivery of protein or peptide in the form of small spherical particles by inhalation could then be studied without complicating factors introduced by associated excipients.

The requirements to deliver particles to the deep lung by inhalation are that the particles have a small mean aerodynamic diameter of 0.5-10 micrometers and a narrow size distribution. The invention also contemplates mixing together of various batches of particles having different particle size ranges. The process of the present invention allows the fabrication of small spherical particles with the above characteristics.

There are two principal approaches for forming particles with aerodynamic diameters of 0.5 to 3 micron. The first approach is to produce relatively large but very porous (or perforated) microparticles. Since the relationship between the aerodynamic diameter ($D_{aerodynamic}$) and the geometric diameter ($D_{geometric}$) is $D_{aerodynamic}$ is equal to $D_{geometric}$ multiplied by the square root of the density of the particles with very low mass density (around 0.1 $g/cm^3$) can exhibit small aerodynamic diameters (0.5 to 3 microns) while possessing relatively high geometric diameters (5 to 10 microns).

An alternative approach is to produce particles with relatively low porosity, in the case of the present invention, the particles have a density, set forth in the ranges above, and more generally that is close to 1 $g/cm^3$. Thus, the aerodynamic diameter of such non-porous dense particles is close to their geometric diameter.

The present method for particle formation set forth above, provides for particle formation with or without excipients.

Fabrication of protein small spherical particles from protein itself with no additives provides superior advantages for use in pulmonary delivery as it provides options for larger drug payloads, increased safety and decreased numbers of required inhalations.

Microencapsulation of Pre-Fabricated Small Spherical Particles

The small spherical particles of the present invention or small particles prepared from other methods (including microparticles, microspheres, nanospheres, nanoparticles, etc.) can further be encapsulated within matrices of wall-forming materials to form microencapsulated particles. The microencapusulation can be accomplished by any process known in the art. In a preferred embodiment, microencapsulation of the small spherical particles of the present invention or any other small particles is accomplished by an emulsification/solvent extraction processes as described below. The matrix can impart sustained release properties to the active agent resulting in release rates that persist from minutes to hours, days or weeks according to the desired therapeutic applications. The microencapsulated particles can also produce delayed release formulations of the pre-fabricated small spherical particles. In a preferred embodiment, the pre-fabricated small spherical particles are particles of macromolecules. In another preferred embodiment, the macromolecule is a protein or polypeptide.

In the emulsification/solvent extraction process, emulsification is obtained by mixing two immiscible phases, the continuous phase and the discontinuous phase (which is also known as the dispersed phase), to form an emulsion. In a preferred embodiment, the continuous phase is an aqueous phase (or the water phase) and the discontinuous phase is an organic phase (or the oil phase) to form an oil-in-water (O/W) emulsion. The discontinuous phase may further contain a dispersion of solid particles present either as a fine suspension or as a fine dispersion forming a solid-in-oil (S/O) phase. The organic phase is preferably a water immiscible or a partially water miscible organic solvent. The ratio by weights of the organic phase to the aqueous phase is from about 1:99 to about 99:1, more preferably from 1:99 to about 40:60, and most preferably from about 2:98 to about 1:3, or any range or combination of ranges therein. In a preferred embodiment, the ratio of the organic phase to the aqueous phase is about 1:3. The present invention further contemplates utilizing reverse emulsions or water-in-oil emulsion (W/O) where the oil phase forms the continuous phase and water phase forms the discontinuous phase. The present invention further contemplates utilizing emulsions having more than two phases such as an oil-in-water-in-oil emulsion (O/W/O) or a water-in-oil-in-water emulsion (W/O/W).

In a preferred embodiment, the process of microencapsulation using the emulsification/solvent extraction process starts with preparing pre-fabricated small spherical particles by the methods described earlier and an organic phase containing the wall-forming material. The pre-fabricated small spherical particles are dispersed in the organic phase of the wall-forming material to form a solid-in-oil (S/O) phase containing a dispersion of the pre-fabricated small spherical particles in the oil phase. In a preferred embodiment, the dispersion is accomplished by homogenizing the mixture of the small spherical particles and the organic phase. An aqueous medium will form the continuous phase. In this case, the emulsion system formed by emulsifying the S/O phase with an aqueous phase is a solid-in-oil-in-water (S/O/W) emulsion system.

The wall-forming material refers to materials capable of forming the structural entity of the matrix individually or in combination. Biodegradable wall-forming materials are preferred, especially for injectable applications. Examples of such materials include but are not limited to the family of poly-lactide/poly-glycolide polymers (PLGA's), polyethylene glycol conjugated PLGA's (PLGA-PEG's), and triglycerides. In the embodiment in which PLGA or PLGA-PEG is used, the PLGA preferably has a ratio of poly-lactide to poly-glycolide of from 100:0 to 0:100, more preferably from about 90:10 to about 15:85, and most preferably about 50:50. In general, the higher the ratio of the poly-glycolide to the poly-lactide in the polymer, the more hydrophilic is the microencapsulated particles resulting in faster hydration and faster degradation. Various molecular weights of PLGA can also be used. In general, for the same ratio of poly-glycolide and poly-lactide in the polymer, the higher the molecular weight of the PLGA, the slower is the release of the active agent, and the wider the distribution of the size of the microencapsulated particles.

The organic solvent in the organic phase (oil phase) of an oil-in-water (O/W) or solid-in-oil-in-water (S/O/W) emulsion can be aqueous immiscible or partially aqueous immiscible. What is meant by the term "water immiscible solvent" are those solvents which form an interfacial meniscus when combined with an aqueous solution in a 1:1 ratio (O/W). Suitable water immiscible solvents include, but are not limited to, substituted or unsubstituted, linear, branched or cyclic alkanes with a carbon number of 5 or higher, substituted or unsubstituted, linear, branched or cyclic alkenes with a carbon number of 5 or higher, substituted or unsubstituted, linear, branched or cyclic alkynes with a carbon number of 5 or higher; aromatic hydrocarbons completely or partially halogenated hydrocarbons, ethers, esters, ketones, mono-, di- or tri-glycerides, native oils, alcohols, aldehydes, acids, amines, linear or cyclic silicones, hexamethyldisiloxane, or any combination of these solvents. Halogenated solvents include, but are not limited to carbon tetrachloride, methylene chloride, chloroform, tetrachloroethylene, trichloroethylene, trichloroethane, hydrofluorocarbons, chlorinated benzene (mono, di, tri), trichlorofluoromethane. Particularly suitable solvents are methylene chloride, chloroform, diethyl ether, toluene, xylene and ethyl acetate. What is meant by "partially water miscible solvents" are those solvents which are water immiscible at one concentration, and water miscible at another lower concentration. These solvents are of limited water miscibility and capable of spontaneous emulsion formation. Examples of partially water miscible solvents are tetrahydrofuran (THF), propylene carbonate, benzyl alcohol, and ethyl acetate.

A surface active compound can be added, for example, to increase the wetting properties of the organic phase. The surface active compound can be added before the emulsification process to the aqueous phase, to the organic phase, to both the aqueous medium and the organic solution, or after the emulsification process to the emulsion. The use of a surface active compound can reduce the number of unencapsulated or partially encapsulated small spherical particles, resulting in reduction of the initial burst of the active agent during the release. The surface active compound can be added to the organic phase, or to the aqueous phase, or to both the organic phase and the aqueous phase, depending on the solubility of the compound.

What is meant by the term "surface active compounds" are compounds such as an anionic surfactant, a cationic surfactant, a zwitterionic surfactant, a nonionic surfactant or a biological surface active molecule. The surface active compound should be present in an amount by weight of the aqueous phase or the organic phase or the emulsion, whatever the case may be, from less than about 0.01% to about 30%, more preferably from about 0.01% to about 10%, or any range or combination of ranges therein.

Suitable anionic surfactants include but are not limited to: potassium laurate, sodium lauryl sulfate, sodium dodecylsulfate, alkyl polyoxyethylene sulfates, sodium alginate, dioctyl sodium sulfosuccinate, phosphatidyl choline, phosphatidyl glycerol, phosphatidyl inosine, phosphatidylserine, phosphatidic acid and their salts, glyceryl esters, sodium carboxymethylcellulose, cholic acid and other bile acids (e.g., cholic acid, deoxycholic acid, glycocholic acid, taurocholic acid, glycodeoxycholic acid) and salts thereof (e.g., sodium deoxycholate, etc.).

Suitable cationic surfactants include, but are not limited to, quaternary ammonium compounds, such as benzalkonium chloride, cetyltrimethylammonium bromide, lauryldimethylbenzylammonium chloride, acyl carnitine hydrochlorides, or alkyl pyridinium halides. As anionic surfactants, phospholipids may be used. Suitable phospholipids include, for example phosphatidylcholine, phosphatidylethanolamine, phosphatidylserine, phosphatidyl inositol, phosphatidylglycerol, phosphatidic acid, lysophospholipids, egg or soybean phospholipid or a combination thereof. The phospholipid may be salted or desalted, hydrogenated or partially hydrogenated or natural, semisynthetic or synthetic.

Suitable nonionic surfactants include: polyoxyethylene fatty alcohol ethers (Macrogol and Brij), polyoxyethylene sorbitan fatty acid esters (Polysorbates), polyoxyethylene fatty acid esters (Myrj), sorbitan esters (Span), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers (poloxomers), polaxamines, polyvinyl alcohol, polyvinylpyrrolidone, and polysaccharides (including starch and starch derivatives such as hydroxyethylstarch (HES), methylcellulose, hydroxycellulose, hydroxy propylcellulose, hydroxy propylmethylcellulose, and noncrystalline cellulose). In a preferred form of the invention, the nonionic surfactant is a polyoxyethylene and polyoxypropylene copolymer and preferably a block copolymer of propylene glycol and ethylene glycol. Such polymers are sold under the tradename POLOXAMER also sometimes referred to as PLURONIC®, and sold by several suppliers including Spectrum Chemical and Ruger. Among polyoxyethylene fatty acid esters is included those having short alkyl chains. One example of such a surfactant is SOLUTOL® HS 15, polyethylene-660-hydroxystearate, manufactured by BASF Aktiengesellschaft.

Surface active biological molecules include such molecules as albumin, casein, heparin, hirudin, hetastarch or other appropriate biocompatible agents.

In a preferred form of the invention, the aqueous phase includes a protein as the surface active compound. A preferred protein is albumin. The protein may also function as an excipient. In embodiments in which protein is not the surface active compound, other excipients may be included in the emulsion, added either before or after the emulsification process. Suitable excipients include, but are not limited to, saccharides, disaccharides, and sugar alcohols. A preferred disaccharide is sucrose, and a preferred sugar alcohol is mannitol.

In addition, use of channeling agents, such as polyethylelne glycol (PEG), can increase the water permeation rate of the final product, which results in modification of the initial release kinetics of the active agent from the matrix as well as degradation rate of the matrix and degradation-dependent release kinetics by modifying the hydration rate. Using PEG as the channeling agent during encapsulation can be advantageous in terms of eliminating parts of the washing process during fabrication of the small spherical particles in which PEG is used as the phase-separation enhancing agent. In addition, varying pH of the continuous phase through use of buffers can significantly increase the wetting process between the particle surface and the organic phase, hence, results in significant reduction of the initial burst of the encapsulated therapeutic agent from the matrix of the microencapsulated particles. The properties of the continuous phase can also be modified, for example, by increasing its salinity by adding a salt such as NaCl, to reduce miscibility of the two phases.

After dispersing the small spherical particles in the organic phase (oil phase), the continuous phase of the aqueous medium (water phase) is then vigorously mixed, for example by homogenization or sonication, with the discontinuous phase of the organic phase to form an emulsion containing emulsified droplets of embryonic microencapsulated particles. The continuous aqueous phase can be saturated with the organic solvent used in the organic phase prior to mixing of the aqueous phase and the organic phase, in order to minimize rapid extraction of the organic solvent from the emulsified droplets. The emulsification process can be performed at any temperature in which the mixture can maintain its liquid properties. The emulsion stability is a function of the concentration of the surface active compound in the organic phase or in the aqueous phase, or in the emulsion if the surface active compound is added to the emulsion after the emulsification process. This is one of the factors that determines droplet size of the emulsion system (embryonic microencapsulated particles) and the size and size distribution of the microencapsulated particles. Other factors affecting the size distribution of microencapsulated particles are viscosity of the continuous phase, viscosity of the discontinous phase, shear forces during emulsification, type and concentration of surface active compound, and the Oil/Water ratio.

After the emulsification, the emulsion is then transferred into a hardening medium. The hardening medium extracts the solvent in the discontinous phase from the embryonic microencapsulated particles, resulting in formation of solid microencapsulated particles having a solid polymeric matrix around the pre-fabricated small spherical particles within the vicinity of the emulsified droplets. In the embodiment of an O/W or S/O/W system, the hardening medium is an aqueous medium, which may contain surface active compounds, or thickening agents, or other excipients. The microencapsulated particles are preferably spherical and have a particle size of from about 0.6 to about 300 μm, and more preferably from about 0.8 to about 60 μm. Additionally, the microencapsulated particles preferably have a narrow distribution of particle size. To reduce the extraction time of the discontinuous phase, heat or reduced pressure can be applied to the hardening medium. The extraction rate of discontinuous phase from the embryonic microencapsulated particles is an important factor in the degree of porosity in the final solid microencapsulated particles, since rapid removal, e.g., by evaporation (boiling effect), of the discontinuous phase results in destruction of the continuity of the matrix.

In a preferred embodiment, the emulsification process is performed in a continuous fashion instead of a batch process. FIG. 41 depicts the design of the continuous emulsification reactor.

In another preferred embodiment, the hardened wall-forming polymeric matrices, encapsulating the small spherical particles of the active agent, are further harvested by centrifugation and/or filtration (including diafiltration), and washed with water. The remaining liquid phases can further be removed by a process such as lyophilization or evaporation.

A. Insulin Small Spherical Particles

Example 1

General Method of Preparation of Insulin Small Spherical Particles

A solution buffered at pH 5.65 (0.033M sodium acetate buffer) containing 16.67% PEG 3350 was prepared. A concentrated slurry of zinc crystalline insulin was added to this solution while stirring. The insulin concentration in the final solution was 0.83 mg/mL. The solution was heated to about 85 to 90° C. The insulin crystals dissolved completely in this temperature range within five minutes. Insulin small spherical particles started to form at around 60° C. when the temperature of the solution was reduced at a controlled rate. The yield increased as the concentration of PEG increased. This process yields small spherical particles with various size distribution with a mean of 1.4 μm.

The insulin small spherical particles formed were separated from PEG by washing the microspheres via diafiltration under conditions in which the small spherical particles do not dissolve. The insulin small spherical particles were washed out of the suspension using an aqueous solution containing $Zn^{2+}$. The $Zn^{2+}$ ion reduces the solubility of the insulin and prevents dissolution that reduces yield and causes small spherical particle agglomeration.

Example 2

Non-Stirred Batch Process for Making Insulin Small Spherical Particles 20.2 mg of zinc crystalline insulin were suspended in 1 mL of deionized water at room temperature. 50 microliters of 0.5 N HCl was added to the insulin. 1 mL of deionized water was added to form a 10 mg/mL solution of zinc crystalline insulin. 12.5 g of Polyethylene Glycol 3350 (Sigma) and 12.5 g of Polyvinylpyrrolidone (Sigma) were dissolved in 50 mL of 100 millimolar sodium acetate buffer, pH5.7. The polymer solution volume was adjusted to 100 mL with the sodium acetate buffer. To 800 microliters of the polymer solution in an eppendorf tube was added 400 microliters of the 10 mg/mL insulin solution. The insulin/polymer solution became cloudy on mixing. A control was prepared using water instead of the polymer solution. The eppendorf tubes were heated in a water bath at 90° C. for 30 minutes without mixing or stirring, then removed and placed on ice for 10 minutes. The insulin/polymer solution was clear upon removal from the 90° C. water bath, but began to cloud as it cooled. The control without the polymer remained clear throughout the experiment. Particles were collected from the insulin/polymer tube by centrifugation, followed by washing twice to remove the polymer. The last suspension in water was lyophilized to obtain a dry powder. SEM analysis of the lyophilized particles from the insulin/polymer tubes showed a uniform distribution of small spherical particles around 1 micrometer in diameter. Coulter light scattering particle size analysis of the particles showed a narrow size distribution with a mean particle size of 1.413 micrometers, 95% confidence limits of 0.941-1.88 micrometers, and a standard deviation of 0.241 micrometers. An insulin control without polymer or wash steps, but otherwise processed and lyophilized in the same manner, showed only flakes (no particles) under the SEM similar in appearance to that typically obtained after lyophilizing proteins.

Example 3

The Continuous Flow Through Process for Making Insulin Small Spherical Particles 36.5 mg of insulin was weighed out and suspended in 3 mL of deionized water. 30 μL of 1 N HCl was added to dissolve the insulin. The final volume of the solution was adjusted to 3.65 mL with deionized water. 7.3 mL of PEG/PVP solution (25% PEG/PVP pH 5.6 in 100 mM NaOAc buffer) was then added to the insulin solution to a final total volume of 10.95 mL of insulin solution. The solution was then vortexed to yield a homogenous suspension of insulin and PEG/PVP.

The insulin suspension was connected to a BioRad peristaltic pump running at a speed of 0.4 mL/min through Teflon® tubing (TFE ½2" inner diameter flexible tubing). The tubing from the pump was submerged into a water bath maintained at 90° C. before being inserted into a collection tube immersed in ice. Insulin small spherical particles were formed when the temperature of the insulin solution was decreased from about 90° C. in the water bath to about 4° C. in the collection tube in ice. FIG. 7 is a schematic diagram of this process. The total run time for the process was 35 minutes for the 10.95 mL volume. After collecting the small spherical particles, the collection tube was centrifuged at 3000 rpm for 20 minutes in a Beckman J6B centrifuge. A second water wash was completed and the small spherical particle pellets were centrifuged at 2600 rpm for 15 minutes. The final water wash was centrifuged at 1500 rpm for 15 minutes. An aliquot was removed for particle size analysis. The small spherical particles were frozen at −80° C. and lyophilized for 2 days.

The particle size was determined to be 1.397 μm by volume, 1.119 μm by surface area, and 0.691 μm by number as determined by the Beckman Coulter LS 230 particle counter. The scanning electron micrograph indicated uniform sized and non-agglomerated insulin small spherical particles (FIG. 8).

The use of the continuous flow through process where the insulin solution was exposed to 90° C. for a short period of time allowed for the production of small spherical particles. This method yielded a final composition that was 90% protein as determined by high performance liquid chromatography (HPLC) (FIG. 9). HPLC analysis also indicated that the dissolved insulin small spherical particles had an elution time of about 4.74 minutes, not significantly different from that of an insulin standard or the native insulin starting material, indicating that preservation of the biochemical integrity of the insulin after fabrication into the small spherical particles.

Example 4

Heat Exchanger Batch Process for Making Insulin Small Spherical Particles

Human zinc crystalline insulin was suspended in a minimal amount of deionized water with sonication to ensure complete dispersion. The insulin suspension was added to a stirred, buffered polymer solution (pH 5.65 at 25° C.) preheated to 77° C., so that the final solute concentrations were 0.83% zinc crystalline insulin, 18.5% polyethylene glycol 3350, 0.7% sodium chloride, in a 0.1 M sodium acetate buffer. The initially cloudy mixture cleared within three minutes as the crystalline insulin dissolved. Immediately after clearing, the solution was transferred to a glass, water-jacketed chromatography column that was used as a heat exchanger (column i.d.: 25 mm, length: 600 mm; Ace Glass Incorporated, Vineland, N.J.). The glass column was positioned vertically, and the heat exchange fluid entered the water jacket at the bottom of the column and exited at the top. In order to document the heat exchange properties of the system, thermocouples (Type J, Cole Parmer) were positioned in the center of the insulin formulation liquid at the top and bottom of the column and a cooling temperature profile was obtained during a preliminary trial run. The thermocouples were removed during the six batches conducted for this experiment so as not to introduce a foreign surface variable.

The heat exchanger was pre-heated to 65° C. and the insulin-buffered polymer solution was transferred in such a manner that the solution temperature did not drop below 65° C. and air bubbles were not introduced into the solution. After the clear solution was allowed four minutes to equilibrate to 65° C. in the heat exchanger, the heat exchange fluid was switched from a 65° C. supply to a 15° C. supply. The insulin formulation in the heat exchanger was allowed to equilibrate to 15° C. over a twenty-minute period. The insulin small spherical particles formed as the temperature dropped through 60 to 55° C. resulting in a uniform, stable, creamy white suspension.

The insulin small spherical particles were separated from the polyethylene glycol by diafiltration (A/G Technologies, 750,000 MWCO ultrafiltration cartridge) against five volumes of 0.16% sodium acetate—0.026% zinc chloride buffer, pH 7.0, followed by concentration to one fifth of the original volume. The insulin small spherical particles suspension was further washed by diafiltration against five volumes of deionized water, followed by lyophilization to remove the water. Care was taken to prevent agglomeration of the small spherical particles during diafiltration (from polarization packing of particles on the membrane surface) and during lyophilization (from settling of the small spherical particles prior to freezing). The dried small spherical particles were free flowing and ready for use, with no de-agglomeration or sieving required.

Small Spherical Particles of Insulin

The above described process produces uniform size spherical particles from zinc crystalline insulin without added excipients. Small spherical particles prepared by this process have excellent aerodynamic properties as determined by time-of-flight (Aerosizer™) and Andersen Cascade Impactor measurements, with high respirable fractions indicative of deep lung delivery when delivered from a simple, widely used dry powder inhaler (Cyclohaler™). By using insulin as a model protein, we are also able to examine the effect of the process on the chemical integrity of the protein using established U.S.P. methods.

Dry powder insulin small spherical particles were imaged by polarized light microscopy (Leica EPISTAR®, Buffalo, N.Y.) and with a scanning electron microscope (AMRAY 1000, Bedford, Mass.). Particle size analysis was performed using an Aerosizer® Model 3292 Particle Sizing System which included a Model 3230 Aero-Disperser® Dry Powder Disperser for introducing the powder to the instrument (TSI Incorporated, St. Paul, Minn.). Individual particle sizes were confirmed by comparing the Aerosizer results to the electron micrographs.

The chemical integrity of the insulin before and after the process was determined by HPLC according to the USP monograph for Insulin Human (USP 26). The insulin and high molecular weight protein content was measured using an isocratic SEC HPLC method with UV detection at 276 nm. To measure insulin, A-21 desamido insulin and other insulin related substances, the sample was analyzed using a USP gradient reverse-phase HPLC method. The insulin content is measured using UV detection at 214 nm. High molecular weight protein, desamido insulin, and other insulin related substances were assayed to quantitate any chemical degradation caused by the process.

The aerodynamic characteristics of the insulin small spherical particles were examined using the Aerosizer® instrument. Size distribution measurements on insulin dry powder were conducted using the AeroDisperser attachment with low shear force, medium feed rate, and normal deagglomeration. The instruments' software converts time-of-flight data into size and places it into logarithmically spaced ranges. The number of particles detected in each size bin was used for statistical analysis, as well as the total volume of particles detected in each size bin. The volume distribution emphasizes large particles more than the number distribution and, therefore, is more sensitive at detecting agglomerates of non-dispersed particles as well as large particles.

The Andersen Cascade Impactor assembly consisted of a pre-separator, nine stages, eight collection plates, and a backup filter. The stages are numbered −1, −0, 1, 2, 3, 4, 5, 6, and F. Stage −1 is an orifice stage only. Stage F contains the collection plate for Stage 6 and the backup filter. The stainless steel collection plates were coated with a thin layer of food grade silicone to prevent "bounce" of the particles. A sample stream air-flow rate of 60 LPM through the sampler was used for the analysis. An accurately weighed sample size of approximately 10 mg was weighed into each starch capsule (Vendor), with the powder delivered as an aerosol from the Cyclohaler in four seconds. The amount of insulin powder deposited on each plate was determined by reversed phase HPLC detection at 214 nm according to the USP 26 assay for human insulin.

The mass median aerodynamic diameter (MMAD) was calculated by Sigma Plot software using a probit fit of the cumulative less than mass percent versus the effective cutoff diameter (ECD). Emitted dose (ED) was determined as the total observed mass of insulin deposited into the cascade Impactor. This is expressed as a percentage of the mass of the insulin small spherical particles loaded into the Cyclohaler capsule.

The results demonstrate that careful control of process parameters in conjunction with a phase change formulation can produce: 1) predominantly spherical particles with a diameter of about 2 μm; 2) a narrow size distribution; 3) and reproducible aerodynamic properties from batch to batch; and 4) small spherical particles composed of over 95% active drug (human insulin) excluding residual moisture. We determined that the solubility of the zinc crystalline insulin could be controlled by solution temperature, pH, polymer concentration, and ionic strength. We also found that controlling the cooling rate during the phase change period was an important parameter that enabled the formation of predominantly spherical particles within a narrow size range.

FIG. 2 is a cooling temperature profile for the process corresponding to this Example. The profile was measured using a water-jacketed chromatography column positioned vertically and heat-exchange fluid entered the water jacket at the bottom of the column and exited at the top. Two thermocouples were positioned in the column and in contact with the solution. One thermocouple is placed at a top of the column and the second at the bottom of the column. The temperature curves divide the time-temperature plot into distinct regions, where prior optimization experiments determined the induced phase change above or below an optimal rate of temperature change tends to result in a broader range of particle sizes and non-spherical shapes. At temperatures greater than 60° C., the insulin remains soluble in the buffered polymer solution (Region A; FIG. 2). When the temperature decreases at rates from approximately 8.6° C./minute to 26.5° C./minute, optimal formation of uniformed sized, spherical particles is favored (Region B; FIG. 2). If a cooling rate is faster than 25.6° C./minute is applied to the formulation, there is a tendency to produce very fine (less than 0.5 micron) non-spherical particles of insulin that readily agglomerate (Region C; FIG. 2). Cooling rates slower than 8.6° C./minute tend to produce a broader size distribution of insulin small spherical particles along with non-spherical shapes and amorphous flocculent precipitate (Region D; FIG. 2).

As the temperature of the insulin-buffered polymer solution within the heat exchanger falls within region B of FIG. 2, a phase change occurs resulting in a milky-white, stable suspension of insulin small spherical particles. Phase separation indicating microsphere formation begins to occur as the temperature drops below 60° C. and appears to be complete as the temperature reaches 40° C. No further change in the suspension was observed as the formulation was cooled to 15° C. prior to washing by diafiltration to remove the PEG polymer.

Figure 3A:
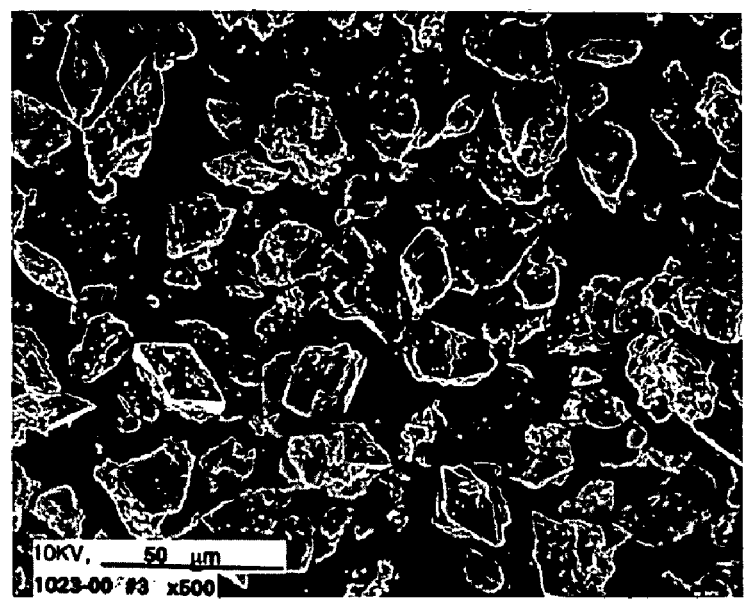
FIG. 3a is a scanning electron micrograph (SEM) of the starting insulin material.
Figure 3B:
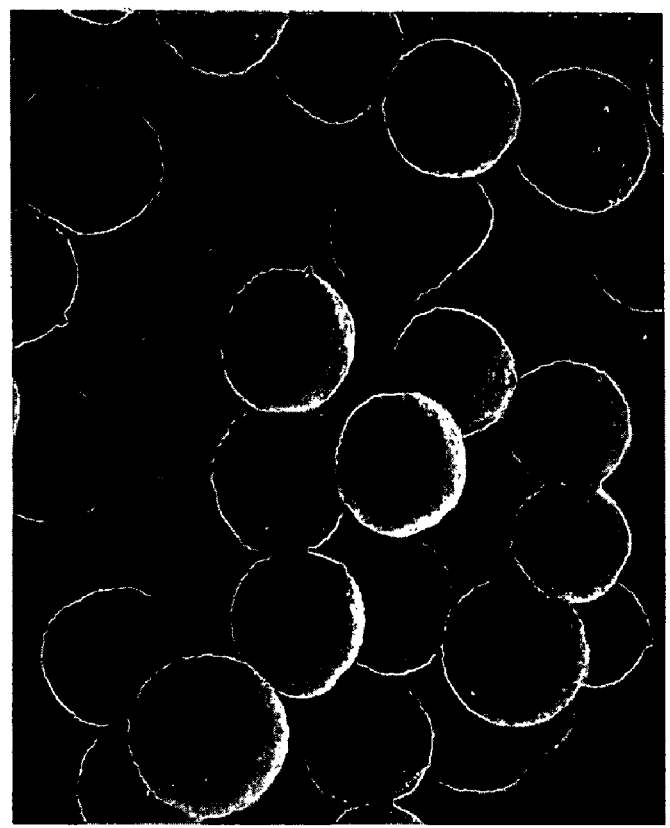
FIG. 3b is an SEM of a small spherical particle of insulin (Example 4).
Figure 10C:
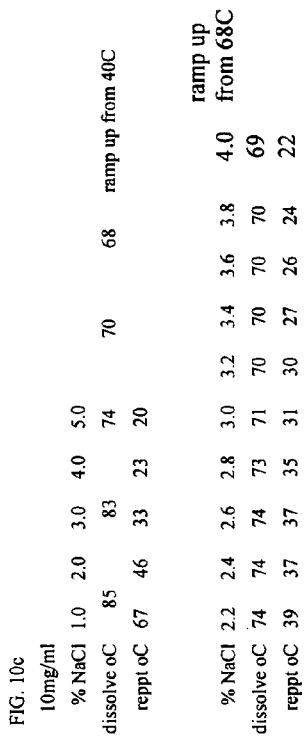
Figure 10D:
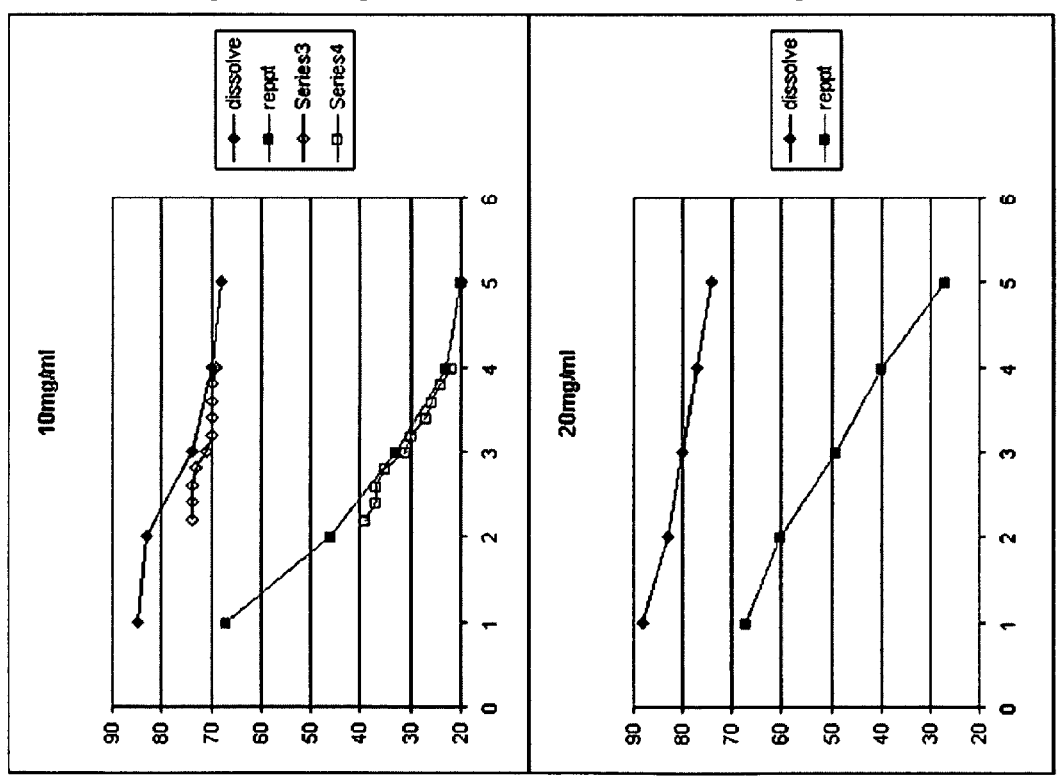
Figure 10E:
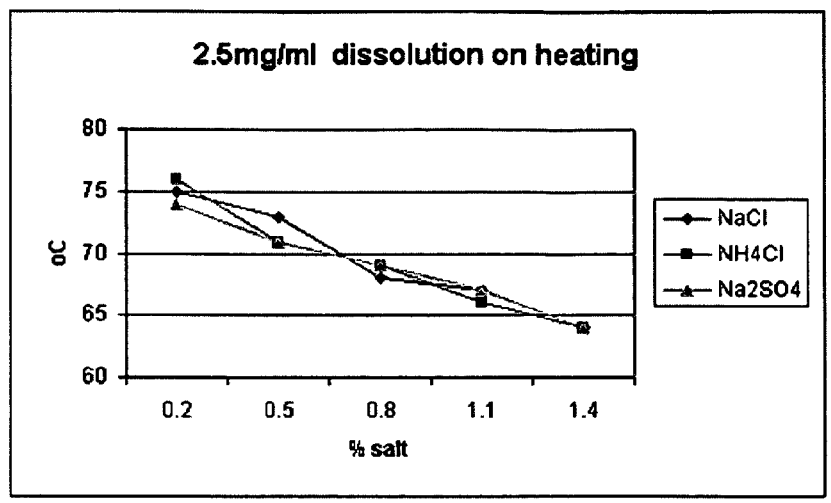
Figure 10F:
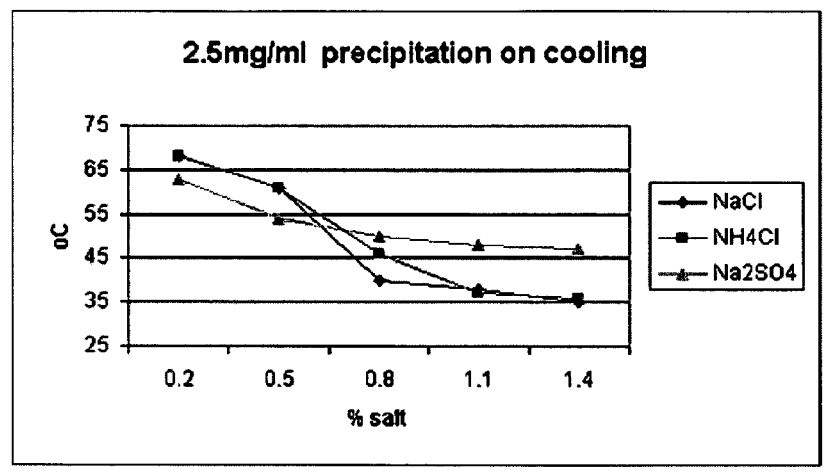
Figure 10G:
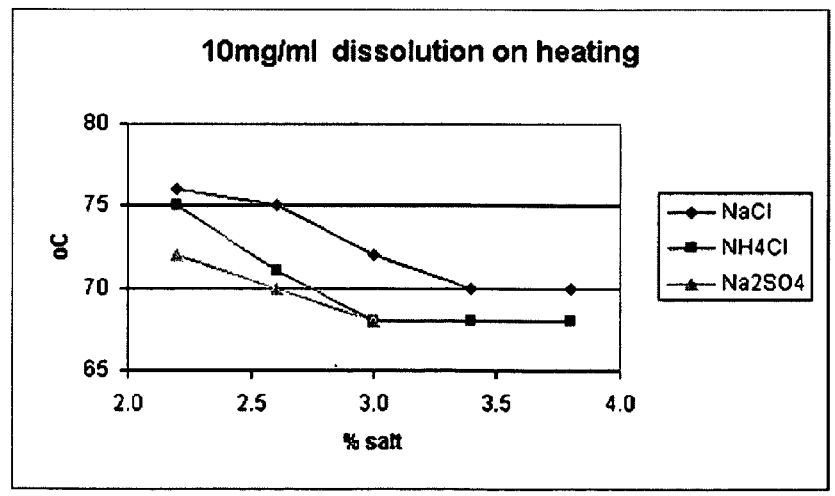

Whereas an SEM of the starting human zinc crystalline insulin raw material shows non-homogenous size and crystalline shapes with particle sizes of approximately 5 to 40 µm, SEM pictures taken of one of the batches from this Example show the spherical shape and uniform size of the insulin small spherical particles (FIG. 3b). The particle shape and size illustrated by the SEM is representative of the other five batches prepared for this Example.

Following separation from the buffered polymer by diafiltration washing and lyophilization from a deionized water suspension, the dry powder insulin small spherical particles were relatively free flowing and easily weighed and handled. The insulin small spherical particles moisture content ranged from 2.1 to 4.4% moisture, compared to 12% for the starting zinc crystalline insulin raw material. Chemical analysis of the insulin small spherical particles by HPLC indicated very little chemical degradation of insulin due to the process (FIG. 4), with no increase in high molecular weight compounds. Although there was an increase (over the starting insulin raw material) in % dimer, % A21 desamido insulin, % late eluting peaks, and % other compounds, the results for all six batches were within USP limits. Retention of insulin potency was 28.3 to 29.9 IU/mg, compared to 28.7 IU/mg for the starting raw material. Residual levels of the polymer used in the process (polyethylene glycol) were below 0.13% to non-detectable, indicating that the polymer is not a significant component of the insulin small spherical particles.

Inter-Batch Reproducibility of Aerodynamic Properties for Insulin Small Spherical Particles There was excellent reproducibility for aerodynamic properties among the six separate batches of insulin small spherical particles produced as demonstrated by Aerosizer and Andersen Cascade Impactor data. For all six batches, the Aerosizer data indicated that over 99.5% of the particles fell within a size range of 0.63 to 3.4 µm, with a minimum of 60% of the small spherical particles falling within a narrow size range of 1.6 to 2.5 µm (FIG. 5). Statistically, the data indicates that one can be 95% confident that at least 99% of the insulin small spherical particles batches produced have at least 96.52% of the particles in the 0.63 to 3.4 µm size range (−68.5% to 70% of the target diameter of 2 µm).

The Andersen Cascade Impactor data corresponded well with the Aerosizer data, with the exception that an average of 17.6% of the dose delivered from the Cyclohaler was deposited in the Mouth and Pre-separator/throat of the apparatus (FIG. 6). The data suggests that the powder dispersion efficiency of the Aerosizer is greater than that of the Cyclohaler device. However, the average emitted dose for the six batches was 71.4% from the Cyclohaler, with 72.8% of the emitted dose deposited on Stage 3 of the impactor. If the respirable fraction for deep lung delivery is estimated to be that fraction with ECD's between 1.1 and 3.3 microns, an average 60.1% of the inhaled insulin small spherical particles may be available for deep lung delivery and subsequent systemic absorption. Excellent reproducibility for the process is shown in Table 1, where the standard deviation values for the MMAD and GSD averages for the six separate batches are extremely low. This indicates that the process variables are under tight control, resulting in batch to batch uniformity for aerodynamic properties.

TABLE 1

Aerodynamic Properties of Insulin Small Spherical Particles

| Parameter | MMAD (µm) | GSD (µm) | % stage 2-F (ECD 3.3 µm) | % stage 3-F (ECD 2.0 µm) | Emitted dose (%) |
|---|---|---|---|---|---|
| Mean | 2.48 | 1.51 | 88.8 | 72.8 | 71.4 |
| SD | 0.100 | 0.064 | 4.58 | 4.07 | 5.37 |

Table 1 shows the aerodynamic properties of Insulin small spherical particles. Results (mean+/−SD) were calculated from analysis of separate insulin small spherical particle batches (N=6) on an Andersen Cascade Impactor. Very good reproducibility for the process is demonstrated by the extremely low standard deviations for the MMAD and GSD.

The insulin small spherical particles produced by this cooling process showed little tendency to agglomerate as evidenced by the aerodynamic data in Table 1.

Example 5

Stirred Vessel Process for Making Insulin Small Spherical Particles 2880 mL of a buffered polymer solution (18.5% polyethylene glycol 3350, 0.7% sodium chloride, in a 0.1 M sodium acetate buffer, pH 5.65 at 2° C.) was added to a glass 3 liter water jacketed stirred vessel and pre-heated to 75° C. 2.4 grams of human zinc crystalline insulin was suspended in a 80 mL of the buffered polymer solution with sonication to ensure complete dispersion. The insulin suspension was added to the stirred, pre-heated buffered polymer solution, and stirred for an additional 5 minutes. The mixture cleared during this time indicating that the zinc crystalline insulin had dissolved. Water from a chiller set to 10° C. was pumped through the jacket of the vessel until the insulin polymer solution dropped to 15-20° C. The resulting suspension was diafiltrated against five volumes of 0.16% sodium acetate—0.026% zinc chloride buffer, pH 7.0, followed by five volumes of deionized water, followed by lyophilization to remove the water. SEM analysis of the lyophilized powder showed uniform small spherical particles with a mean aerodynamic diameter of 1.433 micrometers by TSI Aerosizer time-of flight analysis. Andersen cascade impactor analysis resulted in 73% of the emitted dose deposited on stages 3 to filter, an MMAD of 2.2, and a GSD of 1.6, all indicators of excellent aerodynamic properties of the powder.

Example 6

Reduction in the Formation of Insulin Degradation Products by Adjusting the Ionic Strength of a Small Spherical Particle Producing Formulation Insulin can also be dissolved in the solution at lower initial temperatures, e.g., 75° C., without extended periods of time or an acidic environment, but of which result in significant aggregation, by adding NaCl to the solution.

An improved insulin small spherical particles fabrication process was accomplished using the following technique. A concentrated slurry of zinc crystalline insulin (at room temperature) was added (while stirring) to a 16.7% solution of polyethylene glycol in 0.1 M sodium acetate, pH 5.65, preheated to approximately 85 to 90° C. The insulin crystals dissolved completely in this temperature range within five minutes. The insulin small spherical particles formed as the temperature of the solution was lowered.

Significant formation of $A_{21}$ desamido insulin and insulin dimers due to chemical reactions occurred at initial temperatures of 85-90° C. by the elevated temperatures. However, this required extended periods of time at 75° C. The extended time also resulted in significant insulin degradation. Pre-dissolving the insulin in an acidic environment also caused undesirable conversion of a large percentage of the insulin to an $A_{21}$ desamido insulin degradation product.

In an experiment, sodium chloride was added to the buffered polymer reaction mixture in an effort to reduce the formation of insulin dimers by chemical means. Although the added sodium chloride did not significantly reduce the formation of desamido or dimer insulin degradation products, the addition of sodium chloride greatly reduced the formation of oligomers (high molecular weight insulin products) (Table 2).

TABLE 2

| Sample Description | % dimer | % HMWt. | % desamido | % other related comps. |
|---|---|---|---|---|
| NaCl added to insulin-water suspension | | | | |
| control, no added NaCl | 0.94 | 0.23 | 0.78 | 1.52 |
| NaCl, 0.7% final concentration | 0.83 | 0.05 | 0.82 | 1.43 |
| NaCl added to polymer solution | | | | |
| NaCl, 0.7% final concentration | 0.85 | 0.07 | 0.93 | 1.47 |

In addition, the Zn crystalline insulin dissolved much faster in the presence of NaCl than the control without NaCl. This suggested that addition of sodium chloride improves the rate of solubility of the insulin and allowed a reduction in the temperature used to initially dissolve the zinc insulin crystals. This hypothesis was confirmed in an experiment that demonstrated that the addition of 0.7% NaCl to the formulation allowed the zinc crystalline insulin raw material to dissolve at 75° C. within five minutes, a significantly lower temperature than the 87° C. previously required without NaCl addition. At 75° C., in the absence of NaCl, the insulin did not completely dissolve after 13 minutes.

A series of experiments demonstrated that increasing in the concentration of sodium chloride (2.5 mg/ml, 5.0 mg/ml, 10.0 mg/ml, and 20.0 mg/ml) further reduced the temperature at which the insulin crystals dissolved and also reduced the temperature at which the small spherical particles begin to form (FIGS. 10a-d). Additionally, it was determined that increasing the concentration of the NaCl in the formulation quickly dissolved higher concentrations of Zn crystalline insulin. It was therefore confirmed that the solubility of the insulin at a given temperature could be carefully controlled by adjusting the sodium chloride level of the initial continuous phase. This allows the process to be conducted at temperatures that are less conducive to the formation of degradation products.

In order to determine if the sodium chloride has unique chemical properties that allow the reduction in temperature to dissolve insulin, equimolar concentrations of ammonium chloride and sodium sulfate, were compared to a control with sodium chloride. Both $NH_4Cl$ and $Na_2SO_4$ similarly reduced the temperature required to dissolve the zinc crystalline insulin raw material. The higher ionic strength appears to increase the solubility of the insulin in the microsphere producing formulation, without affecting the ability to form small spherical particles as the solution temperature is reduced.

Example 7

Study of PEG Concentration on Yield and Insulin Concentration and Size of Insulin Small Spherical Particles The polyethylene glycol (3350) titration data shows that increasing the PEG-3350 also increases the yield of small spherical particles. However, when the PEG concentration is too high the particles lose their spherical shape, which cancels out the slight improvement in yield.

The insulin concentration data shows a trend opposite to the PEG, where increasing insulin concentration results in a decrease in yield of small spherical particles.

We do see a general trend that higher concentrations of insulin yield larger diameter small spherical particles. In this experiment, the higher concentrations also resulted in a mix of non-spherical particles with the small spherical particles.

Example 8

Insulin Small Spherical Particles Study with Dogs

The purpose of this experimental study was to conduct a quantification and visualization experiment for aerosolized insulin powder deposition in the lungs of beagle dogs. $^{99m}$Tc labeled Insulin particles made in accordance with the methods disclosed herein. Pulmonary deposition of the aerosolized insulin was evaluated using gamma scintigraphy.

Five beagle dogs were used in this study and each animal received an administration of an $^{99m}$Tc radiolabeled insulin particles aerosol. Dog identification numbers were 101, 102, 103, 104, and 105.

Prior to aerosol administration, the animals were anesthetized with propofol through an infusion line for anesthesia and an endotracheal tube was placed in each animal for aerosol delivery.

Each dog was placed in a "Spangler box" chamber for inhalation of the radiolabeled aerosol. Immediately following the radiolabeled aerosol administration, a gamma camera computer image was acquired for the anterior as well as the posterior thoracic region.

Two in-vitro cascade impactor collections were evaluated, one before the first animal (101) aerosol administration and also following the last animal (105) exposure to establish the stability of the $^{99m}$Tc radiolabeled insulin powder.

The results are illustrated in FIG. 11. The cascade impactor collections in both cases showed a uni-modal distribution.

FIG. 12 shows the results for the P/I ratio computations for all animals. The P/I ratio is a measure of the proportion of the $^{99m}$Tc insulin powder that deposits in the peripheral portions of the lung, i.e., the deep lung. A typical P/I ratio will likely be about 0.7. P/I ratios above 0.7 indicate significant deposition in the peripheral lung compared to central lung or bronchial region.

The scintigraphic image in FIG. 13 shows the insulin deposition locations within the respiratory system and is consistent with the P/I data. (FIG. 12) The scintigraphic image for Dog 101 is representative of all 5 dogs in this study.

The scintigraphic image for Dog 101 shows little tracheal or bronchial deposition with an obvious increase in the deposition in peripheral lung. Radioactivity outside the lung is due to rapid absorption of the $^{99m}$Tc from the deep lung deposition of the aerosolized powder.

The P/I ratios and the image data indicate the $^{99m}$Tc radiolabeled insulin was deposited primarily in the deep lung. The quantity of the radiolabeled insulin deposited into the peripheral lung was indicative of low levels of agglomeration of the particles.

Example 9

Diafiltration Against a Buffer Containing Zinc to Remove Polymer from Insulin Small Spherical Particles Following fabrication of the insulin small spherical particles in the PSEA solution, it was desirable to remove all of the PSEA from the suspension prior to lyophilization. Even a few percent of residual PSEA could act as a binder to form non-friable agglomerates of the small spherical particles. This agglomeration would adversely affect the emitted dose and aerodynamic properties of powder delivered from DPI devices. In addition, lung tissue exposure to repeated doses of a PSEA could raise toxicology issues.

Three techniques were considered for separation of the small spherical particles from the PSEA prior to lyophilization. Filtration could be used to collect small quantities of particles. However, larger quantities of the small spherical particles quickly blocked the pores of the filtration media, making washing and recovery of more than a few milligrams of particles impractical.

Centrifugation to collect the particles, followed by several wash cycles involving re-suspension in a wash solvent and re-centrifugation, was used successfully to remove the PSEA. Deionized water was used as the wash solvent since the insulin small spherical particles were not readily dissolved and the PSEA remained in solution. One disadvantage of centrifugation was that the small spherical particles were compacted into a pellet by the high g-forces required to spin down the particles. With each successive wash, it became increasingly difficult to resuspend the pellets into discrete particles. Agglomeration of the insulin particles was often an unwanted side effect of the centrifugation process.

Diafiltration using hollow fiber cartridges was used as an alternative to centrifugation for washing the insulin small spherical particles. In a conventional set up of the diafiltration apparatus, the buffered PSEA/insulin particle suspension was placed in a sealed container and the suspension was re-circulated through the fibers with sufficient back-pressure to cause the filtrate to pass across the hollow fiber membrane. The re-circulation rate and back pressure were optimized to prevent blockage (polarization) of the pores of the membrane. The volume of filtrate removed from the suspension was continuously replenished by siphoning wash solvent into the stirred sealed container. During the diafiltration process, the concentration of PSEA in the suspension was gradually reduced, and the insulin small spherical particle suspension was essentially PSEA-free after five to seven times the original volume of the suspension was exchanged with the wash solvent over a period of an hour or so.

Although the diafiltration process was very efficient at removing polymer and very amenable to scaling up to commercial quantities, the insulin small spherical particles did slowly dissolve in the deionized water originally used as the wash solvent. Experiments determined that insulin was gradually lost in the filtrate and the insulin particles would completely dissolve after deionized water equivalent to twenty times the original volume of suspension was exchanged. Although the insulin small spherical particles were found to be sparingly soluble in deionized water, the high efficiency of the diafiltration process continually removed soluble insulin, and probably zinc ions, from the suspension. Therefore, the equilibrium between insoluble and soluble insulin concentration in a given volume of deionized water did not occur with diafiltration, a condition that favored dissolution of the insulin.

Table 3 shows various solutions that were evaluated as potential wash media. Ten milligrams of dry insulin small spherical particles were suspended in 1 mL of each solution and gently mixed for 48 hours at room temperature. The percentage of soluble insulin was measured at 24 and 48 hours. The insulin was found to be sparingly soluble in deionized water, with equilibrium reached at just under 1% of the total weight of insulin soluble in less than 24 hours. However, as previously noted, the high efficiency of diafiltration continuously removes the soluble insulin (and zinc) so this equilibrium is never achieved and the insulin small spherical particles would continue to dissolve. Therefore, insulin solubility in the ideal wash solution would be below that of water. Since insulin is least soluble near its isoelectric point, acetate buffers at two molarities and pH 5.65 were examined. The solubility of the insulin was found to be dependent on the molarity of the buffer, and comparable to water at low molarities. Ethanol greatly reduced the solubility of the insulin but only at near anhydrous concentrations. The insulin solubility would actually increase when ethanol mixed with water solutions were used in the PSEA/insulin small spherical particle suspension in the early stages of diafiltration.

TABLE 3

Insulin small spherical particle solubility in various wash solutions

| Wash Solution | % dissolved insulin after 24 hours | % dissolved insulin after 48 hours |
|---|---|---|
| Deionized water | 0.91 | 0.80 |
| 0.1 M sodium acetate, pH 5.65 | 2.48 | 2.92 |
| 0.001 M sodium acetate, pH 5.65 | 0.54 | 0.80 |
| 0.16% sodium acetate-0.016% ZnO, pH 5.3 | 0.14 | 0.11 |
| 0.16% sodium acetate-0.027% ZnCl$_2$, pH 7.0 | 0.09 | 0.06 |
| 50% ethanol/deionized water (v/v) | 9.47 | 9.86 |
| 100% anhydrous ethanol | 0.05 | 0.04 |

Buffer solutions used in commercial zinc crystalline insulin suspensions for injection also contain zinc in solution. Two of these solutions were tested with insulin small spherical particles and found to greatly reduce insulin solubility compared to deionized water. According to the literature, zinc crystalline insulin should have 2 to 4 Zn ions bound to each insulin hexamer. Zinc ions per hexamer ranged from 1.93 to 2.46 for various zinc crystalline insulin preparations used as the raw material for making the insulin small spherical particles. This corresponded to 0.36 to 0.46% zinc per given weight of raw material zinc crystalline insulin. After formation of the insulin small spherical particles and diafiltration against deionized water, 58 to 74% of the zinc was lost during processing. The loss of zinc from the insulin particles would cause increased solubility of the insulin and loss during diafiltration.

Diafiltering the insulin small spherical particles against 0.16% sodium acetate-0.027% $ZnCl_2$, pH 7.0, virtually eliminated insulin loss in the filtrate. Surprisingly however, the zinc content of the insulin small spherical particles increased to nearly 2%, well above the 0.46% measured for the starting zinc crystalline insulin raw material. Another unexpected result of diafiltration against zinc containing buffer was a dramatic improvement in the emitted dose observed from a Cyclohaler DPI device (68% diafiltered against deionized water versus 84 to 90% after zinc buffer diafiltration) and a decrease in the amount of insulin particles deposited in the throat of the Andersen Cascade Impactor. The zinc buffer diafiltration improved the dispersability of the insulin small spherical particle dry powder and reduced agglomeration of the particles, resulting in lower MMAD's and higher deposition on lower stages of the impactor. This suggested that the zinc buffer diafiltration and higher zinc content in the insulin small spherical particles could improve the percent of the dose deposited in the deep lung.

When suspended in the propellant HFA-134a without added excipients for use in an MDI application, there was no apparent irreversible agglomeration of the zinc buffer washed insulin small spherical particles. The insulin particles did flocculate out of suspension in less than a minute, but readily resuspended when shaken just before use. Shaking the MDI container just before use is normally part of the instructions given for using any MDI product. In fact, the loose flocculated particles that settle on the bottom of the MDI container may actually inhibit long term agglomeration of the insulin particles (in addition to the minimal contact due to their spherical shape) since the particles do not settle into a densely packed layer on the bottom of the MDI pressurized container. Therefore, properties imparted by the zinc buffer diafiltration of the insulin small particles may improve the long term shelf life and dispersability of MDI preparations for insulin and other zinc binding compounds.

Since the insulin small spherical particles were found to be noncrystalline by XRPD analysis, the zinc binding was not associated with zinc ion coordination of insulin monomers to form hexamers. Therefore, the non-specific binding of ions and resulting potential benefits could extend to the binding of ions other than zinc. Different proteins that do not bind zinc could bind other ions that would reduce solubility in the diafiltration process and impart similar beneficial effects.

The small spherical particles were suspended in Hydro Fluro Alkane (HFA) 134a propellant at a concentration of 10 mg/mL. The chemical stability of the insulin after storage in the HFA 134a was assessed at time 0 and at one month. The data shown in FIG. 28 shows the preservation of the insulin microspheres in terms of monomeric insulin, insulin dimer, insulin oligomers, insulin main peak and A21-desamindo insulin.

In the following study, insulin small spherical particles prepared according to the methods in Example 4 were compared as to their performance in three different inhalation devices using the Andersen Cascade Impactor method. The Cyclohaler device is a commercial dry powder inhaler (DPI), the Disphaler is another dry powder inhaler and the metered dose inhaler (MDI) is a device in which the microspheres are suspended in HFA 134a as described in this example and are propelled through a 100 microliter or other sized metering valve. The results in FIG. 29 clearly show that the small spherical particles impacting the stages of the Andersen Cascade Impactor device deposit on stages 3 and 4. This is indicative of a very reproducible performance of the small spherical particles regardless of the device used as an inhaler. The only major difference between the DPI and MDI devices is the significantly greater quantity of small spherical particles deposited in the throat section of Andersen Cascade Impactor using the MDI. The high velocity that the MDI device propels the small spherical particles against the throat of the Andersen Impactor explains the higher proportion of insulin microspheres deposited compared to the DPI devices. It can be assumed by those skilled in the art that an MDI device with an attenuated or modified exit velocity could be used to decrease the number of the small spherical particles depositing in the throat. Additional measures could be the use of spacer devices at the end of the MDI.

Insulin small spherical particles (Lot number YQ010302) were fabricated from lyophilized insulin starting material according to the methods described in this example. One year storage stability for the insulin small spherical particles was compared with the lyophilized insulin starting material at 25° C. and 37° C. The insulin stability was compared by examining Total Related Insulin Compounds, Insulin Dimers and Oligomers and A21-desamido Insulin.

FIGS. 30-35 show that over a one year period, the insulin small spherical particles exhibited significantly lower amounts of Insulin Dimers and Oligomers, A21-desamido Insulin and Total Related Insulin Compounds and compared to insulin starting material stored under the same conditions. This indicates that the microsphere form of insulin is significantly more stable to chemical changes than the starting material.

Insulin small spherical particles were tested in the Andersen Cascade Impactor study at 0 time and 10 months after manufacture. A Cyclohaler DPI device was used to determine the aerodynamic stability after long term storage. FIG. 36 shows that the aerodynamic performance remains remarkably consistent after 10 months storage.

Raman spectroscopic investigation was undertaken to elucidate structural differences between unprocessed insulin sample and the insulin in the small spherical particles prepared in this Example. It was shown that the insulin in the small spherical particles possess substantially higher β-sheet content and subsequently lower α-helix content than their parent unprocessed insulin sample. These findings are consistent with the formation of aggregated microfibril structures in small spherical particles. However, when dissolved in an aqueous medium, the spectra reveal essentially identical protein structures resulting from either unprocessed microspheres or insulin, indicating that any structural changes in microspheres are fully reversible upon dissolution.

Two batches of insulin were tested using Raman spectroscopy: A) unprocessed Insulin USP (Intergen, Cat N. 4502-10, Lot# XDH 1350110) and B) Insulin in the small spherical particles (JKPL072502-2 NB 32: P. 64). The powderous samples or insulin solutions (about 15 mg/mL in 0.01 M HCl) were packed into standard glass capillaries and thermostated at 12° C. for Raman analysis. Typically, a 2-15 μL aliquot was sufficient to fill the portion of the sample capillary exposed to laser illumination. Spectra were excited at 514.5 nm with an argon laser (Coherent Innova 70-4 Argon Ion Laser, Coherent Inc., Santa Clara, Calif.) and recorded on a scanning double spectrometer (Ramalog V/VI, Spex Industries, Edison, N.J.) with photon-counting detector (Model R928P, Hamamatsu, Middlesex, N.J.). Data at 1.0 $cm^{-1}$ intervals were collected with an integration time of 1.5 s and a spectral slit width of 8 $cm^{-1}$. Samples were scanned repetitively, and individual scans were displayed and examined prior to averaging. Typically, at least 4 scans of each sample were collected. The spectrometer was calibrated with indene and carbon tetrachloride. Spectra were compared by digital difference methods using SpectraCalc and GRAMS/AI Version 7 software (Thermo Galactic, Salem, N.H.). The spectra were corrected for contributions of solvent (if any) and background. The solutions' spectra were corrected by acquiring 0.01M HCl spectrum under identical conditions and fit with a series of five overlapping Gaussian-Lorentzian functions situated on a sloping background [S.-D. Yeo, P. G. Debenedetti, S. Y. Patro, T. M. Przybycien, J. Pharm. Sci., 1994, 83, 1651-1656]. The fitting was performed in the 1500-1800 $cm^{-1}$ region.

Raman spectra were obtained for both powderous insulin samples and their respective solutions (FIG. 10$i$). The spectrum of the un-processed sample corresponds to the previously described spectra of the commercial insulin samples very well [S.-D. Yeo, P. G. Debenedetti, S. Y. Patro, T. M. Przybycien, J. Pharm. Sci., 1994, 83, 1651-1656; J. L. Lippert, D. Tyminski, P. J. Desmueles, J. Amer. Chem. Soc., 1976, 98, 7075-7080]. The small spherical particle sample exhibited a pronounced (about +10 to +15 $cm^{-1}$) shift in the amide I mode, indicative of a significant perturbation in the secondary structure of the protein. Notably, however, spectra of the commercial powder and small spherical particles were virtually identical when the samples were dissolved in the aqueous medium, indicating that the changes in the secondary structure upon processing were completely reversible.

The secondary structural parameters were estimated using the computing algorithm that included smoothing, subtraction of the fluorescence and aromatic background, and the amide I bands deconvolution. The exponentially decaying fluorescence was subtracted essentially as described elsewhere [S.-D. Yeo, P. G. Debenedetti, S. Y. Patro, T. M. Przybycien, J. Pharm. Sci., 1994, 83, 1651-1656]. The estimated structural parameters are collected in Table 4.

TABLE 4

Structural parameters of insulin samples estimated from Raman spectra.

| Sample | Total α-helix content, % | Total β-sheet content, % | β-Reverse turn, % | Random coil, % |
|---|---|---|---|---|
| Unprocessed, Powder | 44 | 31 | 14 | 11 |
| Unprocessed insulin in solution | 44 | 28 | 11 | 17 |
| small spherical particles, powder | 11 | 67 | 15 | 7 |
| small spherical particles in solution | 44 | 30 | 11 | 15 |

Example 10

Preparation of Small Spherical Particles of Human Insulin by an Isothermal Method Human insulin USP (Intergen) was dispersed in a NaCl and PEG (MW 3350, Spectrum Lot# RP0741) solution resulting in final insulin concentration of 0.86 mg/mL, and 0.7 wt % NaCl and 8.3 wt % PEG concentrations. The pH was adjusted to 5.65 by addition of minute amounts of glacial acetic acid and 1 M NaOH solutions. After heating to $T_1$=77° C., clear protein solutions were obtained resulting in the insulin concentration $C_{eq}$. Then the solutions were cooled at a predetermined rate to a temperature $T_2$=37° C. At the $T_2$, protein precipitation was observed. The precipitates were removed by centrifugation (13,000×g, 3 min), again at temperature 37° C., and the insulin concentration (C*) in the resulting supernatant was determined by bicinchoninic protein assay to be 0.45 mg/mL. Thus prepared insulin solution that is kept at 37° C. is designated Solution A.

Solution B was prepared by dissolution of human insulin in 0.7 wt % NaCl/8.3 wt % PEG (pH brought to about 2.1 by HCl addition) resulting in 2 mg/mL insulin concentration. The solution was incubated at 37° C. with stirring for 7 h and subsequently sonicated for 2 min. Aliquots of the resulting Solution B were added to Solution A resulting in total insulin concentration of 1 mg/mL. The resulting mixture was kept under vigorous stirring at 37° C. overnight resulting in insulin precipitates, which were gently removed from the liquid by using a membrane filter (effective pore diameter, 0.22 μm). The resulting protein microparticles were then snap-frozen in liquid nitrogen and lyophilized.

B. Small Spherical Particles of Alpha-1-Antitrypsin (AAT)

The present invention can also be used to prepare small spherical particles of AAT which are particularly suitable for pulmonary delivery.

Example 11

Jacketed Column Batch Preparation of AAT Small Spherical Particles (10-300 mg Scale)

A solution buffered at pH 6.0 with 10 mM ammonium acetate containing 16% PEG 3350 and 0.02% Pluronic F-68 was mixed with a magnetic stirbar in a jacketed beaker and heated to 30° C. The beaker temperature was controlled using a circulating water bath. A concentrated solution of recombinant AAT (rAAT) was added to this solution while stirring and the pH was adjusted to 6.0. The rAAT concentration in the final solution was 2 mg/ml. The rAAT was completely soluble at this temperature in this solution composition. The entire contents of the vessel were transferred to a jacketed column and heated to 25-30° C. The circulating water bath for the column was set to ramp down to −5° C. The column and contents were cooled at approximately 1° C./minute to a temperature of about 4° C. The rAAT small spherical particles formed during the cooling step. The microsphere suspension was frozen in glass crystallizing dishes and lyophilized to remove the water and buffer.

In order to extract PEG from the protein small spherical particles after lyophilization, the PEG/protein cake was washed with methylene chloride ($MeCl_2$). Another washing media utilized was methylene chloride:acetone 1:1, or methylene chloride:pentane 1:1. The washing procedure was repeated for a total of 3 times the original volume washes. The final pellet was resuspended in a small volume of acetone or pentane and dried by either direct exposure to nitrogen gas or by rotary evaporation.

Example 12

Jacketed Vessel Batch Preparation of AAT Small Spherical Particles (200-2000 mg Scale)

This type of preparation was done using the same formulation composition as the jacketed column but capable of accommodating larger volumes and was more suitable for scale-up. At this scale, the formulation was mixed at 75 rpm with an A-shaped paddle style impeller in a jacketed vessel, usually 500-1000 ml, and heated to 30° C. The vessel temperature was controlled using a circulating water bath. Keeping the solution in the same vessel, the water bath source was switched from a 30° C. bath to a 2° C. bath. The vessel and contents were cooled at approximately 1° C./minute to a temperature of 4° C. The rAAT small spherical particles formed during the cooling step. The temperature was monitored using a thermocouple, and when the suspension reached 4° C., it was held close to this temperature for an additional 30 minutes. After the hold step, the small spherical particle suspension was concentrated via diafiltration at around 4° C. to remove approximately 75% of the polymer and volume. The remaining small spherical particle suspension was frozen as a thin layer in a precooled lyophilization tray and lyophilized to remove the water and remaining buffer.

The protein small spherical particles were separated from the remaining dried polymer either by centrifugation with organic solvents (as described in Example 10) or by supercritical fluid (SCF) extraction. For SCF extraction, the dried material was transferred into a high pressure extraction chamber, which was pressurized to 2500 psi (at room temperature) with $CO_2$. Once operating pressure was reached, ethanol was introduced to the inlet fluid stream as a 70:30 $CO_2$:ethanol mix. This super critical fluid dissolved the polymer, leaving the small spherical particles. At the conclusion of the process, the system was flushed of ethanol and slowly decompressed.

Example 13

Process Yield—% Conversion of rAAT into Small Spherical Particles

Small spherical particles were fabricated as described in Examples 10 and 11. After the cooling process was complete, a small aliquot of the suspension was removed and filtered through a 0.2 μm syringe filter to remove the solid small spherical particles. The absorbance of the filtrate, which was the rAAT remaining in solution, was determined at 280 nm using a UV spectrophotometer. The rAAT concentration was then calculated from a standard curve. The % conversion was calculated as:

$$\frac{(\text{Starting rAAT concentration} - \text{filtrate rAAT concentration})}{\text{Starting rAAT concentration}} * 100\% = \% \text{ conversion}$$

| Scale | % conversion to small spherical particles |
|---|---|
| 100-200 mg (n = 9, column) | 91.7 ± 4.4 |
| 300 mg (n = 4, column) | 93.4 ± 1.6 |
| 2 g = 5, vessel | 90.4 ± 1.8 |

As shown in the above table, a high percentage of the AAT protein was converted into small spherical particles irrespective of the process scale.

Example 14

Particle Size Distribution of AAT Particles at Different Process Scales

Aerosizer Data

A sample of the final AAT dry powder small spherical particles was analyzed in a TSI Aerosizer 3225, which measures particle size by time of flight measurements. From these measurements, different ratios of volume diameters were calculated to demonstrate the particle size distribution of the AAT small spherical particles and were used to compare to particles fabricated by methods other than that of the present invention.

| Scale | d90/d10 (volume) | d80/d20 (volume) | (d90-d10)/d50 (volume) |
|---|---|---|---|
| 5-10 mg (n = 12, column) | 1.88 ± 0.20 | 1.49 ± 0.10 | 0.67 ± 0.14 |
| 100-200 mg (n = 5, column) | 1.83 ± 0.05 | 1.41 ± 0.05 | 0.66 ± 0.05 |
| 300 mg (n = 3, column) | 2.05 ± 0.17 | 1.61 ± 0.11 | 0.77 ± 0.06 |
| 1-2 g (n = 4, vessel) | 2.21 ± 0.30 | 1.60 ± 0.11 | 0.86 ± 0.19 |

Andersen Data

A 5-10 mg sample was weighed into a gel capsule and administered into the Andersen Cascade Impactor using the Cyclohaler Dry Powder Inhaler at a flow rate of 60 liters per minute (LPM). Small spherical particles were collected from all impactor stages, dissolved in 0.2M Tris-HCl buffer at pH 8.0, and quantitated using reverse phase HPLC. The data was analyzed and the geometric standard deviation (GSD) calculated as described in the United States Pharmacopeia (USP). The data demonstrated the narrow size distribution.

| Scale | GSD |
|---|---|
| 100-200 mg (n = 5, column) | 1.74 ± 0.22 |
| 300 mg (n = 3, column) | 1.77 ± 0.40 |
| 2 g (n = 5, vessel) | 1.70 ± 0.09 |

All of the distribution parameters shown above demonstrated the excellent particle size distribution that results from the fabrication method of the present invention.

Example 15

Retention of AAT Bioactivity

To determine the specific activity, the rAAT small spherical particles were dissolved in 0.2M Tris-HCl pH 8.0 at room temperature. The resulting solution was analyzed by an assay which measures the capacity of rAAT to inhibit the ability of porcine pancreatic elastase (PPE) to hydrolyze synthetic peptides that contain a p-nitroanilide group at their C-terminus. The same solution of rAAT small spherical particles was then assayed for protein concentration using the Bicinchoninic Acid (BCA) assay. A control rAAT starting material solution was also analyzed in both assays. Because the activity assay was developed to determine the activity based on a concentration of 1 mg/ml protein per sample, the activity value was corrected based on the actual protein concentration as determined by BCA, giving the specific activity value:

$$\frac{\text{activity value for sample}}{\text{actual protein concentration}} = \text{specific activity for sample}$$

Inhibition of Porcine Pancreatic Elastase by rAAT

| Scale | IU/mg small spherical particles | IU/mg control |
|---|---|---|
| 100-300 mg (n = 12, column) | 64.19 ± 5.01 | 64.34 ± 4.95 |
| 200-300 mg (n = 8, vessel) | 62.53 ± 5.29 | 65.87 ± 0.98 |

The specific activity thus demonstrated the retention of bioactivity after fabrication of AAT into small spherical particles.

Example 16

Retention of AAT Structural Integrity

One of the central differentiating points of controlled phase separation (CPS) technology is the formation of particles under mild conditions utilizing aqueous systems during particle formation and avoiding other stress-inducing conditions such as increased temperature, shear, etc. In the particle engineering field, major concerns are the stability of proteins during the fabrication and the storage stability. The main degradation pathways such as oxidation, deamidation and especially aggregation of proteins are believed to be responsible for protein formulation side effects including immunogenicity. Therefore, regulatory concerns require an extremely low level of degradation products in final particle formulations. HPLC, physical chemical characterization such as CD and DSC were utilized to determine whether protein modification occurred during formation.

Circular Dichroism (CD) is the most commonly used method for evaluation of structural changes in a protein subjected to perturbation, or comparison of the structure of an engineered protein to the parent protein. The CD method is assessing protein folding, and protein secondary and tertiary structure.

Secondary structure can be determined by CD spectroscopy in the "far-UV" spectral region (190-250 nm). At these wavelengths, the chromophore is the peptide bond when it is located in a regular, folded environment. Alpha-helix, beta-sheet, and random coil structures each give rise to a characteristic shape and magnitude of CD spectrum. The approximate fraction of each secondary structure type that is present in any protein can thus be determined by analyzing its far-UV CD spectrum as a sum of fractional multiples of such reference spectra for each structural type.

The CD spectrum of a protein in the "near-UV" spectral region (250-350 nm) can be sensitive to certain aspects of tertiary structure. At these wavelengths the chromophores are the aromatic amino acids and disulfide bonds, and the CD signals they produce are sensitive to the overall tertiary structure of the protein. Signals in the region from 250-270 nm are attributable to phenylalanine residues, signals from 270-290 nm are attributable to tyrosine, and those from 280-300 nm are attributable to tryptophan. Disulfide bonds give rise to broad weak signals throughout the near-UV spectrum.

Far-UV CD spectra of the rAAT stock solution and AAT released from small spherical particles in phosphate buffer (pH 7.4, T=25° C., protein concentration 0.05 mg/mL) are shown in FIG. 13. Each spectrum represents the average of 10 scans.

Far-UV CD spectra of the rAAT stock solution and AAT released from small spherical particles in phosphate buffer (pH 7.4, T=25° C., protein concentration 0.05 mg/mL) are shown in FIG. 14a. Each spectrum represents the average of 10 scans.

RP-HPLC

Small spherical particles were dissolved in 0.2M Tris-HCl at pH 8.0 and analyzed by reverse-phase HPLC. When compared to a control solution of starting rAAT protein, there is no apparent difference in the appearance of the chromatograms.

HPLC System:
HPLC Column—Pheomenex Jupiter, 5 micron, C4, 300A, 250×4.6 mm
Waters Alliance 2965 Pump/autosampler
Wavelength—280 nm
Injection Volume—75 ul
Gradient of Concentration:
Mobile phase 1: 0.1% TFA in water
Mobile phase 2: 0.085% TFA in 90% (c/v) acetonitrile in water
Run time—60 min
Flow rate—1.0 ml/min
DSC
DSC diagrams were generated. See FIGS. 15-25b.

Example 17

Storage Stability of AAT Small Spherical Particles Relative to that of AAT Starting Material Small spherical particles were analyzed for retention of bioactivity (using the assay described in Example 15) after storage at room temperature and 4° C. for 1 week, 1 month, 2 months, 3 months, 6 months, and 12 months. (FIGS. 14b and 14c.) The bulk material is rAAT starting solution which has been dialyzed and then lyophilized. For each time point and storage condition, there were duplicate samples which were each assayed in duplicate.

C. Small Spherical Particles of Human Growth Hormone (hGH)

The present invention can also be used to prepare small spherical particles of hGH.

Example 18

Test Tube Batch Preparation (20-50 mg Scale) of Small Spherical Particles of hGH A solution buffered at pH 5.6 (50 mM ammonium acetate/50 mM ammonium bicarbonate) containing 18% PEG 3350, with a final concentration of hGH in the solution of 1 mg/ml was mixed in a 50 ml conical tube and heated in a stationary water bath to 58° C. The hGH dissolved in the solution under these conditions. The tube was then removed from the water bath and cooled in an ice bath until the solution reached 110° C. The cooling rate was maintained at 4-6° C./min. hGH protein small spherical particles are formed during the cooling step. Small spherical particles started to form when the temperature of the solution reached about 40° C. After particle formation, the hGH protein small spherical particles were separated from the PEG by one of two methods, which are described below.

Organic solvent washing requires that after the cooling step and particle formation, the small spherical particle suspension was flash frozen with liquid nitrogen, and lyophilized to remove water and buffer. In order to separate the protein small spherical particles from the PEG after lyophilization, the PEG/protein cake was suspended in methylene chloride ($MeCl_2$). PEG is soluble in $MeCl_2$ while the protein small spherical particles are insoluble. The suspension was mixed at room temperature for 5 minutes. Since the density of the hGH small spherical particles is close to that of $MeCl_2$ (d=1.335 g/ml), a second solvent was necessary to lower the liquid density to facilitate centrifugation. Acetone, which is miscible with $MeCl_2$, was added in a volume equal to that of $MeCl_2$. The small spherical particles suspension was then centrifuged at 3300 rpm for 5 minutes at room temperature. The supernatant was discarded, and the pellet resuspended in $MeCl_2$ and mixed again for 5 minutes at room temperature. This washing procedure was repeated for a total of 5 washes. After the final wash, the pellet was resuspended in a small volume of $MeCl_2$ and dried by rotary evaporation, leaving a final powder of hGH small spherical particles.

The zinc buffer washing required that after the cooling step and particle formation, the small spherical particles suspension was centrifuged at 4000 rpm for 10 minutes at 4° C. to separate the small spherical particles from PEG. The supernatant was removed, and the pellet was resuspended in cold buffer containing 50 mM zinc acetate, in a volume equal to that of the supernatant that was removed. The $Zn^{2+}$ ion reduced the solubility of the hGH and prevented dissolution during washing. The wash buffer was kept on ice. The suspension was then centrifuged immediately at 3000 rpm for 5 minutes at 4° C. The supernatant was removed and the zinc buffer wash repeated for a total of 3 times. Following 3 times zinc buffer wash, the pellet was washed 2 times in water and centrifuged at 3000 rpm for 5 minutes at 4° C. to remove excess zinc. Following the final water wash, the pellet was resuspended in a small volume of water and flash frozen using liquid nitrogen. The frozen pellet was then lyophilized to remove water, leaving a final powder of hGH small spherical particles.

Example 19

Jacketed Vessel Batch Preparation (100 mg Scale) of Small Spherical Particles of hGH This type of preparation was done using a similar formulation composition as Example 18, but can accommodate larger volumes and is more suitable for scale-up.

A solution buffered at pH 6.1 (80 mM ammonium acetate/ 10 mM ammonium bicarbonate) containing 18% PEG 3350 and 0.02% Pluronic F-68 was mixed in a jacketed beaker by means of an overhead impellar, and heated to 58° C. The mixture temperature was controlled using a circulating water bath. A concentrated solution of hGH was added to this solution while stirring. The final concentration of hGH in the solution was 1 mg/ml. The hGH was completely soluble at this temperature in this solution composition. The vessel and contents were then cooled at a rate of 8° C./minute to a temperature of approximately 10° C. The hGH small spherical particles formed during the cooling step. The small spherical particles started to form around 40° C., and the process continued as the suspension was cooled further. After the cooling step, the small spherical particles were separated from PEG by one of the two methods described in Example 20a.

Example 20

Retention of Integrity of hGH

The protein integrity of hGH in small spherical particles was evaluated at the following stages of the process: post particle formation, post PEG extraction, and post solvent removal or post drying. Measurement of the chemical integrity of the hGH after fabrication into small spherical particles was determined using HPLC assays (Size Exclusion Chromatography (SEC), Reverse Phase (RP)) to quantitate agglomeration and degradation products. Results demonstrated that there was no significant accumulation of agglomerates or other related substances during the small spherical particle formulation process.

a. Organic Solvent Wash

| hGH Agglomeration by Size Exclusion: Increase in agglomeration over starting material | | |
|---|---|---|
| Stage of process | % increase in dimer | % increase in HMW species |
| after particle formation | 1.17 | 0 |
| after PEG extraction and drying | 2.67 | 0.43 |

| hGH Related Substances by Reverse Phase: Increase in degradation over starting material | | | |
|---|---|---|---|
| Stage of process | % increase in early eluting species | % increase in desamido | % increase in late eluting species |
| after particle formation | 0.22 | 0.66 | 0 |
| after PEG extraction and drying | 1.29 | 2.93 | 0 | b. Zinc Buffer Wash

| hGH Agglomeration by Size Exclusion: Increase in agglomeration over starting material | | |
|---|---|---|
| Stage of process | % increase in dimer | % increase in HMW species |
| after particle formation | 0.88 | 0 |
| after PEG extraction | 2.25 | 0 |
| after [article drying | 2.51 | 0 |

| hGH Related Substances by Reverse Phase: Increase in degradation over starting material | | | |
|---|---|---|---|
| Stage of process | % increase in early eluting species | % increase in desamido | % increase in late eluting species |
| after particle formation | 0.38 | 1.91 | 0.26 |
| after PEG extraction | 0.19 | 1.34 | 0.26 |
| after particle drying | 0.34 | 1.58 | 0.37 |

Example 21

Particle Size Distribution of Small Spherical Particles of hGH

Characterization of the particle size distribution of the small spherical particles was determined by aerodynamic time-of-flight measurements using a TSI Aerosizer (FIG. 26) and by scanning electron microscopy (FIG. 27).

Example 22

Dissolution Kinetics of hGH Small Spherical Particles

Dissolution kinetics of hGH small spherical particles exposed to two different extraction procedures were compared.

hGH small spherical particles washed with organic solvent dissolved immediately in aqueous media, similar to hGH starting material.

When hGH small spherical particles were washed with zinc buffer, solubility was reduced (FIG. 28). Dissolution of hGH small spherical particles was carried out in 10 mM Tris, 154 mM NaCl, 0.05% Brij 35, pH 7.5, at 37° C. More complete release of the protein has been achieved in other media in vitro. Dissolution kinetics demonstrated that approximately 30% of the total hGH was released in the first 15 minutes, and approximately 50% was released in the first 24 hours. The protein release reached completion at 1 month. The fact that small spherical particle dissolution proceeded in a two-phase manner may result in some delayed release in vivo.

D. Lysozyme Small Spherical Particles

Example 23

Preparation of Small Spherical Particles of Lysozyme

A solution of: 1.6 mg/ml lysozyme, 13.2% PEG 3350, 55 mM ammonium acetate pH 9.5, 53 mM ammonium sulfate, 263 mM sodium chloride, 26 mM calcium chloride.

The PEG and buffer was heated to 40° C. (pH 9.55. The resulting suspension was flash frozen in liquid nitrogen and lyophilized on the manifold lyophilizer. Small spherical particles were formed.

E. DNase Small Spherical Particles

Example 24

Preparation of Small Spherical Particles of DNase

Formulation example: A solution of: 0.18 mg/ml DNase (from stock 1 mg/ml), 18.2% PEG 3350 (from stock 25%), 9 mM ammonium acetate, pH 5.15 (from stock 1M).

This suspension was cooled in the −80° C. freezer and, once frozen, was lyophilized on a manifold lyophilizer, and subsequently washed by centrifugation with MeCl$_2$/acetone.

Initial concentrations tried were 0.1 mg/ml DNase and 20% PEG 3350. But after trying to cool from 37° C. to 0° C. and not getting a precipitate, another amount of DNase was added to get the above concentrations. This solution was cooled in the −80° C. freezer and, once frozen, was lyophilized on the manifold lyophilizer. Washed by centrifugation with MeCl$_2$/acetone. Initial concentrations tried were 0.1 mg/ml DNase and 20% PEG 3350. But after trying to cool from 37° C. to 0° C. and not getting a precipitate, another amount of DNase was added to get the above concentrations. This solution was cooled in the −80° C. freezer and, once frozen, was lyophilized on the manifold lyophilizer. Washed by centrifugation with MeCl$_2$/acetone. (FIGS. 37, 38).

Activity (Assay for DNase-I using DNA-Methyl Green, purchased from Sigma).

The theoretical activity for the starting material is listed as 775 Ku/mg protein. The stock solution was determined to be 0.145 mg/ml protein. This concentration was diluted into 5 ml for a final concentration of 0.0199 mg/ml. The activity should be 775 Ku/mg*0.0199 mg/ml=15.46 Ku/ml.

$$\textit{Kunitz units/ml of solution} = \frac{\Delta A640 \text{ per min of unknown} \times 40 \times \text{dilution factor}}{\Delta A640 \text{ per min of known}}$$

Ku/ml=−0.0004×40×1/−0.0011=14.55 Ku/ml

Compare to theoretical:

Small Spherical Particles/theoretical*100%=% activity 14.55 Ku/ml/15.46 Ku/ml*100%=94.1%

F. Superoxide Dismutase Small Spherical Particles

Example 25

Preparation of Small Spherical Particles of Superoxide Dismutase

A solution of 0.68 mg/ml SOD (from stock 5 mg/ml), 24.15% PEG 3350 (from stock 31.25%), 9.1 mM ammonium acetate (from stock 1M), Final pH=4.99, adjusted with ammonium hydroxide and acetic acid. The solution was cooled from 40° C. to 0° C. over 50 minutes (~0.8° C./min) and precipitation initiated around 25° C. The suspension was flash froze in liquid nitrogen, and lyophilized on manifold a lyophilizer, and subsequently washed by centrifugation with MeCl$_2$/acetone. (FIGS. 39, 40).

Cooled from 40° C. to 0° C. over 50 minutes (~0.8° C./min). Started precipitating around 25° C. Flash froze in liquid nitrogen, and lyophilized on manifold lyophilizer. Washed by centrifugation with MeCl$_2$/acetone. Small spherical particles were formed and the majority of acetone was retained.

G. Subtilisin Small Spherical Particles

Example 26

Subtilisin Small Spherical Particles Using Non-Polymer Phase-Separation Enhancing Agents The continuous phase of the initial system may contain a non-polymer phase-separation enhancing agent to induce phase separation of a protein during cooling. Subtilisin small spherical particles can be formed according to the present invention using a mixture of propylene glycol and ethanol without the use of any polymers. Propylene glycol serves as a freezing point depression agent and ethanol serves as the phase-separation enhancing agent in this system. Propylene glycol also aids in the formation of a spherical shape of the small spherical particles.

A 20 mg/mL subtilisin solution in 35% propylene glycol—10% Formate—0.02% CaCl$_2$ was prepared. The 35% propylene glycol-subtilisin solution was then brought to 67% ethanol while mixing. The solution remained clear at room temperature. However, when cooled to −20° C. for one hour, a suspension of particles formed. After centrifugation to collect the particles and washing with 90% ethanol, Coulter Particle Size analysis was performed, with absolute ethanol as the suspension fluid. The particles yielded Coulter results consistent with discrete particles having an average diameter of 2.2 microns and 95% of the particles were between 0.46 and 3.94 microns. Light microscopy evaluation confirmed these results showing substantially spherical particles. SEM analysis of the particles confirmed the Coulter results.

Retention of Subtilisin Enzymatic Activity after Formation of Small Spherical Particles The retention of enzyme activity after conversion of subtilisin in solution to subtilisin small spherical particles was confirmed by a colorimetric assay. The theoretical total units of activity for the small spherical particles were calculated by subtracting the total units found in the supernatant (after separation of the subtilisin particles) from the total units of subtilisin assayed in the ethanol-subtilisin-propylene glycol solution prior to cooling. The actual total units found for the subtilisin small spherical particles divided by the theoretical units expressed as a percentage represents the retention of subtilisin activity after particle formation. By this calculation, 107% of the theoretical subtilisin activity was retained after formation of the subtilisin small spherical particles.

H. Carbohydrate Small Spherical Particles

Example 27

Formation of Carbohydrate Small Spherical Particles

Figure 49:
FIG. 49 is an SEM of the particles of Example 27.

The present invention can be applied to the preparation of carbohydrate small spherical particles. Phase separation can be induced between a PEG phase and a dextran phase during the cooling of the system. Dextrans of various molecular weights can be used, e.g., 5K, 40K, 144K, and 500K. The mixture of 5 mg/ml dextran 40 K in 30% PEG 300 was equilibrated at 35° C., then the mixture was cooled to 0° C. and lyophilized. Particles were harvested by washing the mixture with methylene chloride: acetone (1:1) and centrifugation. As can be seen from FIG. 49, small spherical particles were formed. Other carbohydrates such as starch, hydroxyethyl starch, trehalose, lactose, mannitol, sorbitol, hylose, dextran sulfate, etc. can be formulated into small spherical particles using this process.

I. Microencapsulation of Pre-Fabricated Small Spherical Particles

Example 28

Preparation of PLGA-Encapsulated Pre-Fabricated Insulin Small Spherical Particles a) A 20% (w/v) polymer solution (8 ml) was prepared by dissolving 1600 mg of a Polylactide-co-glycolide (PLGA, MW 35 k) in methylene chloride. To this solution was added 100 mg of insulin small spherical particles (INSms), and a homogenous suspension was obtained my vigorous mixing of the medium using a rotor/stator homogenizer at 11 k rpm. The continuous phase consisted of 0.02% aqueous solution of methylcellulose (24 ml) saturated with methylene chloride. The continuous phase was mixed at 11 k rpm using the same homogenizer, and the described suspension was gradually injected to the medium to generate the embryonic microencapsulated particles of the organic phase. This emulsion has an O/W ratio of 1:3. The emulsification was continued for 5 minutes. Next, the emulsion was immediately transferred into the hardening medium consisted of 150 ml deionized (DI) water, while the medium was stirred at 400 rpm. The organic solvent was extracted over one hour under reduced pressure at −0.7 bar. The hardened microencapsulated particles were collected by filtration and washed with water. The washed microencapsulated particles were lyophilized to remove the excess water. The resultant microencapsulated particles had an average particle size of about 30 μm with majority of the particle population being less than 90 μm, and contained 5.7% (w/w) insulin.

b) A 30% (w/v) polymer solution (4 ml) was prepared by dissolving 1200 mg of a 50:50 polylactide-co-glycolide (PLGA, MW 35 k) in methylene chloride. Next a suspension of 100 mg INSms in the described polymer solution was prepared using a homogenizer. This suspension was used to generate the O/W emulsion in 12 ml 0.02% aqueous solution of methylcellulose as described in Example 28 (W/O ratio=1:3). The same procedures as Example 28 are followed to prepare the final microencapsulated particles. The microencapsulated particles formed had an average particle size of 25 μm, ranging from 0.8 to 60 μm. The insulin content of these microencapsulated particles was 8.8% (w/w).

Alternatively, a 10% (w/v) solution of the polymer was used to perform the microencapsulation process under the same conditions described. This process resulted in microencapsulated particles with an average particle size of about 12 μm with most the particles less than 50 μm, and an insulin loading of 21.1% (w/w).

Method for In Vitro Release:

The in vitro release (IVR) of insulin from the microencapsulated particles is achieved by addition of 10 ml of the release buffer (10 mM Tris, 0.05% Brij 35, 0.9% NaCl, pH 7.4) into glass vials containing 3 mg equivalence of encapsulated insulin, incubated at 37° C. At designated time intervals 400 μL of the IVR medium is transferred into a microfuge tube and centrifuged for 2 min at 13 k rpm. The top 300 μL of the supernatant is removed and stored at −80° C. until analyzed. The taken volume was replaced with 300 μL of the fresh medium, which was used to reconstitute the pallet along with the remaining supernatant (100 μL). The suspension is transferred back to the corresponding in vitro release medium.

Example 29

Procedure for Microencapsulation of Pre-Fabricated Insulin Small Spherical Particles in PLGA/PLA Alloy Matrix System A 30% (w/v) solution of a PLGA/PLA alloy was prepared in methylene chloride (4 ml). The alloy consisted of a 50:50 PLGA (MW 35 k), D,L-polylactic acid (PLA, MW 19 k) and poly L-PLA (PLLA, MW 180 k) at 40, 54 and 6% (0.48, 0.68 and 0.07 g), respectively. The same procedures as Example 28b were followed to prepare the final microencapsulated particles. The examples of the microencapsulated particles had a particle size range of 0.8-120 μm, averaging at 40 μm with most of the particles population smaller than 90 μm.

Example 30

Procedure for Microencapsulation of Pre-Fabricated Insulin Small Spherical Particles in PLGA Matrix System, Using PEG in Both Continuous and Discontinuous Phases A solution of 4 ml of 10% 50:50 PLGA (0.4 g) and 25% polyethylene glycol (PEG, MW 8 k) was prepared in methylene chloride. Using a rotor/stator homogenizer, 100 mg of the INSms were suspended in this solution at 11 k rpm. The continuous phase consisted of aqueous solution (12 ml) of 0.02% (w/v) methylcellulose and 25% PEG (MW 8 k) saturated with methylene chloride. The continuous phase was mixed at 11 k rpm using the same homogenizer, and the described suspension was gradually injected to the medium to generate the embryonic microencapsulated particles of the organic phase. This emulsion has an O/W ratio of 1:3. The emulsification was continued for 5 minutes. Then, the emulsion was immediately transferred into the hardening medium consisted of 150 ml DI-water, while the medium was stirred at 400 rpm. The organic solvent was extracted over one hour under reduced pressure at −0.7 bar. The hardened microencapsulated particles were collected by filtration and washed with water. The washed microencapsulated particles were lyophilized to remove the excess water. The microencapsulated particles of this example had an average particle size of 30 μm, ranging from 2 to 90 μm with majority of the population being smaller than 70 μm. The insulin content of these microspheres was 16.0% (w/w).

Example 31

Procedure for Microencapsulation of Pre-Fabricated Insulin Small Spherical Particles in PLGA Matrix System at Various Ph of Continuous Phase, Using Phosphate Buffer A solution of 4 ml of 20% 50:50 35 kD PLGA (0.8 g) was prepared in methylene chloride. Using a rotor/stator homogenizer, 100 mg of the INSms were suspended in this solution at 11 k rpm. The continuous phase consisted of aqueous solution of 0.1% (w/v) methylcellulose and 50 mM phosphate buffer at pH 2.5, 5.4 and 7.8. Microencapsulation was performed using the continuous setup (FIG. 41A). The continuous phase was mixed at 11 k rpm and fed into the emulsification chamber at 12 ml/min. The dispersed phase was injected into the chamber at 2.7 ml/min to generate the embryonic microencapsulated particles. The produced emulsion was removed from the chamber and transferred into the hardening bath in a continuous fashion. The hardening medium was stirred at 400 rpm. The organic solvent was extracted over one hour under reduced pressure at −0.4 bar. The hardened microencapsulated particles were collected by filtration and washed with water. The washed microencapsulated particles were lyophilized to remove the excess water.

The insulin contents of the resultant microencapsulated particles s prepared at pH 2.5, 5.4 and 7.8 were estimated to be 12.5, 11.5 and 10.9, respectively. The results of size distribution analysis of the microencapsulated particles are summarized in Table 5.

TABLE 5

Size distribution of insulin loaded- PLGA microencapsulated particles fabricated at various pH of the continuous phase.

| pH of Continuous Phase | Particle size (μm) | | | |
|---|---|---|---|---|
| | Range | Average | 95% Under | 5% Under |
| 2.5 | 1.4-54 | 24 | 35.9 | 13.8 |
| 5.4 | 0.9-46 | 23 | 33.8 | 11.8 |
| 7.8 | 0.8-25 | 11 | 16.0 | 5.7 |

Method for In Vitro Release:

The in vitro release of insulin from the microencapsulated particles was achieved by addition of 10 ml of the release buffer (10 mM Tris, 0.05% Brij 35, 0.9% NaCl, pH 7.4) into glass vials containing 3 mg equivalence of encapsulated insulin, incubated at 37° C. At designated time intervals 400 μL of the IVR medium was transferred into a microfuge tube and centrifuged for 2 min at 13 k rpm. The top 300 μL of the supernatant was removed and stored at −80° C. until analyzed. The taken volume was replaced with 300 μL of the fresh medium, which was used to reconstitute the pallet along with the remaining supernatant (100 μL). The suspension was transferred back to the corresponding in vitro release medium.

The in vitro release (IVR) results of the above preparations are shown in FIG. 44, and indicate the significant effect of pH of the continuous phase on release kinetics of insulin from the formulations.

Example 32

Procedure for Microencapsulation of Pre-Fabricated Human Serum Albumin (HSA) Small Spherical Particles in PLLA or PLLA/PEG Matrix System A solution of 2 ml of 25% (w/v, 500 mg) PEG (MW 3 k or 8 k) was prepared in methylene chloride. The PEG solution or 2 ml of methylene chloride was used to form a suspension of 50 mg pre-fabricated human serum albumin small spherical particles (HSAms), using a rotor/stator homogenizer at 11 k rpm. To this suspension was added 2 ml of a 4% PLLA (80 mg, MW 180 k) in methylene chloride, and the medium was homogenized at 11-27 k rpm to produce the organic phase. The continuous phase consisted of 12 ml 0.02% aqueous solution of methylcellulose saturated with methylene chloride. Emulsification was initiated by vigorous mixing of the continuous phase at 11 k rpm, following gradual injection of the organic phase. The medium was emulsified for 5 minutes, then the emulsion was transferred into 150 ml DI-water mixing at 400 rpm. All the described procedures were performed at 4° C. The hardening medium was then transferred to room temperature and the organic solvent was extracted over one hour under reduced pressure at −0.7 bar. The hardened microencapsulated particles were collected by filtration and washed with water. The washed microencapsulated particles were lyophilized to remove the excess water. The channeling effect of PEG on IVR of HSA from the above formulations is shown in FIG. 42.

Method for In Vitro Release:

The in vitro release (IVR) of HSA from the encapsulated microencapsulated particles is achieved by addition of 15 ml of the release buffer (20 mM HEPES, 0.01% Tween-80, 0.1 M NaCl, 1 mM $CaCl_2$, pH 7.4) into 15-ml polypropylene centrifuge tubes containing 2.5 mg equivalence of encapsulated HSA, incubated at 37° C. Sampling procedure was described in Example 31.

Example 33

Preparation of PLGA-Encapsulated Pre-Fabricated Leuprolide/Dextran Sulfate Small Spherical Particles A 30% (w/v) polymer solution (4 ml) was prepared by dissolving 1200 mg of a 50:50 polylactide-co-glycolide (PLGA, MW 35 k) in methylene chloride. Next 65.9 mg of pre-fabricated leuprilide/dextran sulfate small spherical particles (LDS) containing 50 mg of leuprolide was suspended in the described polymer solution, using a homogenizer. This suspension was used to generate the O/W emulsion in 12 ml 0.02% aqueous solution of methylcellulose as described in Example 28 (W/O ratio=1:3). The same procedures as Example 28b were followed to prepare the final microencapsulated particles.

The microencapsulated particles had an average particle size of 20 μm with most of them below 50 μm. The results of IVR of leuprolide from the microencapsulated particles are illustrated in FIG. 43.

Method for In Vitro Release:

The in vitro release (IVR) of leuprolide from the microencapsulated particles is achieved by addition of 15 ml of the release buffer (10 mM Na-phosphate buffer, 0.01% Tween-80, 0.9% NaCl, 0.04% $NaN_3$ pH 7.4) into 15-ml polypropylene centrifuge tubes containing 2.5 mg equivalence of encapsulated leuprolide, incubated at 37° C. Sampling procedure was described in Example 28.

Example 34

Preparation of PLGA-Encapsulated Pre-Fabricated Recombinant Human Growth Hormone Small Spherical Particles A 10% (w/v) polymer solution (4 ml) was prepared by dissolving 0.4 g of a PLGA-PEG in methylene chloride. Next 100 mg of prefabricated recombinant human growth hormone small spherical particles (hGHms) was suspended in the described polymer solution, using a homogenizer. The continuous phase consisted of aqueous solution of 0.1% (w/v) methylcellulose and 50 mM phosphate buffer at pH 7.0. Microencapsulation was performed using the continuous setup (FIG. 41A) as described in Example 31. The average particle size of these microencapsulated particles was 25 μm, ranging from 1 to 60 μm. The IVR profile of hGH from the polymeric matrix is shown in FIG. 45.

Method for In Vitro Release:

The IVR of hGH from the microencapsulated particles is achieved as described in Example 28.

Example 35

Determination of Integrity of Microencapsulated Pre-Fabricated Insulin Small Spherical Particles To assess the effect of the microencapsulation process on integrity of encapsulated pre-fabricated insulin small spherical particles, the polymeric microencapsulated particles containing the pre-fabricated INSms were deformulated using a biphasic double extraction method. A weighed sample of the encapsulated INSms were suspended in metylene chloride and gently mixed to dissolve the polymeric matrix. To extract the protein, a 0.01 N HCl was added and the two phases were mixed to create an emulsion. Then, the two phases were separated, the aqueous phase was removed and refreshed with the same solution and the extraction process was repeated. The integrity of the extracted insulin was determined by size exclusion chromatography (SEC). This method identifies extend of monomer, dimer and high molecular weight (HMW) species of INS in the extracted medium. Appropriate controls were used to identify the effect of the deformulation process on the integrity of INS. The results showed no significant effect of this process on INS integrity.

The encapsulated INSms contained 97.5-98.94% monomers of the protein, depending on the conditions and contents of the microencapsulation process, in comparison with 99.13% monomer content in the original INSms (unencapsulated). Content of the dimer species in the encapsulated INSms ranged from 1.04% to 1.99% in comparison with 0.85% in the original INSms. The HMW content of the encapsulated INSms ranged from 0.02% to 0.06% versus 0.02% in the original INSms. The results are summarized in Table 6. The effect of polymeric matrix is depicted in FIGS. 46 and 47.

TABLE 6

Effect of the microencapsulation process on integrity of encapsulated pre-fabricated insulin small spherical particles.

| | Monomer (%) | Dimer (%) | HMW (%) |
|---|---|---|---|
| Unencapsulated INSms | 99.13 | 0.85 | 0.02 |
| Encapsulated INSms | 97.5-98.94 | 1.04-1.99 | 0.02-0.06 |

Example 36

In Vivo Release Insulin from Microencapsulated Pre-Fabricated Insulin Small Spherical Particles In vivo release of insulin from the microencapsulated particles of pre-fabricated insulin small spherical particles was investigated in Sprague Dawley (SD) rats. The animals received an initial subcutaneous dose of 1 IU/kg of the unencapsulated or encapsulated pre-fabricated insulin small spherical particles. ELISA was used to determine the recombinant human insulin (rhINS) serum levels in the collected samples. The results are illustrated in FIG. 48.

While specific embodiments have been illustrated and described, numerous modifications come to mind without departing from the spirit of the invention and the scope of protection is only limited by the scope of the accompanying claims.

What is claimed is:

1. A method for preparing small spherical particles of an active agent comprising:
   providing a solution in a single liquid phase and comprising the active agent, a phase separation enhancing agent and a first solvent; and
   cooling the solution to thereby form a suspension comprising solid small spherical particles of the active agent in a liquid phase comprising the phase separation enhancing agent and the solvent, the small spherical particles being substantially spherical, wherein said cooling is performed at a controlled rate from about 8.6° C./minute to about 26.5° C./minute, wherein said active agent is a macromolecule, and wherein the particles have an average particle size of from about 0.5 μm to about 10 μm.

2. The method of claim 1, further comprising a step selected from the group consisting of: adjusting the concentration of the active agent, adjusting the concentration of the phase-separation enhancing agent, adjusting the ionic strength of the solution, adjusting the pH, and adjusting the osmolality of the solution before or during the cooling step.

3. The method of claim 1 further comprising changing the concentration of the active agent.

4. The method of claim 1 further comprising changing the concentration of the phase separation enhancing agent.

5. The method of claim 1, wherein the solution has a phase transition temperature, a first temperature and a second temperature and the solution is cooled from the first temperature to the second temperature wherein the first temperature is above the phase transition temperature of the solution and the second temperature is below the phase transition temperature of the solution.

6. The method of claim 5, wherein the second temperature is above the freezing point of the solution.

7. The method of claim 5, wherein the second temperature is below the freezing point of the solution.

8. The method of claim 1, wherein the step of providing the solution comprises:
dissolving the phase-separation enhancing agent in the first solvent to form a mixture; and
adding the active agent to the mixture to form the solution.

9. The method of claim 8 further comprising the step of dissolving the active agent in the first solvent or a second solvent which is miscible with the first solvent before adding the active agent to the mixture.

10. The method of claim 6, wherein the solution further comprises a freezing point depression agent to lower the freezing point of the solution.

11. The method of claim 10, wherein the freezing point depression agent is selected from the group of polyethylene glycol and propylene glycol.

12. The method of claim 1, wherein the phase-separation enhancing agent is an aqueous soluble or aqueous miscible agent.

13. The method of claim 1, wherein the phase-separation enhancing agent is selected from the group consisting of linear or branched polymers, carbohydrate-based polymers, polyaliphatic alcohols, poly(vinyl) polymers, polyacrylic acids, polyorganic acids, polyamino acids, co-polymers and block co-polymers, tert-polymers, polyethers, naturally occurring polymers, polyimides, surfactants, polyesters, branched and cyclo-polymers, polyaldehydes, starches, substituted starches, polyethylene glycol, polyvinylpyrrolidone, poloxamers, ethanol, acetone, and isopropanol.

14. The method of claim 1, wherein the phase separation enhancing agent is polyethylene glycol (PEG).

15. The method of claim 1, wherein the small spherical particles further comprises an excipient to enhance the stability of the small spherical particles, to provide controlled release of the active agent from the small spherical particles, or to enhance permeation of the active agent through biological tissues.

16. The method of claim 15, wherein the excipient is selected from the group consisting of: carbohydrates, cations, anions, amino acids, lipids, fatty acids, surfactants, triglycerides, bile acids or their salts, fatty acid esters, and polymers.

17. The method of claim 16, wherein the cation is selected from group consisting of $Zn^{2+}$, $Mg^{2+}$, and $Ca^{2+}$.

18. The method of claim 16, wherein the bile acid is cholate or its salt.

19. The method of claim 1, further comprising the step of harvesting the small spherical particles.

20. The method of claim 19, wherein the step of harvesting the small spherical particles is by washing the particles with a liquid medium at a temperature at which the active agent is not soluble in the liquid medium and the phase-separation enhancing agent is soluble in the liquid medium.

21. The method of claim 20, wherein the step of washing is by diafiltration or centrifugation.

22. The method of claim 20, wherein the liquid medium is aqueous or organic.

23. The method of claim 20, wherein the liquid medium is a supercritical fluid or a mixture of a supercritical fluid and a supercritical fluid miscible solvent.

24. The method of claim 22, wherein the organic liquid medium is selected from the group consisting of: methylene chloride, chloroform, acetonitrate, ethylacetate, ethanol, and pentane.

25. The method of claim 20, wherein the liquid medium further comprises an agent which reduces the solubility of the active agent in the liquid medium.

26. The method of claim 25, wherein the agent to reduce the solubility of the active agent in the liquid medium comprises a complexing ion.

27. The method of claim 26, wherein the complexing ion is selected from the group consisting of: $Zn^{2+}$, $Ca^{2+}$, $Fe^{2+}$, $Mg^{2+}$, $Mn^{2+}$, $Na^+$, and $NH_4^+$.

28. The method of claim 20, further comprises the step of removing the liquid medium.

29. The method of claim 28, wherein the step of removing the liquid medium is by lyophilization, drying or evaporation.

30. The method of claim 20, wherein the liquid medium further comprises an excipient.

31. The method of claim 30, wherein the excipient enhances the stability of the small spherical particles, provides controlled release of the active agent from the small spherical particles, or enhances permeation of the active agent through biological tissues.

32. The method of claim 31, wherein the excipient is selected from the group consisting of: carbohydrates, cations, anions, amino acids, lipids, fatty acids, surfactants, triglycerides, bile acids or their salts, fatty acid esters, and polymers.

33. The method of claim 32, wherein the cation is selected from group consisting of $Zn^{2+}$, $Mg^{2+}$, and $Ca^{2+}$.

34. The method of claim 32, wherein the excipient is cholate or its salt.

35. The method of claim 1, wherein the phase separation enhancing agent is selected from the group consisting of poloxamers, polyethylene glycols, and mixtures thereof.

36. The method of claim 1, wherein the solution comprises an aqueous or aqueous-miscible solvent.

37. The method of claim 36, wherein the aqueous-miscible solvent is selected from the group consisting of: N-methyl-2-pyrrolidinone (N-methyl-2-pyrrolidone), 2-pyrrolidinone (2-pyrrolidone), 1,3-dimethyl-2-imidazolidinone (DMI), dimethylsulfoxide, dimethylacetamide, acetic acid, lactic acid, methanol, ethanol, isopropanol, 3-pentanol, n-propanol, benzyl alcohol, glycerol, polyethylene glycol (PEG), PEG-4, PEG-8, PEG-9, PEG-12, PEG-14, PEG-16, PEG-120, PEG-75, PEG-150, polyethylene glycol esters, PEG-4 dilaurate, PEG-20 dilaurate, PEG-6 isostearate, PEG-8 palmitostearate, PEG-150 palmitostearate, polyethylene glycol sorbitans, PEG-20 sorbitan isostearate, polyethylene glycol monoalkyl ethers, PEG-3 dimethyl ether, PEG-4 dimethyl ether, polypropylene glycol (PPG), polypropylene alginate, PPG-10 butanediol, PPG-10 methyl glucose ether, PPG-20 methyl glucose ether, PPG-15 stearyl ether, propylene glycol dicaprylate/dicaprate, propylene glycol laurate, and glycofurol (tetrahydrofurfuryl alcohol polyethylene glycol ether), or a combination thereof.

38. The method of claim 1, wherein the macromolecule is selected from the group consisting of proteins, polypeptides, carbohydrates, polynucleotides, viruses and nucleic acids.

39. The method of claim 38, wherein the protein is selected from the group consisting of: a protein of the blood clotting cascade, Factor VII, Factor VIII, Factor IX, subtilisin, ovalbumin, alpha-1-antitrypsin, DNAse, superoxide dismutase, lysozyme, ribonuclease, hyaluronidase, collagenase, growth hormone, erythropoetin, insulin-like growth factors or their analogs, interferons, glatiramer, granulocyte-macrophage colony-stimulating factor, granulocyte colony-stimulating factor, antibodies, monoclonal antibodies, polyclonal antibodies, Fab fragments, single-chain antibodies, PEGylated proteins, glycosylated or hyperglycosylated proteins, desmopressin, LHRH agonists such as: leuprolide, goserelin, nafarelin, buserelin, LHRH antagonists, vasopressin, cyclosporine, calcitonin, parathyroid hormone, parathyroid hormone peptides and insulin.

40. The method of claim 1, wherein the particles are suitable for in vivo delivery to a subject in need of the active agent.

41. The method of claim 40, wherein the in vivo delivery is selected from the group consisting of injectable, inhalable, parenteral, topical, oral, rectal, nasal, pulmonary, vaginal, buccal, sublingual, transdermal, transmucosal, otic, ocular, intraocular and ophthalmic.

42. The method of claim 41, wherein the in vivo delivery is by pulmonary delivery.

43. The method of claim 42, wherein the particles are suitable for deposition in the central or peripheral area of the lung of the subject.

44. The method of claim 42, wherein the particles are delivered by a device selected from the group consisting of dry powder inhaler, a metered dose inhaler, and a nebulizer.

45. The method of claim 40, wherein the particles are delivered as a stable liquid suspension.

46. The method of claim 1, wherein the particles have substantially the same particle size.

47. The method of claim 1, wherein the active agent is from about 0.1% to about 100% by weight of the particle.

48. The method of claim 1, wherein the active agent is from about 75% to about 100% by weight of the particle.

49. The method of claim 1, wherein the active agent is equal to or greater than 90% by weight of the particle.

50. The method of claim 1 wherein the small spherical particles have a narrow size distribution.

51. The method of claim 50 wherein the ratio of a volume diameter of the $90^{th}$ percentile of the small spherical particles to the volume diameter of the $10^{th}$ percentile is less than or equal to about 5.

52. The method of claim 1 wherein the active agent in the small spherical particles is semi-crystalline or non-crystalline.

53. A method for preparing small spherical particles of an active agent, the method comprising the steps of:
dissolving the active agent and a phase-separation enhancing agent in an aqueous or aqueous-miscible solvent to form a solution of a single continuous phase, and
cooling the solution to thereby form a suspension comprising solid, small spherical particles of the active agent in a liquid phase comprising the phase-separation enhancing agent, wherein said cooling is performed at a controlled rate from about 8.6° C./minute to about 26.5° C./minute, wherein said active agent is a macromolecule, and wherein the particles have an average particle size of from about 0.5 µm to about 10 µm.

54. The method of claim 53, wherein the solution has a phase transition temperature, a first temperature and a second temperature and the solution is cooled from the first temperature to the second temperature wherein the first temperature is above the phase transition temperature of the solution and the second temperature is below the phase transition temperature of the solution.

55. The method of claim 1 wherein said solution is cooled at a controlled rate to a temperature above the freezing point of said solution.

56. The method of claim 1, wherein the first solvent is water.

57. The method of claim 1, wherein a percentage conversion of the active agent from the starting solution into the particles is at least 90%.

58. The method of claim 1, wherein the active agent released from the particles retains the bioactivity of the active agent in the starting solution, as determined by specific activity.

59. The method of claim 1, wherein the active agent released from the particles retains the structural integrity of the active agent in the starting solution, as determined by circular dichroism spectroscopy.

60. The method of claim 1, wherein the small spherical particles have a geometric standard deviation of less than 2.5.

61. The method of claim 60, wherein the geometric standard deviation is less than 1.8, and a ratio of a volume diameter of the $90^{th}$ percentile of the particles to a volume diameter of the $10^{th}$ percentile of the particles is less than 3.

62. A method for preparing solid, small spherical particles of active agent comprising:
providing an aqueous solution in a single liquid phase and comprising the active agent and a phase separation enhancing agent;
cooling the aqueous solution; thereby forming a suspension comprising solid, small spherical particles of active agent suspended in a liquid phase comprising the phase separation enhancing agent and water, the solid, small spherical particles being substantially spherical, wherein said cooling is performed at a controlled rate from about 8.6° C./minute to about 26.5° C./minute, wherein said active agent is a macromolecule, and wherein the particles have an average particle size of from about 0.5 µm to about 10 µm.

63. The method of claim 62, wherein the cooling the aqueous solution is carried out at a constant or linear rate, a non-linear rate, an intermittent rate, or a programmed rate.

64. The method of claim 62, wherein the cooling the aqueous solution involves cooling the solution to a temperature below the phase transition temperature of the active agent.

65. The method of claim 62, wherein the aqueous solution further comprises a freezing point depressing agent.

66. The method of claim 62, wherein the cooling the aqueous solution includes cooling the solution to a temperature above the freezing point of the solution.

67. The method of claim 65, wherein the freezing point depressing agent comprises polyethylene glycol.

68. The method of claim 1, wherein the active agent comprises insulin.

69. The method of claim 53, wherein the active agent comprises insulin.

70. The method of claim 62, wherein the active agent comprises insulin.

* * * * *